United States Patent [19]
Priebe et al.

[11] Patent Number: 5,874,412
[45] Date of Patent: Feb. 23, 1999

[54] BIS-ANTHRACYCLINES WITH HIGH ACTIVITY AGAINST DOXORUBICIN RESISTANT TUMORS

[76] Inventors: Waldemar Priebe, 4239 Emory St., Houston, Tex. 77005; Jonathan B. Chaires, 716 Pennsylvania Ave., Jackson, Miss. 39210; Teresa Przewloka; Izabela Fokt, both of 12000 Sawmill Rd., #512, The Woodlands, Tex. 77380; Roman Perez-Soler, 2904 Rice Blvd., Houston, Tex. 77005

[21] Appl. No.: 828,198

[22] Filed: Mar. 21, 1997

Related U.S. Application Data

[60] Provisional application No. 60/013,864 Mar. 22, 1996.
[51] Int. Cl.$^6$ .............................. A61K 31/70; C07H 17/08
[52] U.S. Cl. ................................. 514/34; 536/6.4; 552/201
[58] Field of Search ................................ 536/6.4; 514/34, 514/201; 552/201, 34

[56] References Cited

U.S. PATENT DOCUMENTS

| | | | |
|---|---|---|---|
| 4,112,217 | 9/1978 | Henry et al. | 536/6.4 |
| 4,263,428 | 4/1981 | Apple et al. | 536/6.4 |
| 4,749,693 | 6/1988 | Anzelucci et al. | 514/34 |
| 5,132,290 | 7/1992 | Priebe et al. | 514/34 |

OTHER PUBLICATIONS

Arcamone F., "Doxorubicin," Anti–Cancer Antibiotics. New York: American Press, 1981.
Bell et al., "Detection of P–Glycoprotein in Ovarian Cancer: A Molecular Marker Associated With Multidrug Resistance," *J. Clin. Oncol.,* 3:311, 1985.
Bertino, "The Multidrug Resistance Phenotype," *J. Clin. Oncol.,* 3(5):293, 1985.
Bodley et al., "DNA Topoisomerase II–Mediated Interaction of Doxorubicin and Daunorubicin Congeners with DNA$^1$," *Cancer Res.,* 49:5969–5978, 1989.
Booser D.J. and Hortobgyi G.N., "Anthracycline Antibiotics in Cancer Therapy. Focus on Drug Resistance," *Drugs,* 47(2):223–258, 1994.
Bradley et al., "Mechanism of Multidrug Resistance," *Biochem. Biophys. Acta.,* 948:87–128, 1988.
Brandts and Lin, "Study of Strong to Ultralight Protein Interactions Using Differenctial Scanning Calorimetry," *Biochemistry,* 29:6927–6940, 1990.
Capranico et al., "Sequence–Selective Topoisomerase II Inhibition by Anthracycline Derivatives in SV40 DNA: Relationship with DNA Binding Affinity and Cytotoxicity," *Biochem.,* 29:562–569, 1990.
Chaires et al., "A New Generation of Bisintercalating Anthracycline Antibiotics," Abstract 017 Presented at the ACS meeting, Mar. 15, 1996.
Chaires et al., "Structure–Based Design of a New Bisintercalating Anthrecycline Antibiotic," *Journal of Medicinal Chemistry,* 40(3):261–266, 1997.

Chaires J.B., "Application of Equilibrium Binding Methods to Elucidate: The Sequence Specificity of Antibiotic Binding to DNA," Hurley L.H., Ed., Advances in DNA Sequence Specific Agents., 1: *Jai Press,* 1991.
Chaires J.B., "Biophysical Chemistry of Daunomycin–DNA Interaction," *Biophys. Chem.,* 35:191–202, 1990.
Chaires J.B., Herrera J.E., and Waring M.J., "Preferential Binding of Daunomycin to 5' $_T{}^A$ CG and 5' $_T{}^A$ GC Sequences Revealed by Footprinting Titration Experiments,"*Biochemistry,* 29:6145–6153, 1990.
Chaires, J.B., "Daunomycin Binding to DNA: From the Macroscopic to the Microscopic," Eds. Pullman B. and Jortner J., Molecular Basis of Specificity in Nucleic Acid–Drug Interactions: Kluwer Academic Publishers, 123–126, 1990.
Cohen and Eisenberg, "Viscosity and Sedimentation Study of Sonicated DNA–Proflavine Complexes*," *Biopolymers,* 8:45–55, 1969.
Cornbleet et al., "Mitoxantrone for the Treatment of Advanced Breast Cancer: Single–Agent Therapy in Previoulsy Untreated Patients," *Eur. J. Cancer Clin. Oncol.,* 20(9):1141–1146, 1984.
Crothers D.M., "Statistical Thermodynamics of Nucleic Acid Melting Transitions with Coupled Binding Equilibria," *Biopolymers,* 10:2147–2160, 1971.
Curt et al., "Drug Resistance in Cancer," *Cancer Treat. Rep.,* 68:87, 1984.
Danks et al., Atypical Multiple Drug Resistance in a Human Leukemic Cell Line Selected for Resistance to Teniposide (VM–26)$^1$ *Cancer Res.,* 47:1297–1301, 1987.
Dawson K.M., "Activity of SC33428, A Novel Bis–Hydrozone Bridged Derivative of 4–Demethoxydaunomycin, Against Experimental Tumors in Mice," *Cancer Res.,* 43:2880–2883, 1983.
Denny et al., "Potential Anti–Tumor Agents. 39. Anilino Ring Geometry of Amsacrine and Derivatives: Relationship to DNA Binding and Anti–Tumor Activity," *J. Med. Chem.,* 26(11):1625–1630, 1983.
Dervan P., "Design of Sequence–Specific DNA–Binding Molecules," *Science,* 232:464–471, 1986.
Dowd, Editor, "The Physicians Desk References," Medical Economics Company Inc., Oradell, N.J., 1990.
Fojo et al., "Expression of a Multidrug–Resistance Gene in Human Tumors," *P.N.A.S.,* 84:265–269, 1987.

(List continued on next page.)

*Primary Examiner*—Elli Peselev
*Attorney, Agent, or Firm*—Arnold White & Durkee

[57] ABSTRACT

The present invention discloses new and novel bisanthracyclines linked through the saccharide portions. These compounds show high activity against two clinically relevant mechanisms of resistance. A novel approach of the invention produces compounds that are as active or more so than the parent compounds. Furthermore, the inventor's discovery is also for the design of effective DNA-binding bisanthracyclines as well as anthracyclines mixed with other intercalators and groove binders.

25 Claims, 21 Drawing Sheets

OTHER PUBLICATIONS

Gallois et al., "The Overall Partitioning of Anthracyclines into Phosphatidyl–Containing Model Membranes Depend Neither on the Drug Charge Nor on the Presence of Anionic Phospholipids," Abstract 051 Presented at the ACS meeting, Mar. 15, 1996.

Ganapathi, et al., "N–Benzyladriamycin–14–Valerate Versus Progressively Doxorubicin–Resistant Murine Tumors: Cellular Pharmacology and Characterization of Cross–Resistance In Vitro and In Vivo,"*Br. J. Cancer*, 60:819–826, 1989.

Gennaro, A.R., Editor, "Remington's Pharmaceutical Sciences,"Mack Publishing Company, Easton, Pennsylvania, 1990.

Goldie et al., "A Mathematic Model for Relating the Drug Sensitivity of Tumors to Their Spontaneous Mutation Rate $^1$," *Cancer Treat. Rep.*, 63(11–12):1727–1731, 1979.

Goldie et al., "The Genetic Origin of Drug Resistance in Neoplasmas: Implications for Systemic therapy," *Cancer Res.*, 44:3643–3653, 1984.

Green, Reade, and Ware, "Rapid Colormetric Assay for Cell Viability: Application to the Quantitation of Cytotoxic and Growth Inhibitory Lymphokines," *J. Immunol. Methods*, 70:257–268, 1984.

Gros et al., "Isolation and Expression of a Complementary DNA that Confers Multidrug Resistance," *Nature*, 323:728–731, 1986.

Hsiang et al., "Topoisomerase II–Mediated DNA Cleavage by Amonafide and Its Structural Analogs," *Mol. Pharmacol.*, 36(3):371–376, 1989.

Israel et al., "Comparative Uptake and Retention of Adriamycin and N–Benzyladriamycin–14–Valerate in Human CEM Leukemic Lymphocyte Cell Cultures," *Cancer Chemother. Pharmacol.*, 25:177–183, 1989.

Israel et al., "Comparative Effects of Adriamycin and DNA–Non–Binding Analogues on DNA, RNA, and Protein Synthesis in Vitro," *Cancer Chemother. Pharmacol.*, 20:277–284, 1987.

Katsumata et al., "Prevention of Breast Tumor Development In Vivo by Down–Regulation of the p185$^{neu}$ Receptor", *Nature Med.*, 1(7):644–648, 1995.

Kolata, "Why Do Cancer Cells Resist Drugs?" *Science*, 231:220–221, 1986.

Kopka et al., "Binding of An Antitumor Drug to DNA Netropsin and C–G–C–G–A–A–T–T$^{BR}$C–C–G–C–G", *J. Mol. Biol.*, 183:553–563, 1985.

Krawczyk et al., "Synthesis and Cytotoxic Properties of 14–0–Acylated Hydroxyrubicins," Abstract 048 Presented at the ACS meeting, Mar. 15, 1996.

Lampidis et al., "Lipophilicity and Positive Charge Influence Selectivity and Localization of Anthracyclines in P–GP Mediated Multidrug Resistant and Sensitive Cell Types," Abstract 027 Presented at the ACS meeting, Mar. 15, 1996.

Lothstein et al., "Anthracycline Metabolism and Its Therapeutic Potential," Abstract 030 Presented at the ACS meeting, Mar. 15, 1996.

Lown JW, "Targeting the DNA Minor Groove for Control of Biological Function: Progress, Challenges and Prospects", *Chemtracts —Org. Chem.*, 6:205–237, 1903.

Lown JW., "Anthracycline and Anthracenedione–Based Anticancer Agents. Bioactive Molecules," 6: Amsterdam: Elsevier, 1988.

McGhee JD, "Theoretical Calculations of the Halix–Coil Transition of DNA in the Presence of Large, Cooperatively Binding Ligands", *Biopolymers*, 15:1345–1375, 1976.

Moscow et al., "Multidrug Resistance," Journal of the National Cancer Institute, 80(1):14–20, 1988.

Mosmann, "Rapid Colorimetric Assay for Cellular Growth and Survival: Application to Proliferation and Cytotoxicity Assay", *J. Immunol. Methods*, 65:55–63, 1983.

Mrksich et al., "Antiparallel Side–by–Side Dimeric Motif for Sequence–Specific Recognition in the Minor Groove of DNA by the Designed Peptide 1–Methylimidazole–2–Carboxamide Netropsin", *Proc. Nat'l. Acad. Sci. U.S.A.*, 89:7586–7590, 1992.

Norris et al., "Expression of the Gene for Multidrug–Resistance–Associated Protein and Outcome in Patients with neuroblastoma," *N. Engl. J. Med.*, 334:231–238, 1996.

Nowell, "Mechanisms of Tumor Progression," *Cancer Res.*, 46:2203–2207, 1986.

Pelton and Wemmer, Structural Characterization of a 2:1 Distamycin A–d(CGCAAATTGGC) Complex by Two–Dimensional NMR, *Proc. Nat'l. Acad. Sci. U.S.A.*, 86:5723–5727, 1989.

Perez–Soler et al., "Development of Liposomal–Annamycin," Abstract 035 Presented at the ACS meeting, Mar. 15, 1996.

Phillips, Brownlee, Reiss, and Scourides, "Bis–Daunomycin Hydrazones: Interactions with DNA," Investigational New Drugs, 10:79–88, 1992.

Pommier et al., "Altered DNA Topoisomerase II Activity in Chinese Hamster Cells Resistant to Topoisomerase II Inhibitors," *Cancer Res.*, 46:3075–3081, 1986.

Pommier et al., "Reduced Formation of Protein–Associated DNA Strand Breaks in Chinese Hamster Cells Resistant to Topoisomerase II Inhibitors," *Cancer Research*, 46:611–616, 1986.

Potmesil et al., "Structure and Biological Activity of N–Substituted Anthracyclines: Correlation with Drug–DNA Topoisomerase II Interaction," Experimental Therapeutics, Proceedings of AACR, 28:262, Mar. 1987, Abstract 1034.

Priebe et al., "Exploration of Target–Governed Design of Anthracyclines," Abstract 016 Presented at the ACS meeting, Mar. 15, 1996.

Priebe et al., "Photoaffinity Labeling of P–Glycoprotein and Its Inhibition by Charged and Uncharged Anthracyclines," Abstract 049 Presented at the ACS meeting, Mar. 15, 1996.

Priebe W., "Anthracycline Antibiotics. New Analogues, Methods of Delivery, and Mechanisms of Action," Washington, D.C.: American Chemical Society, 1995.

Priebe W., "Mechanism of Action–Governed Design of Anthracycline Antibiotics: A Turn–Off/Turn–On Approach," Current Pharmaceutical Design, 1:51–68, 1995.

Priebe, Neamati, and Perez–Soler, "3'–Hydroxy–Esorubicin Halogenated at C–2'," *J. Antibiot.*, 45(3):386–393, 1992.

Priebe, Van, Burke, and Perez_Soler, "Removal of the Basic Center from Doxorubicin Partially Overcomes Multidrug Resistance and Decreases Cardiotoxicity," Anti–Cancer Drugs, 4:37–48, 1993.

Pullman B., "Molecular Mechanisms of Specificity in DNA–Antitumor Drug Interactions," In Advances in Drug Research, 18:1–113, 1989.

Pullman B., "Sequence Specificity in the Binding of Anti––Tumor Anthracyclines to DNA: A Success of Therory," Anti–Cancer Drug Design, 7:95–105, 1991.

Rubinstein et al., "Comparison of In Vitro Anti–Cancer–Drug–Screening Data Generated with A Tetrazolium Assay Versus a Protein Assay Against a Diverse Panel of Human Tumor Cell Lines", *J. Nat'l. Cancer Inst.,* 82(13):1113–1120, 1990.

Silber et al., "Metabolic Activation of N–Acylanthracyclines Precedes Their Interaction with DNA Topoisomerase II[1]," NCI Monographs, 4: 111–115, 1987.

Skorobogaty et al., "The DNA–Association and Biological Activity of a New Bis (14–thiadaunomycin)", *Anti–Cancer Drug Des.,* 3:41–56, 1988.

Stryer, "Biochemistry", Freeman and Co., San Francisco, 1981.

Suh and Chaires, "Criteria for the Mode of Binding of DNA Binding Agents", *Bioorg. Med. Chem.,* 3(6):723–728, 1995.

Talbot, et al., "Anthrpyrazole CI941: A Highly Active New Agent in the Treatment of Advanced Breast Cancer", *J. Clin. Oncol.,* 9(12):2141–2147, 1991.

Traganos et al., "Effects of New N–Alkyl Analogues of Adriamycin on in Vitro Survival and Cell Cycle Progression of L1210 Cells," *Cancer Res.,* 45:6273–6279, 1985.

Valentini et al., "Association of Anthracycline Derivatives with DNA: A Fluorescence Study," I1 Farmaco Ed., Sci., 40:377–390, 1985.

Wakelin L.P.G., "Polyfunctional DNA Intercalating Agents," *Medicinal Research Rev.,* 6:275–340, 1986.

Wang et al., "Interactions between an Anthracycline Antibiotic and DNA: Molecular Structure of Daunomycin Complexed to d(CpGpTpApCpGp) at 1.2–A Resolution", *Biochemistry,* 26:1152–1163, 1987.

Wang et al., "Mutual Conformational Adaptation of Both Ligand and Receptor in Antitumor Drug–DNA Complexes," In Molecular Basis of Specificity in Nucleic Acid–Drug Interactions, Pullman and Jortner, Eds., Dordrecht, Netherlands: Kluwer Academic Publishers, 1–24, 1990.

Wilson WD, *Reversible Interactions of Nucleic Acids with Small Molecules,* In Nucleic Acids in Chemistry and Biology Blackburn, G.M., Guit, M.J., Eds.; IRL Press, Oxford 297–336, 1990.

Young et al., "The Anthracycline Antineoplastic Drugs," *N. Engl. J. Med.,* 305(3):139–153, 1981.

R=H; DAUNORUBICIN
R=OH; DOXORUBICIN daunomycinone (1)

(2)

(3)

BIS-ANTHRACYCLINES WITH HIGH ACTIVITY AGAINST DOXORUBICIN RESISTANT TUMORS

BACKGROUND OF THE INVENTION

The present application is a continuation in part of US Provisional Patent Application No. 60/013,869 filed Mar. 22, 1996.

1. Field of the Invention

The present invention relates generally to the treatment of cancer. More particularly, it concerns novel compounds useful for chemotherapy, methods of synthesis of these compounds and methods of treatment employing these compounds. The novel compounds are bis-anthracyclines related to anthracyclines such as doxorubicin which is known to have anti-tumor activity.

2. Description of the Related Art

Resistance of tumor cells to the killing effects of chemotherapy is one of the central problems in the management of cancer. It is now apparent that at diagnosis many human tumors already contain cancer cells that are resistant to standard chemotherapeutic agents. Spontaneous mutation toward drug resistance is estimated to occur in one of every $10^6$ to $10^7$ cancer cells; this mutation rate appears to be independent of any selective pressure from drug therapy, although radiation therapy and chemotherapy may give rise to additional mutations and contribute to tumor progression within cancer cell populations (Goldie et al., 1979; Goldie et al., 1984; Nowell, 1986). The cancer cell burden at diagnosis is therefore of paramount importance because even tumors as small as 1 cm ($10^9$ cells) could contain as many as 100 to 1,000 drug-resistant cells prior to the start of therapy.

Selective killing of only the tumor cells sensitive to the drugs leads to an overgrowth of tumor cells that are resistant to the chemotherapy. Mechanisms of drug resistance include decreased drug accumulation (particularly in multi-drug resistance), accelerated metabolism of the drug and other alterations of drug metabolism, and an increase in the ability of the cell to repair drug-induced damage (Curt et al., 1984; and Kolate, 1986). The cells that overgrow the tumor population not only are resistant to the agents used but also tend to be resistant to other drugs, many of which have dissimilar mechanisms of action. This phenomenon, called pleiotropic drug resistance or multi-drug resistance (MDR), may account for much of the drug resistance that occurs in previously treated cancer patients.

Gene amplification (i.e., the production of extra copies of genes within a cell) is one of the mechanisms that can lead to drug resistance. Gene amplification is involved in the phenomenon of multi-drug resistance. Multi-drug resistance appears to be linked to over-expression of a cell membrane glycoprotein, termed P-glycoprotein, on the surface of cancer cells (Bell et al., 1985; and Bertino, 1985). The action of this glycoprotein is unknown, but its over-expression is associated with decreased accumulation of multiple chemotherapeutic drugs within the resistant cells. A multi-drug-resistance gene that encodes the P-glycoprotein has been isolated and sequenced, and when it is transferred, this gene confers drug resistance on previously drug-sensitive cells (Gros et al., 1986). The multi-drug-resistance gene termed mdrl is expressed in several normal tissues, and its expression is increased in some human tumors (Fojo et al., 1987). Various human tumors are now being analyzed to determine whether they express this gene. Because many heavily treated patients who are in relapse harbor tumors that do not show over-expression of the mdrl gene, it appears that other mechanisms are probably also involved in causing resistance to chemotherapy.

The commonly used chemotherapeutic agents are classified by their mode of action, origin, or structure, although some drugs do not fit clearly into any single group. The categories include alkylating agents, anti-metabolites, antibiotics, alkaloids, and miscellaneous agents (including hormones); agents in the different categories have different sites of action.

Antibiotics are biologic products of bacteria or fungi. They do not share a single mechanism of action. The anthracyclines daunorubicin and doxorubicin (DOX) are some of the more commonly used chemotherapeutic antibiotics. The anthracyclines achieve their cytotoxic effect by several mechanism, including intercalation between DNA strands, thereby interfering with DNA and RNA synthesis; production of free radicals that react with and damage intracellular proteins and nucleic acids; chelation of divalent cations; and reaction with cell membranes. The wide range of potential sites of action may account for the broad efficacy as well as the toxicity of the anthracyclines (Young et al., 1985).

The anthracycline antibiotics are produced by the fungus *Streptomyces peuceitius* var. caesius. Although they differ only slightly in chemical structure, daunorubicin has been used primarily in the acute leukemias, whereas doxorubicin displays broader activity against human neoplasms, including a variety of solid tumors. The clinical value of both agents is limited by an unusual cardiomyopathy, the occurrence of which is related to the total dose of the drug; it is often irreversible. In a search for agents with high antitumor activity but reduced cardiac toxicity, anthracycline derivatives and related compounds have been prepared. Several of these have shown promise in the early stages of clinical study, including epirubicin and the synthetic compound mitoxantrone, which is an amino anthracenedione.

The anthracycline antibiotics have tetracycline ring structures with an unusual sugar, daunosamine, attached by glycosidic linkage. Cytotoxic agents of this class all have quinone and hydroquinone moieties on adjacent rings that permit them to function as electron-accepting and donating agents. Although there are marked differences in the clinical use of daunorubicin and doxorubicin, their chemical structures differ only by a single hydroxyl group on C14. The chemical structures of daunorubicin and doxorubicin are shown in FIG. 1.

Unfortunately, concomitant with its anti-tumor activity, DOX can produce adverse systemic effects, including acute myelosuppression, cumulative cardiotoxicity, and gastrointestinal toxicity (Young et al., 1985). At the cellular level, in both cultured mammalian cells and primary tumor cells, DOX can select for multiple mechanisms of drug resistance that decrease its chemotherapeutic efficacy. These mechanisms include P-gp-mediated MDR, characterized by the energy-dependent transport of drugs from the cell (Bradley et al., 1988), and resistance conferred by decreased topoisomerase II activity, resulting in the decreased anthracycline-induced DNA strand scission (Danks et al., 1987; Pommier et al., 1986; Moscow et al., 1988.

Among the potential avenues of circumvention of systemic toxicity and cellular drug resistance of the natural anthracyclines is the development of semi-synthetic anthracycline analogues which demonstrate greater tumor-specific toxicity and less susceptibility to various forms of resistance.

The development of drug resistance is one of the major obstacles in the management of cancer. There are various types of drug resistance, for example, classic MDR as opposed to AD 198 resistance. Furthermore, different cell lines can establish resistance to the same drug in different ways, as seen in the case of the differences in AD 198 resistance in AD 198$^R$ cells as opposed to A300 cells. One of the traditional ways to attempt to circumvent this problem of drug resistance has been combination chemotherapy.

Combination drug therapy is the basis for most chemotherapy employed to treat breast, lung, and ovarian cancers as well as Hodgkin's disease, non-Hodgkin's lymphomas, acute leukemias, and carcinoma of the testes.

Combination chemotherapy uses the differing mechanisms of action and cytotoxic potentials of multiple drugs. Although all chemotherapeutic drugs are most effective on cells that are active in DNA synthesis, many agents—particularly the alkylating agents—can kill cells that are not cycling. Such agents are termed non-cell proliferation-dependent agents can shrink tumor mass by reducing cell numbers; the surviving cells will then move into the cycling compartment, where they are more susceptible to cell proliferation-dependent drugs. The combined use of agents less dependent on the cell cycle followed by those dependent on cell proliferation is effective in enhancing tumor cell death. Each cycle of treatment kills a fixed fraction of cells, so repetitive cycles are required for cure. For example, a drug combination that kills 99.9 percent of cancer cells per treatment cycle would have to be repeated at least six times to eliminate an average tumor burden (if tumor cells did not re-grow between cycles).

Although combination chemotherapy has been successful in many cases, the need still exists for new anti-cancer drugs. These new drugs could be such that they are useful in conjunction with standard combination chemotherapy requires. Or, these new drugs could attack drug resistant tumors by having the ability to kill cells of multiple resistance phenotypes.

A drug that exhibits the ability to overcome multiple drug resistance could be employed as a chemotherapeutic agent either alone or in combination with other drugs. The potential advantages of using such a drug in combination with chemotherapy would be the need to employ fewer toxic compounds in the combination, cost savings, and a synergistic effect leading to a treatment regime involving fewer treatments.

Doxorubicin's broad spectrum of activity against most hematological malignancies as well as carcinomas of the lung, breast, and ovary has made it a leading agent in the treatment of neoplastic disease (Arcamone, 1981; Lown, 1988; Priebe, 1995). Since the discovery of daunorubicin and doxorubicin (FIG. 1), the mechanistic details of the antitumor activity of anthracycline antibiotics have been actively investigated (Priebe, 1995; Priebe, 1995; Booser, 1994).

Although the exact mechanism or mechanisms by which doxorubicin kills cancer cells is still not totally clear, a variety of biochemical evidence implicates nuclear targets in anthracycline-mediated anti-cancer action, those targets being DNA and the DNA-processing enzyme topoisomerase II. Intercalation of anthracyclines into free DNA as well as nucleosomal DNA has been the subjects of numerous reports. In fact, doxorubicin and daunorubicin are now considered to be among the best characterized intercalators, (Chaires, 1990; Chaires, 1990) and the DNA binding affinity of a series of anthracycline antibiotics and their biological activity have been correlated (Valentini et al., 1985). Interference with topoisomerase II activity resulting in protein-linked DNA strand breaks has been linked to anthracycline-induced cell damage. Furthermore, DNA binding has been shown to be necessary for the inhibition of topoisomerase II by anthracyclines (Bodley et al., 1989; Capranico et al., 1990).

Recent studies of anthracycline-DNA interactions have led to a better understanding of the nature of daunorubicin-DNA binding. Investigation of site and sequence specificities revealed that daunorubicin shows preference for binding dGdC-rich regions of DNA that are flanked by A:T base pairs and that the triplet sequences 5'-A/TCG and 5'-A/TGC are preferred binding sites (Chaires et al., 1990; Chaires, 1991; Pullman, 1989; Pullman, 1991; Wang et al., 1990). Interaction of daunorubicin with DNA is probably the best understood of intercalation reactions, thus offering important clues for the rational design of new DNA binding compounds with enhanced binding affinity and sequence selectivity. In this invention the inventors exploit this information to design novel bis-intercalating anthracyclines.

Bifunctional DNA intercalating agents have attracted considerable interest (Wakelin, 1986). Bis-intercalators, both naturally occurring and synthetic, have generally been found to bind more tightly to DNA than mono-intercalators. Bis-intercalators usually have DNA binding constants that are several orders of magnitude larger than those observed for mono-intercalators. The rate of dissociation is generally slower, and consequently, the lifetime of the bis-intercalator-DNA complex is longer than that of a mono-intercalator. Perhaps more importantly, bis-intercalators have larger site sizes than do mono-intercalators. Since the number of DNA base pairs bound to any ligand dictates the possible absolute specificity of the ligand-DNA interaction (Dervan, 1986), a larger site could possibly result in an enhanced sequence selectivity. Still despite the potential of bis-intercalators, the currently known compounds have certain drawbacks All currently known bisanthracyclines have monomers linked through their C-13 carbonyl functions by a dicarboxylic acid hydrazine bridge (FIG. 2) (Apple et al., 1981; Dawson, 1983; Henry and Tong, 1978; Phillips et al., 1992). However, the carbonyl function at the C-13 position participates in hydrogen bonding interactions that stabilize the drug-DNA complex. Therefore, derivatization at that position should interfere with such interactions so that the monomer units within the bis-intercalator will not retain their optimal binding potential. Thus, previous attempts to synthesize anthracycline bis-intercalators were flawed by a design strategy that used ketone at the C-13 as a linking function, which makes compounds with such a link less active than the parent compound.

SUMMARY OF THE INVENTION

The present invention seeks to overcome drawbacks inherent in the prior art by providing compositions of agents that are capable of overcoming multi-drug resistance. This invention involves novel compounds that have utility as anti-tumor and/or chemotherapeutic drugs, methods of synthesizing these compounds and methods of using these compounds to treat patients with cancer. The invention is generally based on the discovery that anthracycline derivatives that have aromatic rings attached to their sugar moiety have a suprisingly strong ability to kill tumor cells.

To overcome the problem of using the C13 functional group of anthracyclines to form bisanthracyclines, the inventors have designed anthracyclines connected at positions which would not interfere with DNA binding, and the inventors have synthesized anthracyclines connected at the sugar portion by position 3' or 4'. These actions produced bisanthracyclines which exhibit activity substantially different from the activities of doxorubicin or daunorubicin. These compounds are active against doxorubicin resistant tumors. This indicates that bisanthracyclines are mechanistically different from monomers like doxorubicin or doxorubicin.

The present invention contemplates a bis-anthracycline compound comprising a first anthracycline analog operatively linked to a second anthracycline analog via the saccharide units of the first and second anthracycline analogs. Such compounds may comprise a third anthracycline analog operatively linked to said first or said second anthracycline analog. In such compounds the first and second anthracycline analogs are operatively linked via a spacer unit positioned between said saccharide units. In some preferred embodiments, the first and/or second anthracycline analog is doxorubicin, daunorubicin, idarubicin, epirubicin, pirarubicin, esorubicin, carminomycin, or aclacinomycin. The saccharide of the first and/or second anthracycline analog is a mono-, di-, or oligosaccharide. In preferred embodiments, the linker is: a phenyl group, a benzyl group, an aryl group, an alkyl group, a heterocycle, an aromatic heterocycle, a cycloalkane group, a cycloalkyl group , an alkylaryl group, an aryloalky group, an aryl group linked to another aryl group through an ester linkage, an aryl group linked to an alkyl group with an ester linkage, an aryl group linked to another aryl group through an ether linkage, an aryl group linked to an alkyl group through a thiolester linkage, an alkyl group linked to another alkyl group through an ester linkage, an alkyl group linked to another alkyl group through an ether linkage, an alkyl group linked to another alkyl group through an amino group, an aryl group linked to an alkyl through an amino group, an alkyl group linked to another alkyl group through a disulphide group, an aryl group linked to another alkyl group through a disulphide group, an aryl group linked to another aryl group through a disulphide group, an alkyl group linked to another alkyl group through a thioester linkage, an aryl group linked to an alkyl group through a polyester linkage, an aryl group linked to another aryl group through a polyester linkage, an alkyl group linked to another alkyl group through a polyamine linkage, an aryl group linked to an alkyl group through a polyamine linkage, an aryl group linked to another aryl through a polyamine linkage, an alkyl group linked to another alkyl group through a polythioester linkage, an aryl group linked to an alkyl group through a polythioester linkage, or an aryl group linked to another aryl through a polythioester linkage.

Some preferred bis-anthracyclines have the formula:

STRUCTURE 1

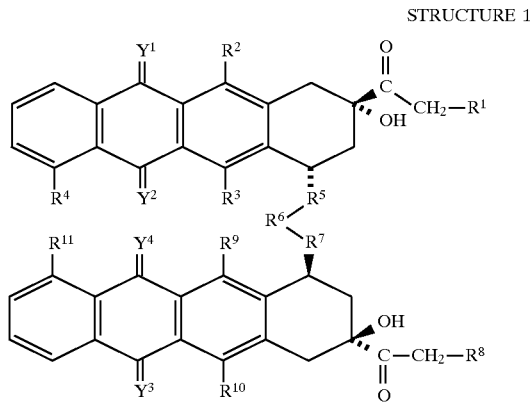

wherein:

$R^1$ is a hydrogen (—H) group, an hydroxyl group (—OH), a methoxy group (—OCH$_3$), a fatty acyl group having the general structure —O—CO(CH$_2$)$_n$CH$_3$, wherein n=an integer from 1 to about 20, or a fatty acyl group having the general structure —O— CO(CH2)$_1$(CH=CH)$_m$(CH2)$_n$CH$_3$ l is an integer between 1 to 3, m is an integer between 1 and about 6 and n is an integer between I to about 9;

each of $R^2$, $R^3$, $R^9$, and $R^{10}$, $R^{11}$ is, independently of the others, a hydrogen (—H) group, an hydroxyl group (—OH), a methoxy group (—OCH$_3$) or a double bonded oxygen moiety;

$R^4$ and $R^{11}$ are, independently of the other, a hydrogen (—H) group, an hydroxyl group (—OH), a methoxy group (—OCH$_3$) or a halide ion $R^5$ and $R^7$ are, independently of each other, a saccharide or a molecule resembling a carbohydrate molecule;

$R^6$ is a phenyl group, a benzyl group, an aryl group, an alkyl group, a heterocycle, an aromatic heterocycle, a cycloalkane group, a cycloalkyl group , an alkylaryl group, an aryloalky group, an aryl group linked to another aryl group through an ester linkage, an aryl group linked to an alkyl group with an ester linkage, an aryl group linked to another aryl group through an ether linkage, an aryl group linked to an alkyl group through a thiolester linkage, an alkyl group linked to another alkyl group through an ester linkage, an alkyl group linked to another alkyl group through an ether linkage, an alkyl group linked to another alkyl group through an amino group, an aryl group linked to an alkyl through an amino group, an alkyl group linked to another alkyl group through a disulphide group, an aryl group linked to another alkyl group through a disulphide group, an aryl group linked to another aryl group through a disulphide group, an alkyl group linked to another alkyl group through a thioester linkage, an aryl group linked to an alkyl group through a polyester linkage, an aryl group linked to another aryl group through a polyester linkage, an alkyl group linked to another alkyl group through a polyamine linkage, an aryl group linked to an alkyl group through a polyamine linkage, an aryl group linked to another aryl through a polyamine linkage, an alkyl group linked to another alkyl group through a polythioester linkage, an aryl group linked to an alkyl group through a polythioester linkage, or an aryl group linked to another aryl through a polythioester linkage;

$R^8$ is a hydrogen (—H) group, an hydroxyl group (—OH), a methoxy group (—OCH$_3$), a fatty acyl group having the structure —O—CO(CH$_2$)$_n$CH$_3$, wherein n=an integer from 1 to about 20, or a fatty acyl group having the general structure —O—CO(CH$_2$)$_l$(CH=CH)m(CH$_2$)$_n$CH$_3$ where l is an integer between 1 to 3, m is an integer between 1 and 6 and n is an integer between 1–9; and each of $Y^1$, $Y^2$, $Y^3$, and $Y^4$ is, independently of the others, a hydrogen (—H) group; an hydroxyl group (—OH); a methoxy group (—OCH$_3$); or a double bonded oxygen, suphur, or nitrogen group.

In some preferred compounds having variations of Structure 1, $R^5$ and $R^7$ are, independently of each other, a saccharide with the configuration of ribose, arabinose, xylose, lyxose, allose, altrose, glucose, mannose, fructose, glucose, idose, galactose, ribulose, sorbose, tagatose, gluconic acid, glucuronic acid, glucaric acididuronic acid, rhamnose, 2-dioxy-rhamnose, fucose, 2-dioxy-fucose, N-acetyl glucosamine, N-acetyl galactosamine, N-acetyl neuraminic acid, sialic acid, duanosamine, or acosamine. Further, $R^5$ and $R^7$ may be, independently of each other, a mono-, di-, or polysaccharide, with the linkage between $R^5$ and $R^7$ being between any sugar ring of $R^5$ and any sugar ring of $R^7$ if one or both of $R^5$ and $R^7$ is a di- or polysaccharide. In some embodiments the linker may connect the 2'-amino group of the sugar moiety of one or both of the first anthracycline and the second anthracycline, for example, FIG. 22 shows the first anthracycline linked via the 2' amino group of its sugar moiety to the second anthracycline via the 2' amino group of the second anthracycline. In yet other examples, the linker may connect a first anthracycline to a second anthracycline via either the second sugar moiety of a disaccharide, the third sugar moiety of a trisaccharide, or the ultimate sugar moiety of a polysaccharide that forms $R^5$ or $R^7$. For example FIG. 23 shows a first anthracycline linked via the 3' amino group of a second sugar moiety of a disaccharide to the 3' amino group of a second sugar moiety in a dissacharide of the second anthracycline. Likewise, FIG. 24 shows a first anthracycline linked via the 3' amino group of a third sugar moiety of a trisaccharide to the 3'amino group of a third sugar moiety in a trisacharide of the second anthracyline. In FIG. 22, FIG. 23 and FIG. 24 X, Y, or Z can be any functional group, and W is any functional aglycone of an anthracycline.

In some preferred compounds having variations of Structure 1, $R^6$ is an alkyl group or an ring-based group. In preferred cases where $R^6$ is an alkyl group, it may have the formula $CH_3(CH_2)_nCH_3$ where n is an integer from 1 to about 100, the formula of a polyether, alkyl group of the formula is a polyamine, the formula $CH_3(CH=CH)_n(CH)_mCH_3$ where n is an integer from 1 to about 20 and m is an integer from 1 to about 100, or the formula $CH_3(CH\equiv CH)_n(CH)_mCH_3$ where n is an integer from 1 to about 20 and m is an integer from 1 to about 100. In preferred cases where $R^6$ is a ring-based group, it may have the formula of a ring-based group of a cyclohexane; cyclohexene; or aryl group that is is a phenyl; benzyl; toluene; aniline; cumene; styrene; benzaldehyde; biphenyl group; a xylene. In some preferred embodiments, the aryl group of is a substituted aryl group. For example, the aryl group may be substituted with an halide ion such as, for example, a fluoride, chloride, bromide or iodide ion. Alternatively, the aryl group may be substituted with an another aryl group, alkyl group, a methoxy group, an hydroxyl group, nitro group, amino group, another aryl group, an amido group, a double bonded oxygen moiety, a phenyl, benzyl, cyclohexane, cyclohexene, toluene, aniline, cumene, styrene, benzaldehyde, biphenyl group, or a xylene.

Two particularly preferred compounds of the invention have with the structure of Structure 2 and Structure 3.

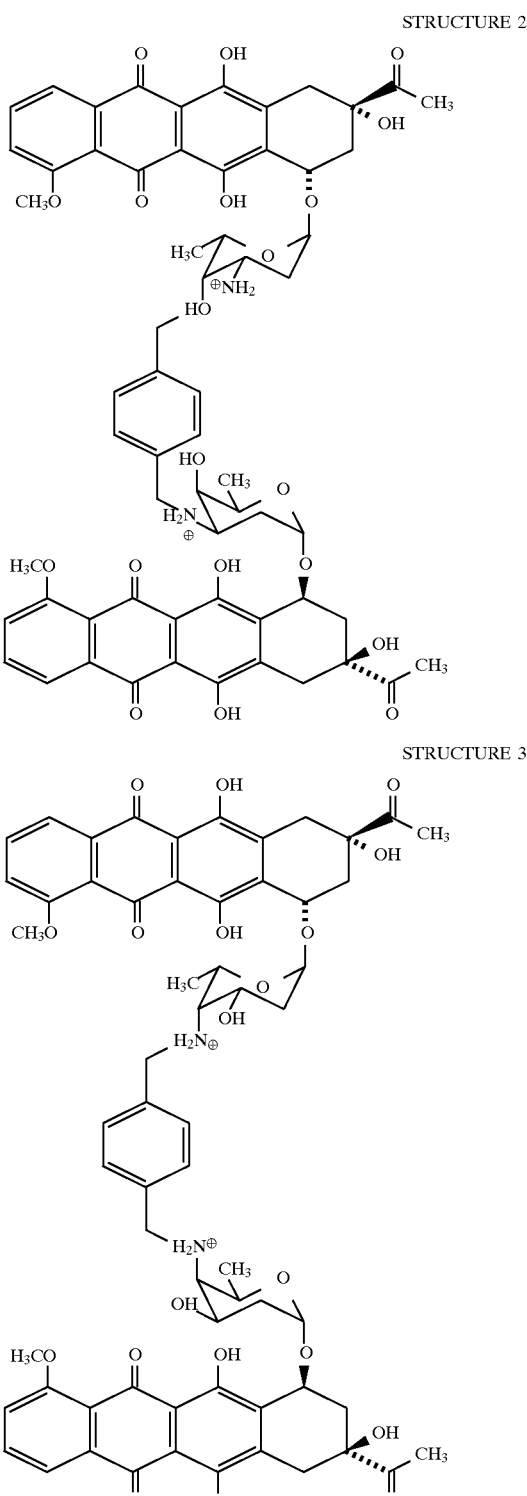

STRUCTURE 2

STRUCTURE 3

STRUCTURE 3

Chloride salts of the compounds of Structures 2 and 3 are also contemplated by the invention.

Specific other embodiments of the invention are shown in FIG. 15, FIG. 16, FIG. 17, FIG. 18, and FIG. 19.

The invention contemplates methods of preparing bis-anthracyclines. For example, the a invention contemplates methods of preparing a bis-anthracycline as described in Structure 1, which comprise:

preparing a first anthracycline of formula:

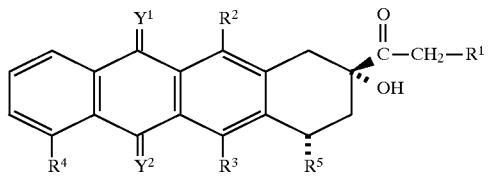

preparing a second anthracycline of general formula:

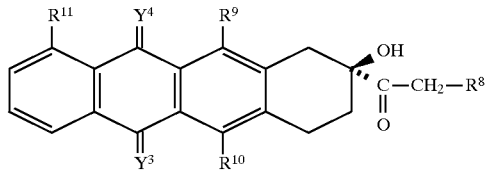

wherein:

$R^1$ is a hydrogen (—H) group, an hydroxyl group (—OH), a methoxy group (—OCH$_3$), a fatty acyl group having the general structure —O—CO(CH2)$_n$CH$_3$, wherein n=an integer from 1 to about 20, or a fatty acyl group having the general structure —O—CO(CH2)$_l$(CH═CH)$_m$(CH2)$_n$CH$_3$ l is an integer between 1 to 3, m is an integer between 1 and about 6 and n is an integer between 1 to about 9;

each of $R^2$, $R^3$, $R^4$, $R^9$, $R^{10}$, $R^{11}$ is, independently of the others, a hydrogen (—H) group, an hydroxyl group (—OH), a methoxy group (—OCH$_3$) or a double bonded oxygen moiety;

$R^5$ and $R^7$ are, independently of each other, a saccharide or a molecule resembling a carbohydrate molecule;

$R^8$ is a hydrogen (—H) group, an hydroxyl group (—OH), a methoxy group (—OCH$_3$), a fatty acyl group having the structure —O—CO(CH2)$_n$CH$_3$, wherein n=an integer from 1 to about 20, or a fatty acyl group having the general structure —O—CO(CH$_2$)$_l$(CH═CH)$_m$(CH$_2$)$_n$CH$_3$ where l is an integer between 1 to 3, m is an integer between 1 and 6 and n is an integer between 1–9; and each of $Y^1$, $Y^2$, $Y^3$, and $Y^4$ is, independently of the others, a hydrogen (—H) group; an hydroxyl group (—OH); a methoxy group (—OCH$_3$); or a double bonded oxygen, suphur, or nitrogen group; and conjugating said first anthracycline to said second anthracycline through a linker group.

In preferred embodiments of the claimed methods, the first anthracycline is conjugated to the second anthracycline through a linker group joining their saccharide units. Such a linker group may be a phenyl group, a benzyl group, an aryl group, an alkyl group, a heterocycle, an aromatic heterocycle, a cycloalkane group, a cycloalkyl group, an alkylaryl group, an aryloalky group, an aryl group linked to another aryl group through an ester linkage an aryl group linked to an alkyl group with an ester linkage, an aryl group linked to another aryl group through an ether linkage and aryl group linked to an alkyl group through a thiolester linkage, an alkyl group linked to another alkyl group through an ester linkage, an alkyl group linked to another alkyl group through an ether linkage, an alkyl group linked to another alkyl group through an amino group, an aryl group linked to an alkyl through an amino group, an alkyl group linked to another alkyl group through a disulphide group, an aryl group linked to another alkyl group through a disulphide group, an aryl group linked to another aryl group through a disulphide group, an alkyl group linked to another alkyl group through a thioester linkage, an aryl group linked to an alkyl group through a polyester linkage, an aryl group linked to another aryl group through a polyester linkage, an alkyl group linked to another alkyl group through a polyamine linkage, an aryl group linked to an alkyl group through a polyamine linkage, an aryl group linked to another aryl through a polyamine linkage, an alkyl group linked to another alkyl group through a polythioester linkage, an aryl group linked to an alkyl group through a polythioester linkage, or an aryl group linked to another aryl through a polythioester linkage. In some preferred embodiments, the conjugation comprises adding a linker group to a solution of an anthracycline under conditions suitable to allow conjugation. For example, the linker group may be a halosubstituted aryl group. In some preferred embodiments, the halo-substituted aryl group is a halosubstituted xylene and in some particularly preferred embodiments, the halosubstituted xylene is α,α.dibromo xylene.

A preferred method of the invention comprises the steps of: (1) adding α α' dibromoxylene to a solution of anthracycline salt to obtain a bis anthracycline linked through a xylene unit; (2) removing extraneous solvent to obtain a crude bis anthracycline; (3) purifying the crude bis anthracycline; and (4) completing the synthesis by adding an acid to the purified bis anthracycline to obtain a salt of said bis anthracycline. In preferred embodiments the anthracycline solution is a daunorubicin solution. For example, the anthracycline solution can a 7-O-(4-amino-2,4,6 trideoxy-α-L-lyxo-hexopyranosyl) daunomycinone solution. In some embodiments of the method, the salt is formed using hydrochloric acid, sulfuric acid or nitric acid. In some embodiments of the method, the bis anthracycline formed is α α bis [3'N-daunorubicin)] p-xylene hydrochloride or α α bis 4'-N-(4'-amino-3'deamino-4'deoxy-3'-hydroxydaunorubicin) p-xylene hydrochloride.

The invention contemplates method of producing an anthracycline comprising adding electrophilically a saccharide to an anthracyclinone. In some embodiments, the saccharide is an L-isomer saccharide, for example a 4'amino glycal. In some preferred embodiments, the saccharide is a 4'amino glycal with the formula set forth in FIG. 12 wherein $R^{12}$ is SH, a halide group, amino group, nitro group, hydroxyl group, hydrogen, or a methoxy group and $R^{13}$ is SH, a halide group, amino group, nitro group, hydroxyl group, hydrogen, or a methoxy group. In other preferred embodiments, the saccharide is a 4'amino glycal with the formula set forth in FIG. 13 wherein $R^{14}$ is SH, a halide group, amino group, nitro group, hydroxyl group, hydrogen, or a methoxy group and $R^{15}$ is SH, a halide group, amino group, nitro group, hydroxyl group, hydrogen, or a methoxy group. or a saccharide of any description described elsewhere within the specification. In some preferred embodiments of the inventive methods of preparing an anthracycline, the anthracyclinone is daunomycinone or adriamycinone. A preferred method of this synthesis is further defined as comprising the steps of: (1) electrophilically adding 4'amino glycal to daunomycinone to obtain 7-O-(3-O acetyl 2,4,6, trideoxy-4-trifluoracetamide-α-L-lyxo hexopyranosyl) daunomycinone; (2) deacetylating said 7-O-(3-O acetyl 2,4,6, trideoxy-4-trifluoracetamide-a-L lyxo hexopyranosyl) daunomycinone to produce 7-O-( 2,4,6, trideoxy-4-trifluoracetamide-a-L lyxo hexopyranosyl) daunomycinone; (3) removing the trifluoracetamide group on the glycal of 7-O-( 2,4,6, trideoxy-4-trifluoracetamide-α-L lyxo hexopyranosyl) daunomycinone to yield 7-O-(4 amino-2,4,6 trideoxy-α-L lyxo hexopyranosyl) daunomycinone; (4) reacting 7-O-(4 amino-2,4,6 trideoxy-α-L lyxo hexopyranosyl) daunomycinone with an acid under conditions favorable for form a salt. In some embodiments of the method, the salt is formed using hydrochloric acid, sulfuric acid or nitric acid.

The invention also considers methods of treating a patient with cancer, comprising administering to the patient a therapeutically effective amount of the contemplated bis-anthracycline compounds and therapeutic kits comprising, in suitable container means, a pharmaceutically acceptable composition comprising the contemplated bis-anthracycline compounds.

Further, the invention considers bisintercalators comprising an anthracycline compound and another DNA intercalating agent. For instance, the other intercalator may be actinomycin, mitoxantrone, amascrine, dactinomycin.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF EXEMPLARY EMBODIMENTS

The present invention provides new and novel DNA intercalating agents. These agents are bisanthracyclines linked through the C-3' or C-4' sugar portions. These compounds show high activity against resistance. A novel approach of the invention produces compounds that are as active or more so than the parent compounds. Furthermore, the inventor's discovery is also for the design of effective DNA-binding bisanthracyclines as well as anthracyclines mixed with other intercalators and groove binders.

Figure 1:
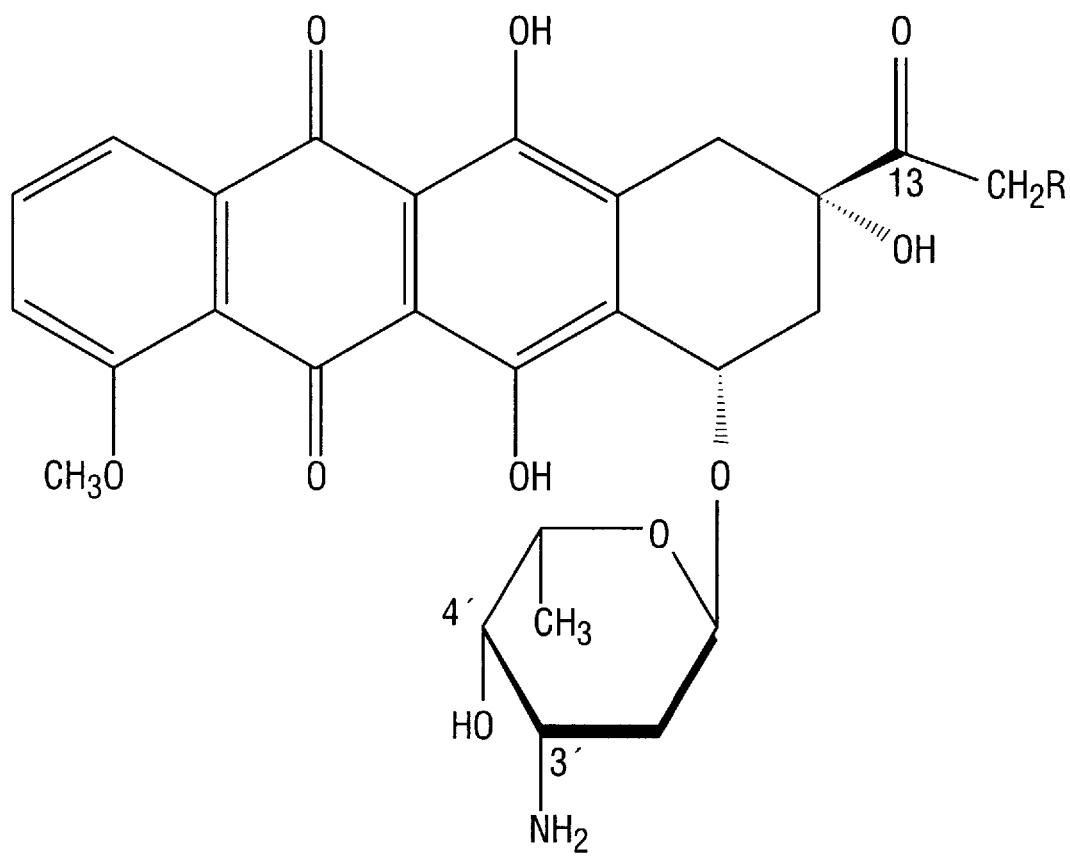
FIG. 1. Structures of daunorubicin and doxorubicin.
Figure 2:
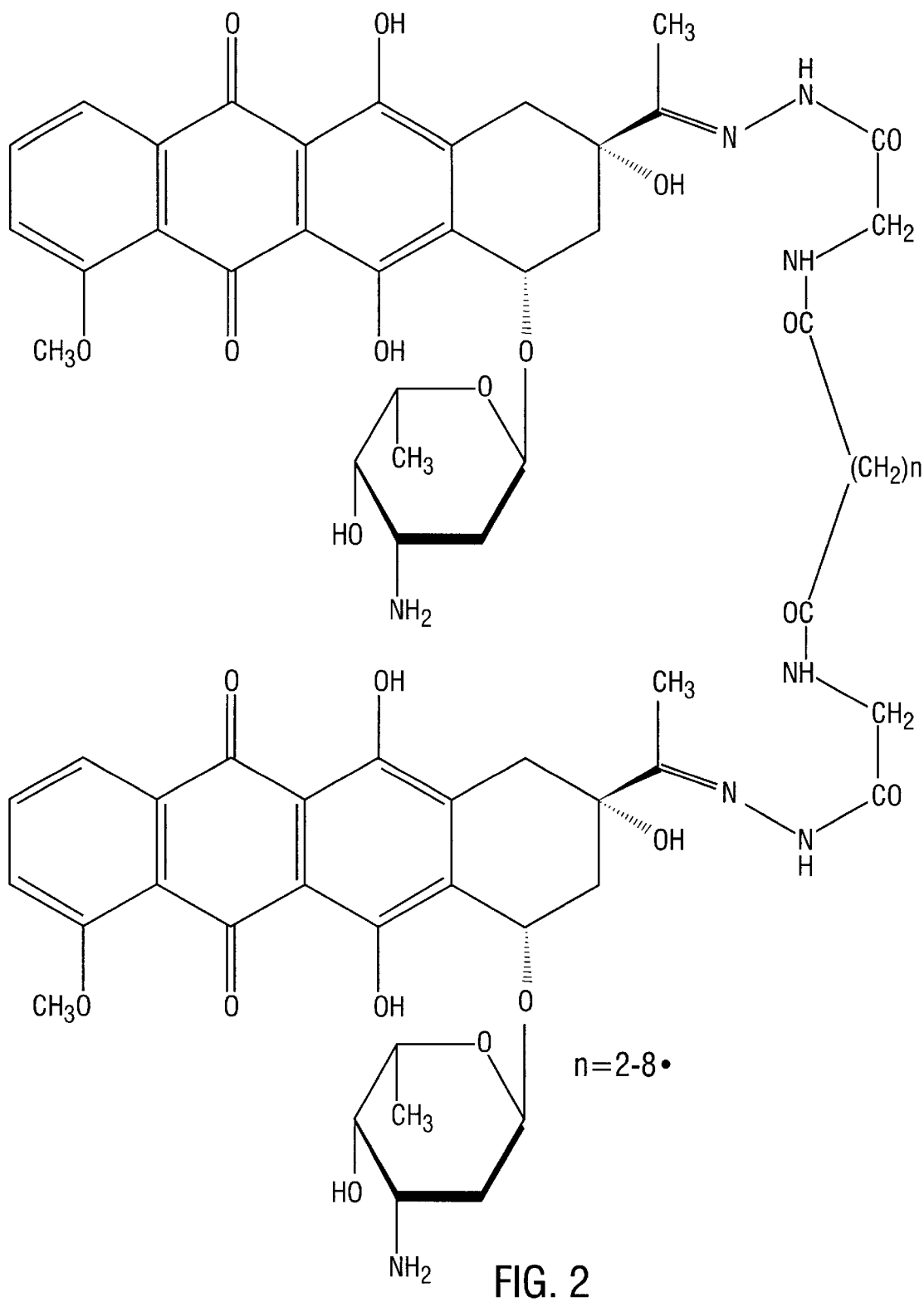
FIG. 2. Structures of bis-daunorubicins linked through C-13 position.

The anthracycline compounds have a tetracycline ring structure with sugars attached by a glycosidic linkage. Cytotoxic agents of this class have quinone and hydroquinone moieties that permit them to function as electron-accepting and electron donating agents. Doxorubicin and daunorubicin are examples of compounds of this class (FIG. 1). These compounds act by intercalating with DNA. Examples of exemplary anthracyclinones and anthracyclines are given in Table 1.

TABLE 1

List of Exemplary anthracyclinones and anthracyclines.

Anthracyclinones

Rhodomycinone
Isorhodomycinone
Pyrromycinone
4-Demethoxydaunomycinone
4-Demethoxyadriamycinone
Daunomycinone
Adriamycinone Anthracyclines Daunorubicin TABLE 1-continued List of Exemplary anthracyclinones and anthracyclines.

Doxorubicin
Pyrromycin
Isorhodomycine
Carminomycine
Doxorubicine 14-esters:     Doxorubicin 14-acetate
                            Doxorubicin 14-propionate
                            Doxorubicin 14-octanoate
                            Doxorubicine 14-benzoate
                            Doxorubicine 14-phenylacetate
4'-Epidaunorubicin
4'-Epidoxorubicin
4'-Iododaunorubicin
4'-Iododoxorubicin
4'-Deoxydaunorubicin
4'-Deoxydoxorubicin
3'-Hydroxydaunorubicine
3'-Hydroxydoxorubicin
4-Demethoxydaunorubicin
4-Demethoxydoxorubicin
4'-Epi-4-demethoxydaunorubicin
4'-Epi-4-demethoxydoxorubicin DNA intercalating agents are one of the most widely used classes of cancer chemotherapeutic agents currently used for the management of human cancers. Doxorubicin and daunorubicin are anthracycline antibiotics that intercalate with DNA. Although they differ slightly in chemical structure, daunorubicin has been used in the acute leukemias, whereas doxorubicin has broader activity against human neoplasms, including a variety of solid tumors. Several intercalators, including amsacrine (Denny, 1983), mitoxantrone (Cornbleet, 1984), and the anthrapyrazole DuP 941 (Talbot, 1991) have been reported to exhibit clinical anti-tumor activity. The DNA intercalator amonafide, a mono-naphthalimide, was reportedly shown to inhibit topoisomerase II and to result in intercalator-stabilized-topoisomerase II-DNA cleavable complex formation (Hsiang et al., 1989).

It is well known that doxorubicin binds preferentially to CGA or CGT (Chaires et al., 1990; Chaires et al., 1991; Pullman et al., 1989 incorporated herein by reference), sites such as:

CGA; CGT; GCA; GCT; ACG; TCG; AGC; TGC whereby the tetracycline part of the molecule intercalates with the bases and the sugar occupies a minor groove site. Bisintercalators of the present invention can be modified to recognize 3, 4, 5, 6, 9, 12 or more base pairs.

Figure 11:
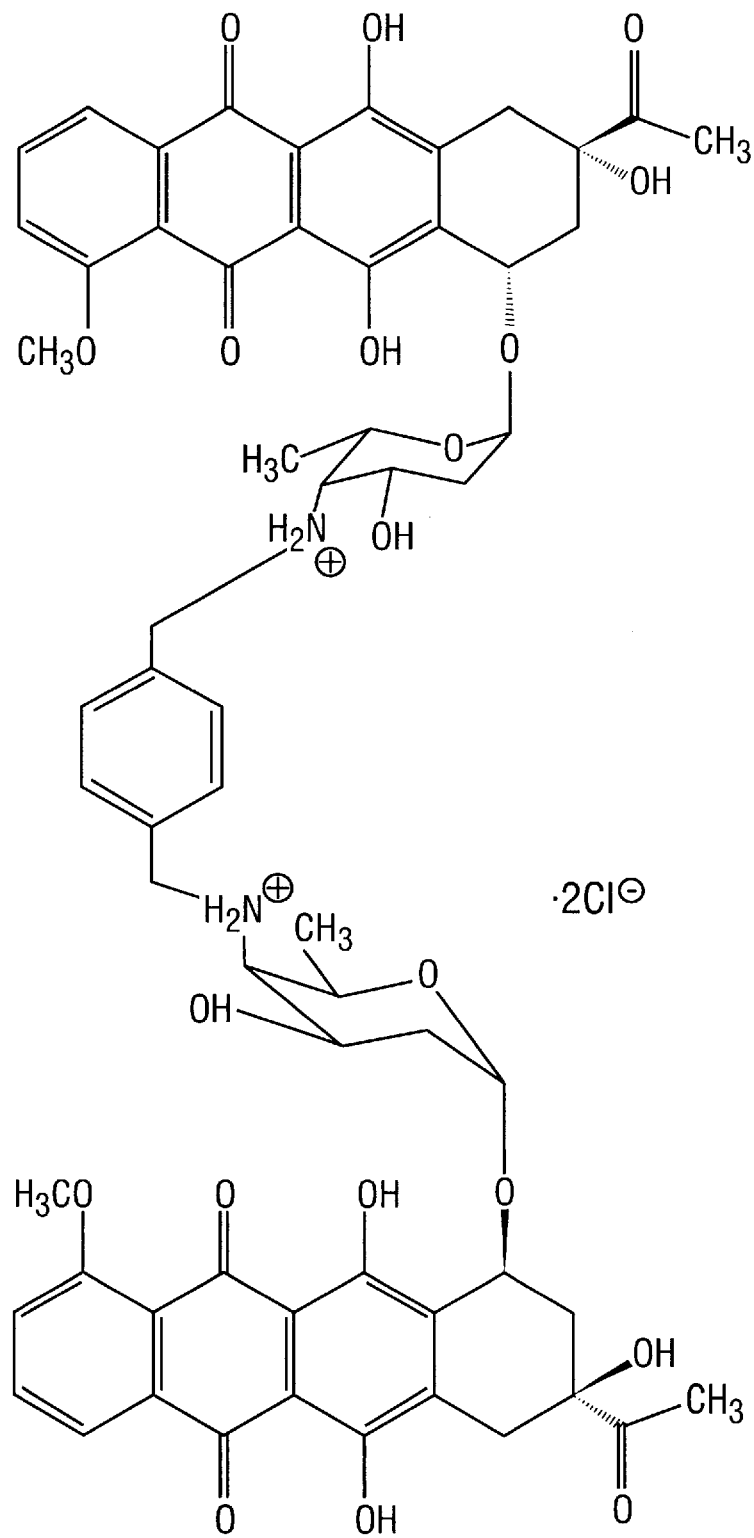
FIG. 11. Structure of WP 631
Figure 12:
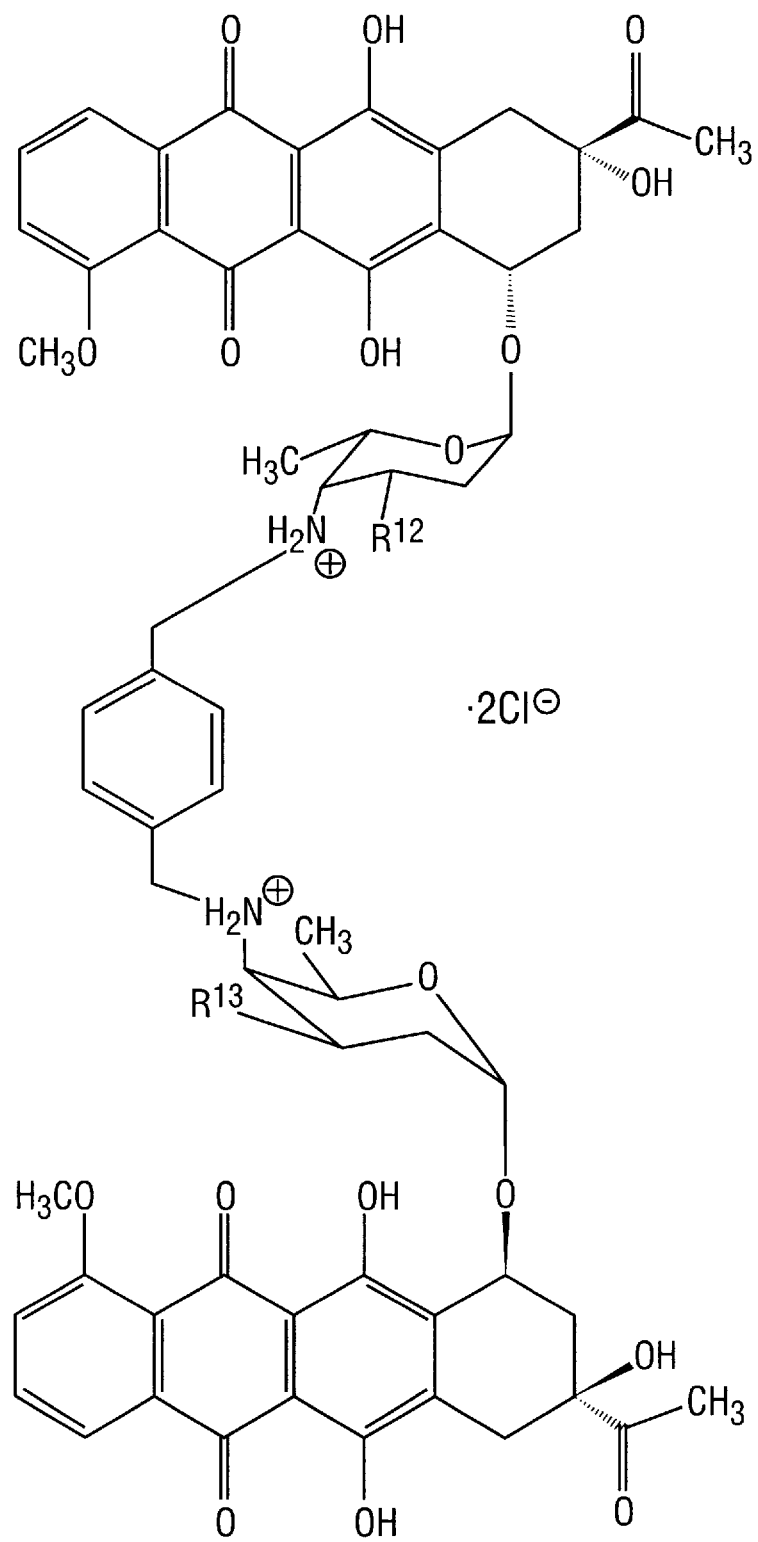
FIG. 12. A bis anthracycline linked through 4' carbon with modifications to the saccharide group wherein $R^{12}$ and $R^{13}$ are independently SH, a halide, amino, nitro, hydroxyl, hydrogen, or a methoxy group.
Figure 13:
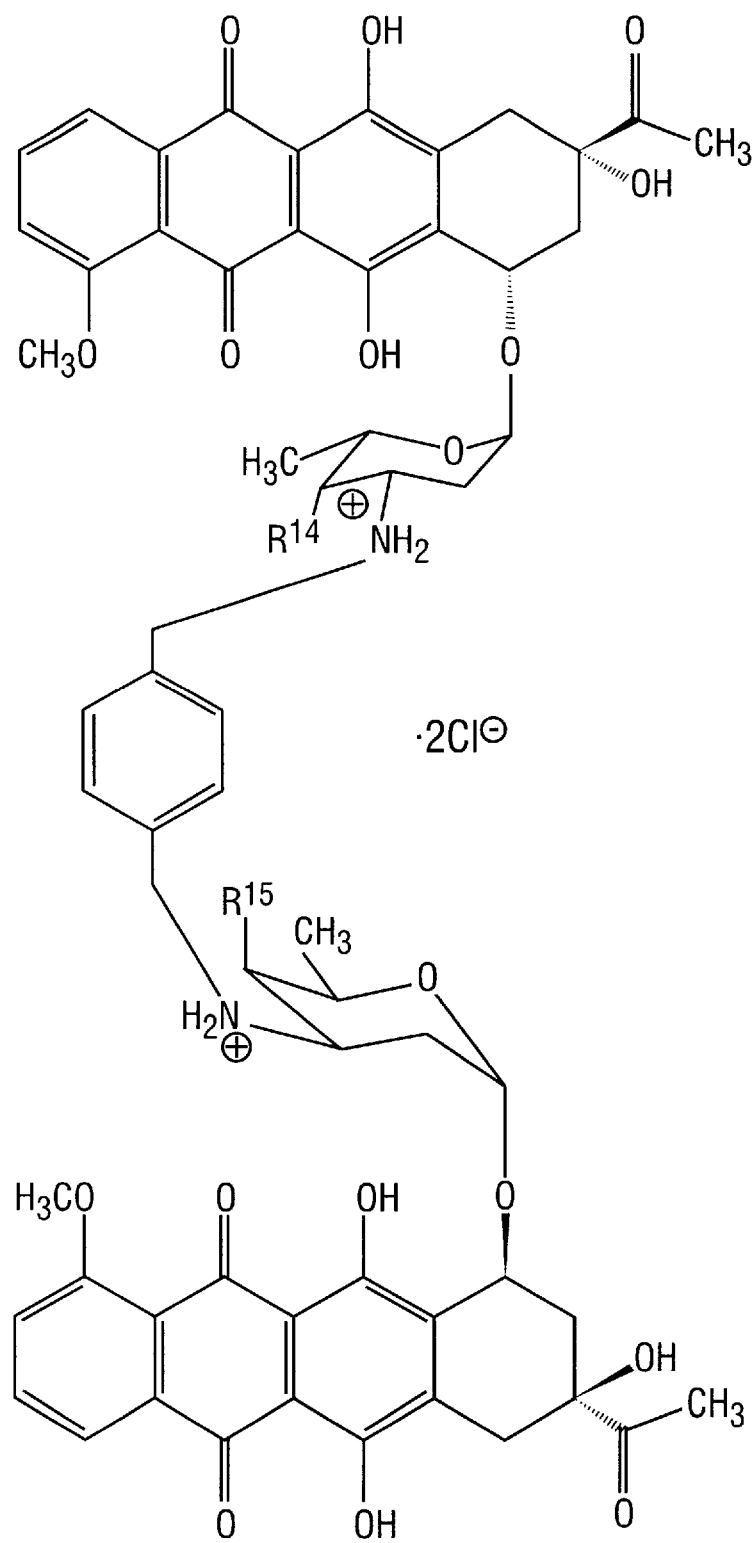
FIG. 13. A bis anthracycline linked through 3' carbon with modifications to the saccharide group wherein $R^{14}$ and $R^{15}$ are independently SH, a halide group, amino group, nitro group, hydroxyl group, hydrogen, methoxy group, or a saccharide of any description described elsewhere within the specification.
Figure 14:
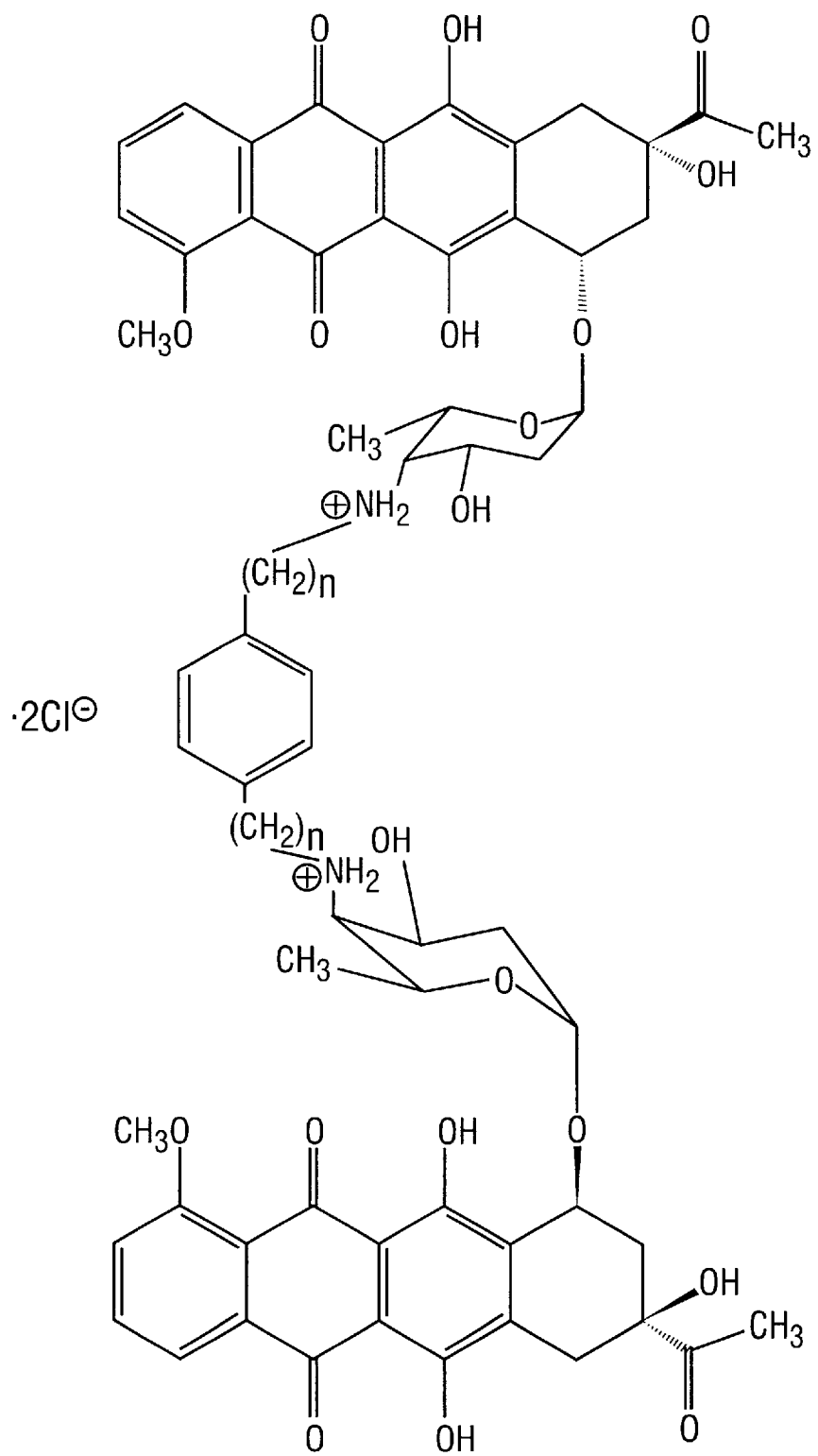
FIG. 14. Generalized structure of a bisanthracycline DNA intercalator of the present invention.
Figure 15:
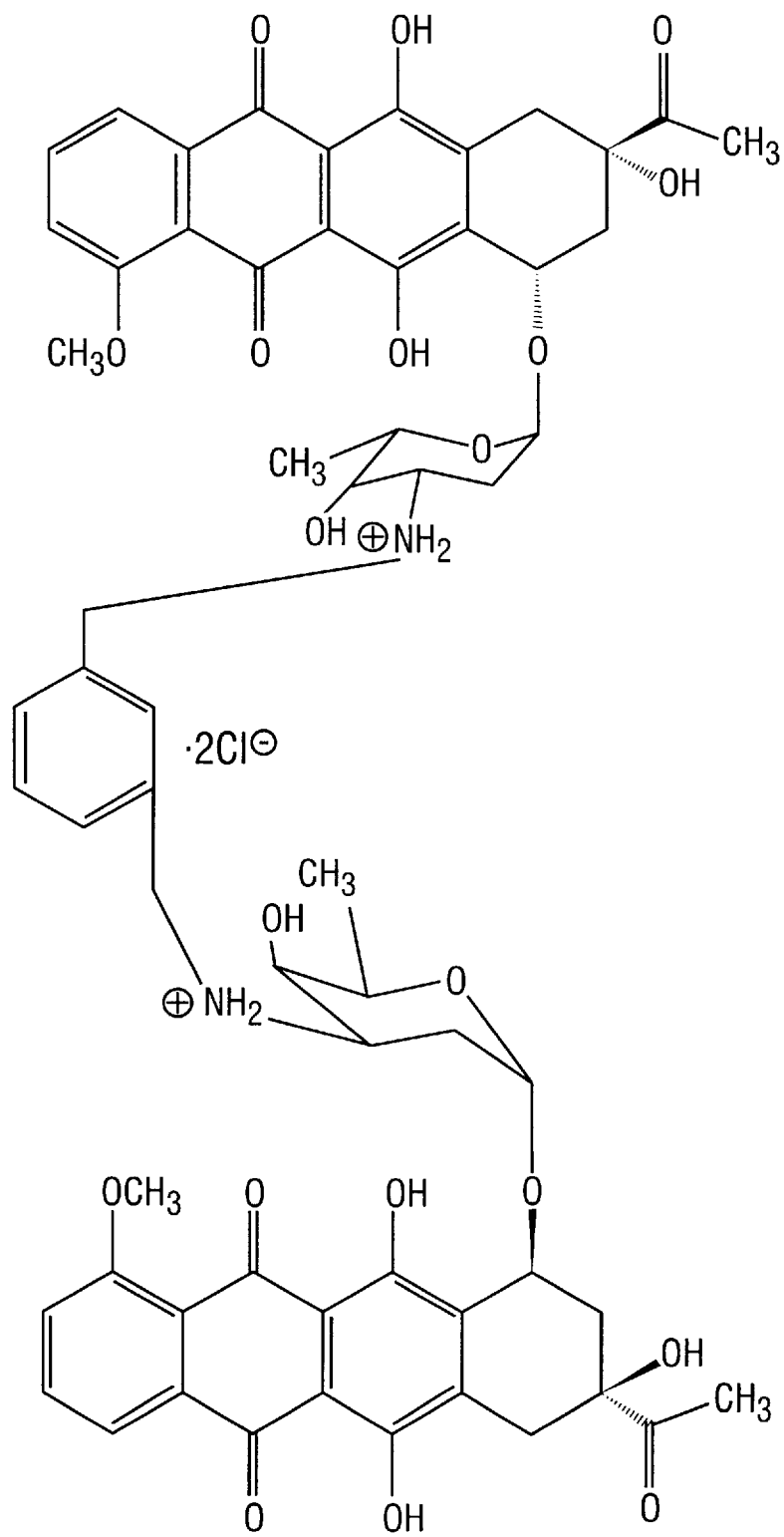
FIG. 15. Structure of WP 762
Figure 16:
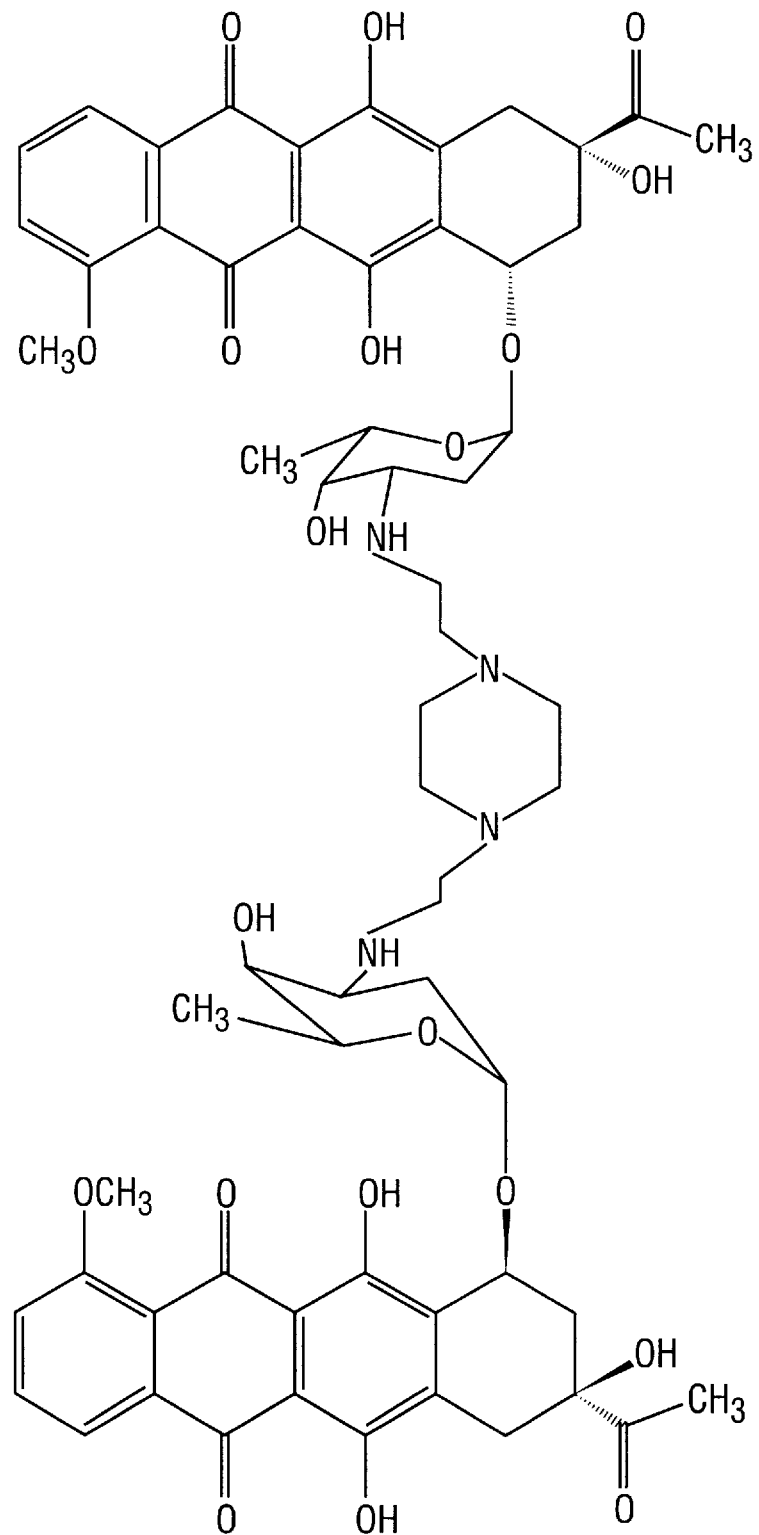
FIG. 16. Structure of WP 777
Figure 17:
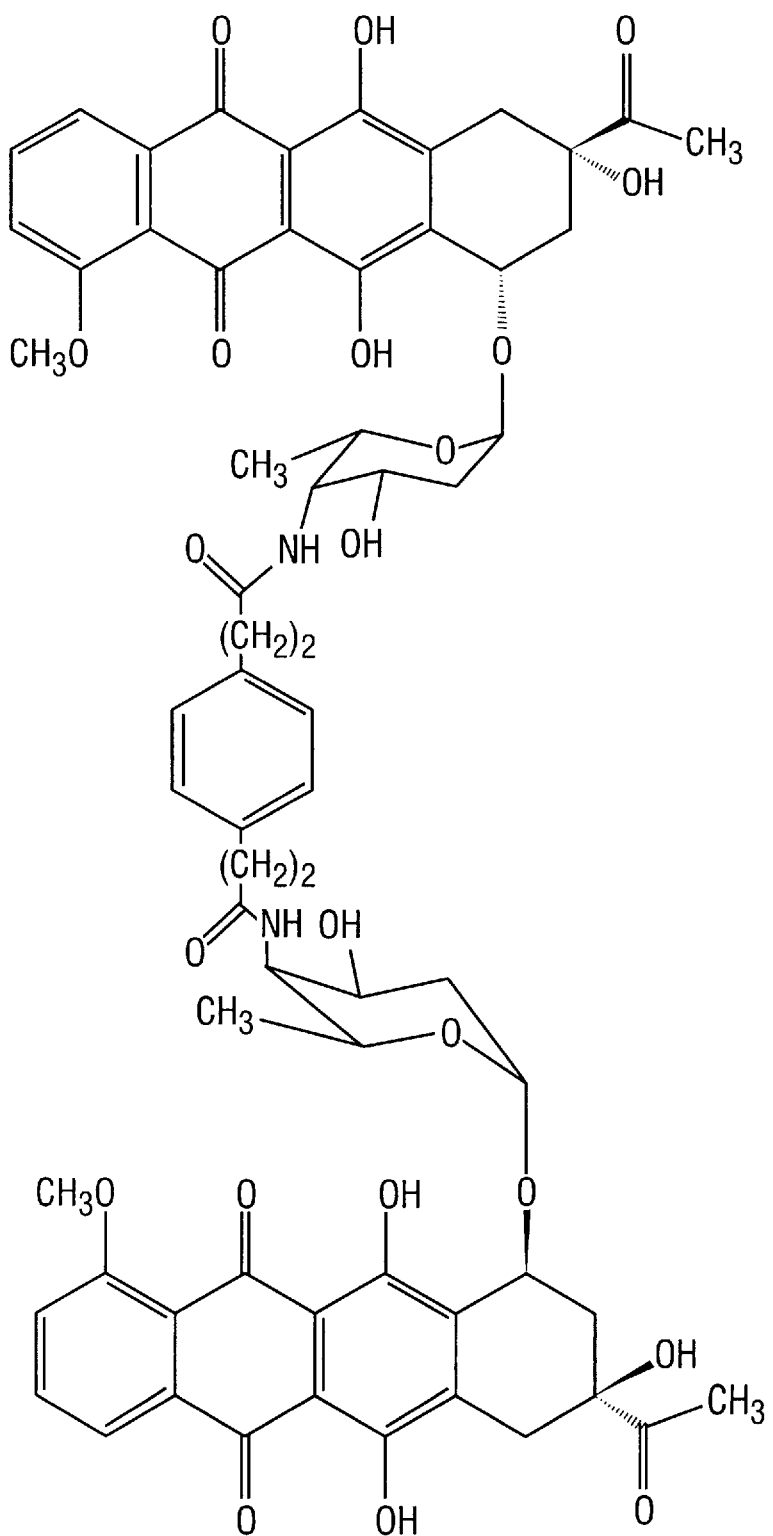
FIG. 17. Structure of WP 649
Figure 18:
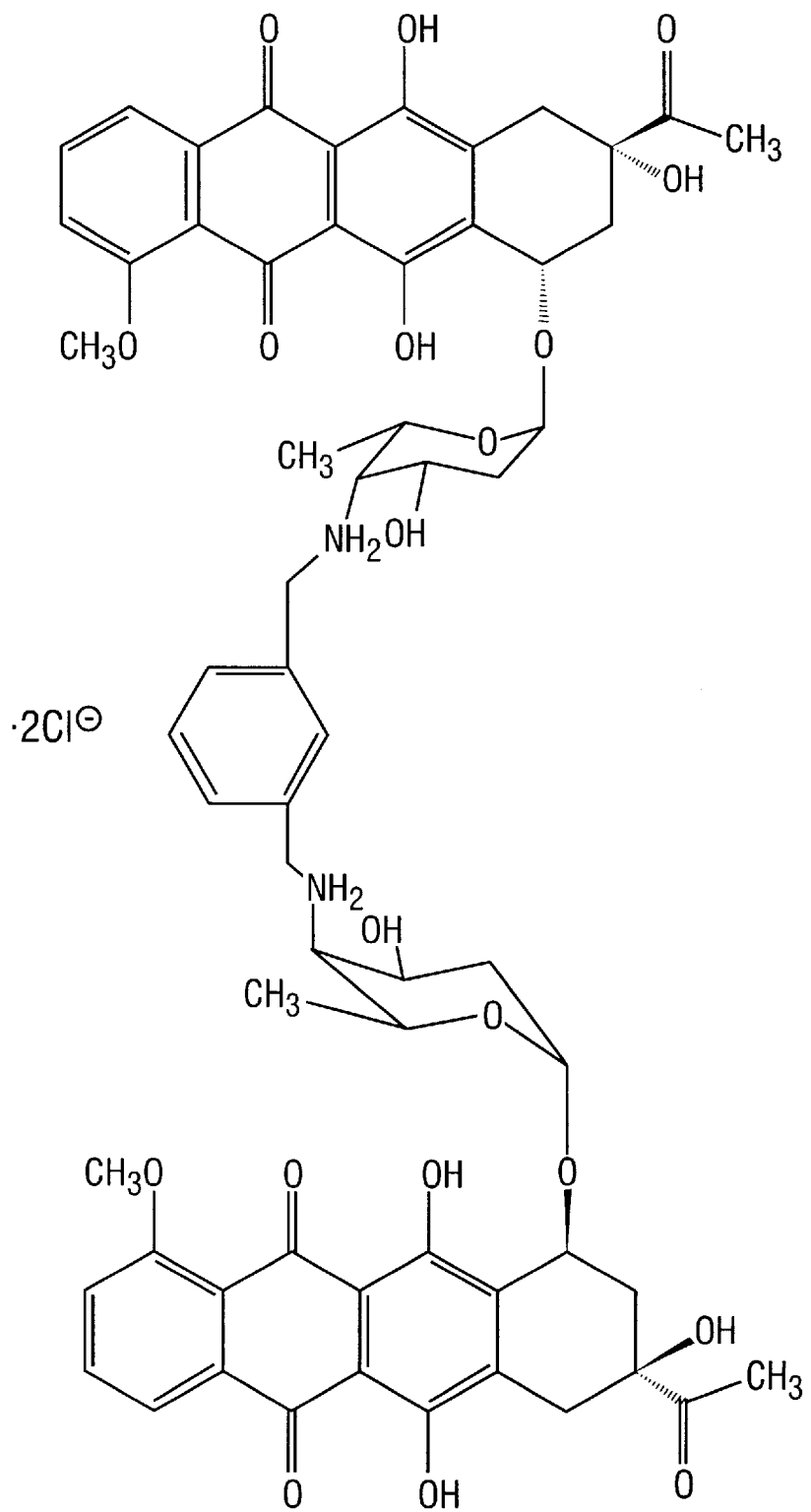
FIG. 18. Structure of WP 779

A particular embodiment of the present invention provides WP631 (FIG. 11) a rationally designed bisanthracycline that is intended to bisintercalate into DNA, with the concomitant advantages of enhanced DNA binding affinity and sequence selectivity over its monomeric counterpart, daunorubicin. These advantages will potentially make WP631 and the other bisintercalator disclosed herein (FIG. 10 to FIG. 19) improved anticancer agents, since the anthracycline antibiotics upon which these compounds are based have been successfully used in cancer chemotherapy for over three decades. The initial characterization of the DNA binding and biological activity of WP631 is described in the examples herein below.

WP631 and the other bisanthracyclines disclosed herein offer several advantages over previously synthesized bisintercalating anthracyclines (Wakelin, 1986; Henry and Tong, 1978; Phillips et al., 1992; Skorobogaty et al., 1988). In these earlier attempts, monomers were linked through the C13 and C14 positions. The primary advantage of WP631 and other novel bisanthracyclines of the present invention over these earlier designs is that the novel bisanthracyclines expand the inherent groove binding domain of the monomer for example daunorubicin in the case of WP631, creating a molecule with distinctive intercalating and groove binding functionalities.

Molecular modeling studies have shown that the linkers attached to the C13 and C14 positions do not fit into the DNA minor groove and consequently do not themselves add any favorable interactions with the DNA. In contrast, WP631 was designed and built to include intercalating and groove binding moieties that will both contribute to DNA binding affinity and specificity. The biological activity of previously synthesized bisanthracyclines was judged to be disappointing (Skorobogaty et al., 1988), in spite of increases in the DNA affinity and of the lifetimes of the complexes. In contrast, WP631 shows exciting biological activity, with an unexpected ability to apparently overcome multidrug resistance in the initial studies.

BIS-ANTHRACYCLINES

Figure 3:
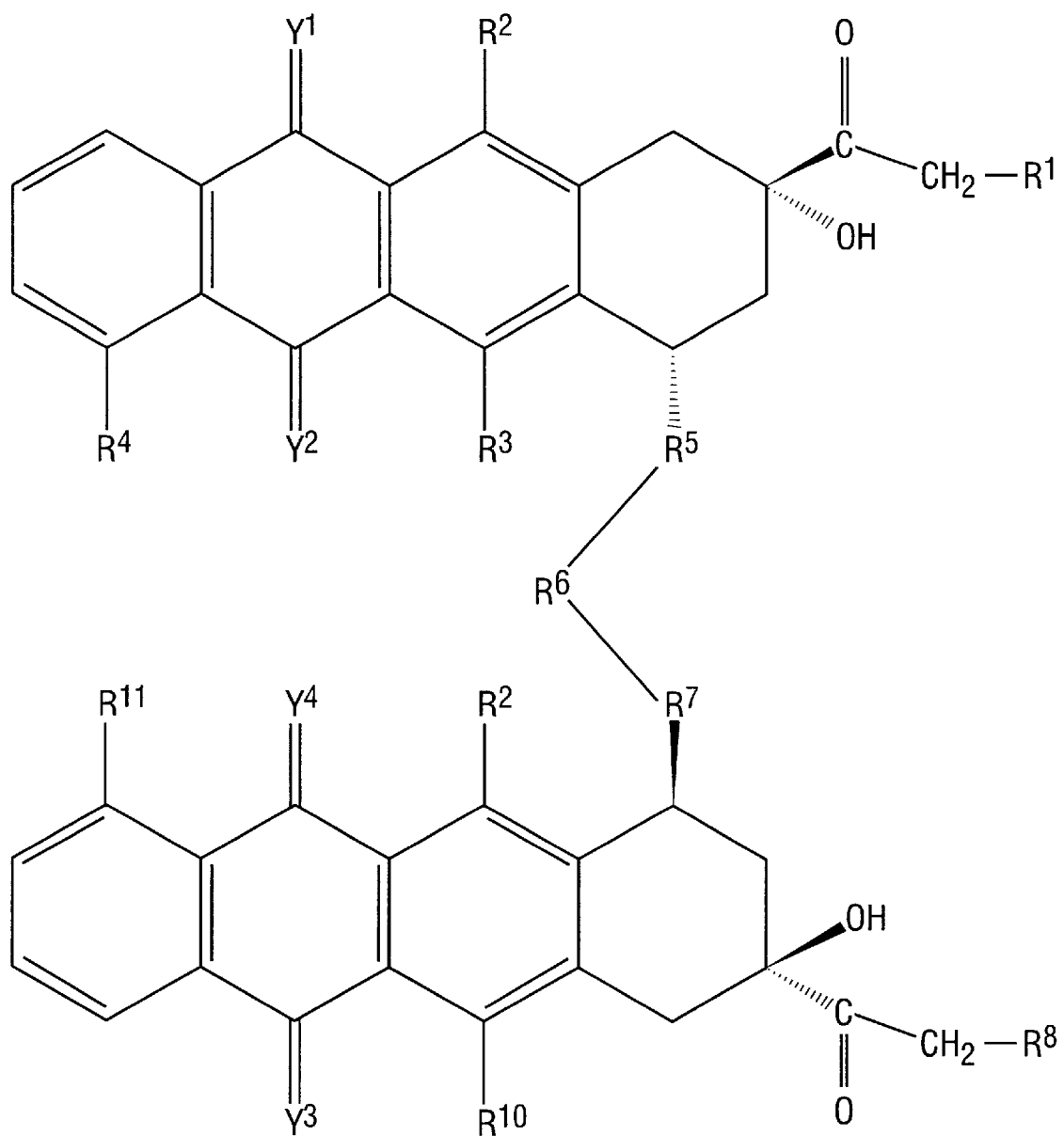
FIG. 3. Generalized structure of a bisanthracycline linked through the saccharide units.
Figure 4:
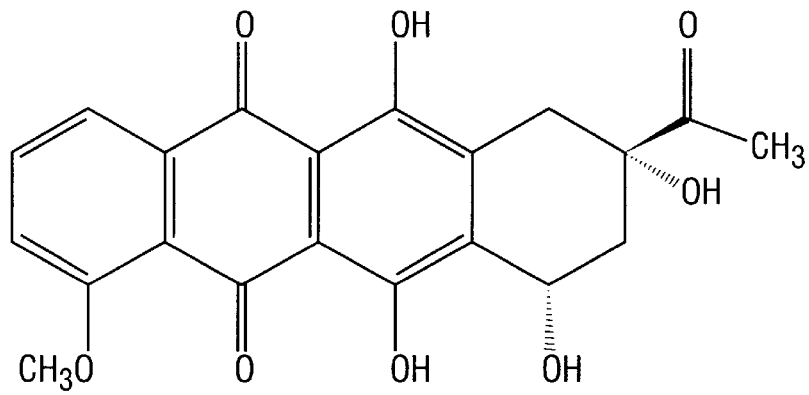
FIG. 4. Structure of daunomycinone (1).
Figure 5:
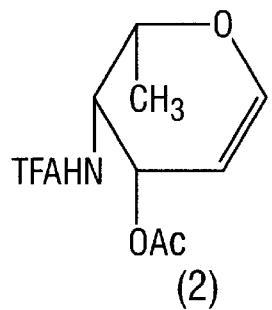
FIG. 5. Structure of 4-amino-glycal (2).
Figure 6:
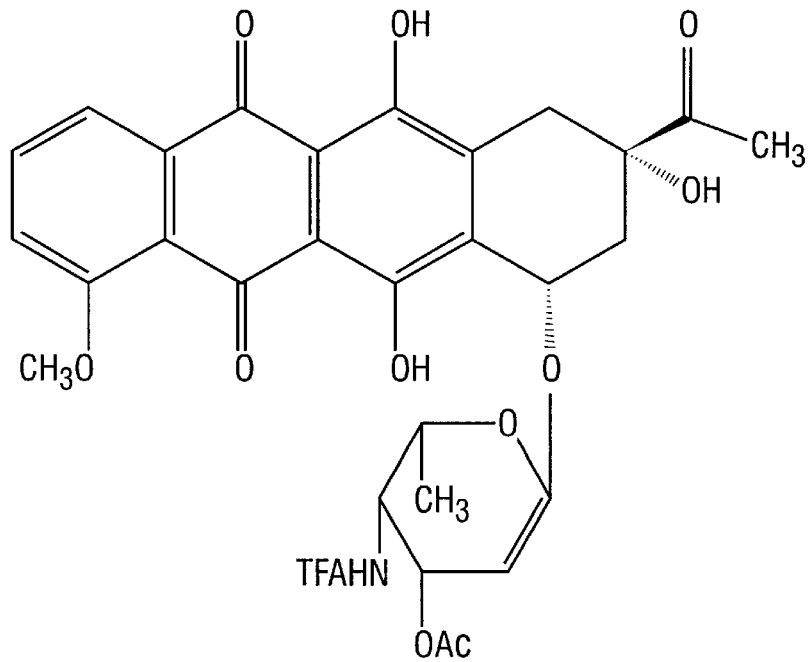
FIG. 6. Structure of 7-O-(3-O-acetyl-2,4,6-trideoxy-4-trifluoroacetamido-α-L-lyxo-hexopyranosyl) daunomycinone (3).
Figure 7:
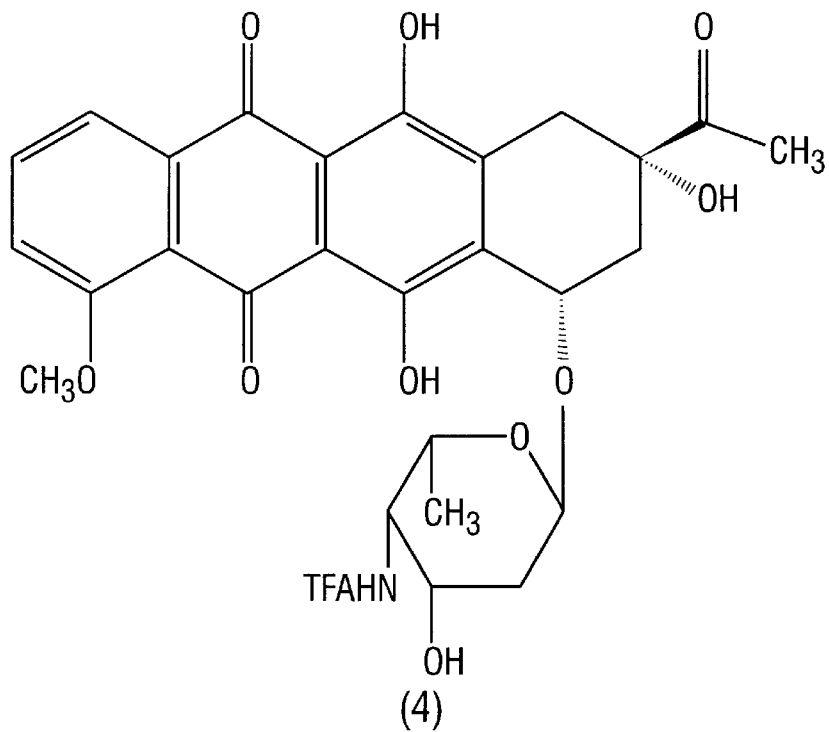
FIG. 7. Structure of 7-O-(2,4,6-trideoxy-4-trifluoroacetamido-α-L-lyxo-hexopyranosyl) daunomycinone.
Figure 8:
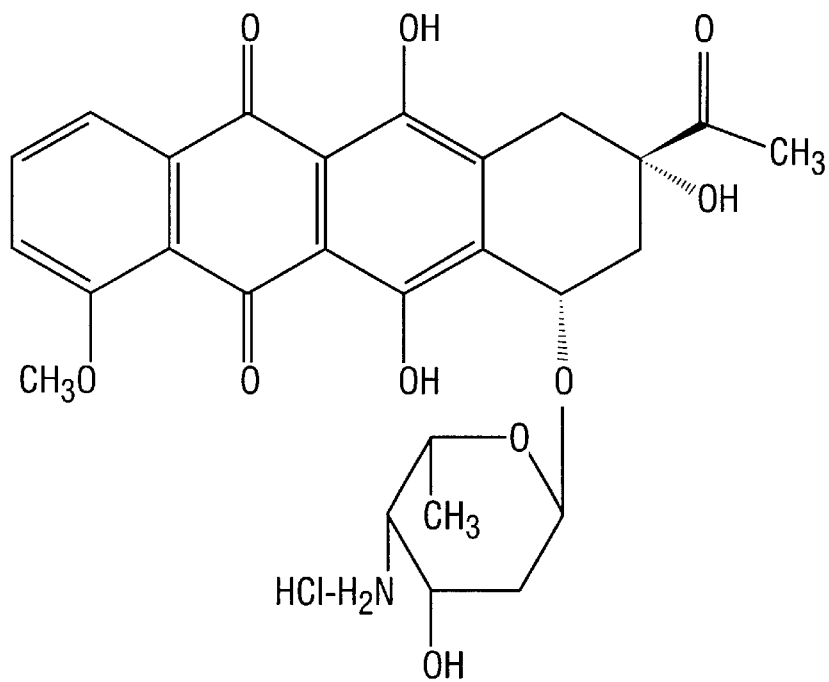
FIG. 8 Structure of 7-O-(4-amino-2,4,6-trideoxy-α-L-lyxo-hexopyranosyl) daunomycinone (WP608).
Figure 9:
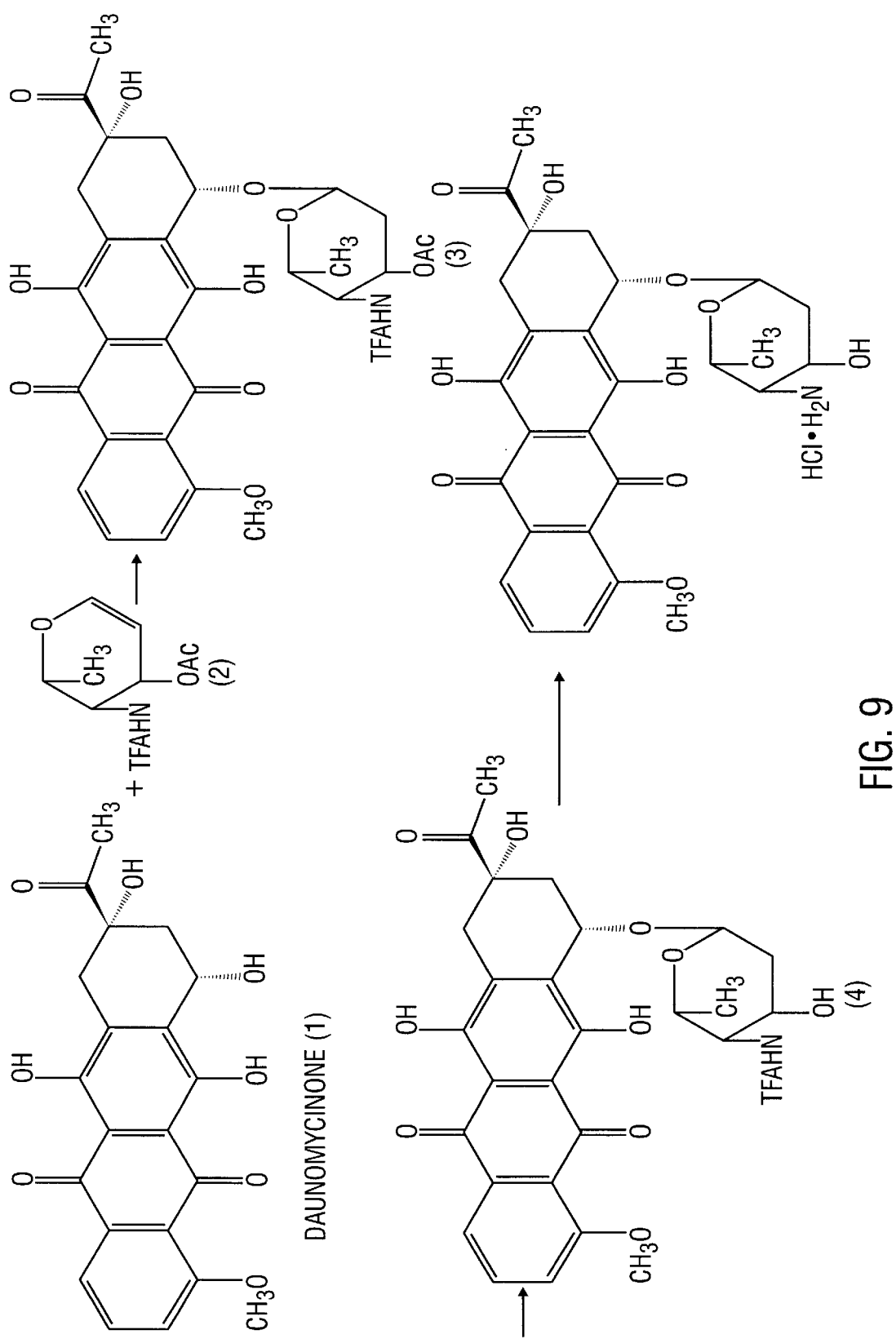
FIG. 9. Synthetic pathway of WP 608, where and 4-aminoglycal(2) and triphenylphosphine hydrobromide were added to anhydrous dichloromethane at room temperature to ultimately yield 7-O-(3-O-acetyl-2,4,6-trideoxy-4-trifluoroacetamido-α-L-lyxo-hexopyranosyl) daunomycinone (3). Compound 4 is 7-O-(2,4,6-trideoxy-4-trifluoroacetamido-α-L-lyxo-hexopyranosyl) daunomycinone. Compound 5 is 7-O-(4-amino-2,4,6-trideoxy-α-L-lyxo-hexopyranosyl) daunomycinone (WP608).
Figure 10:
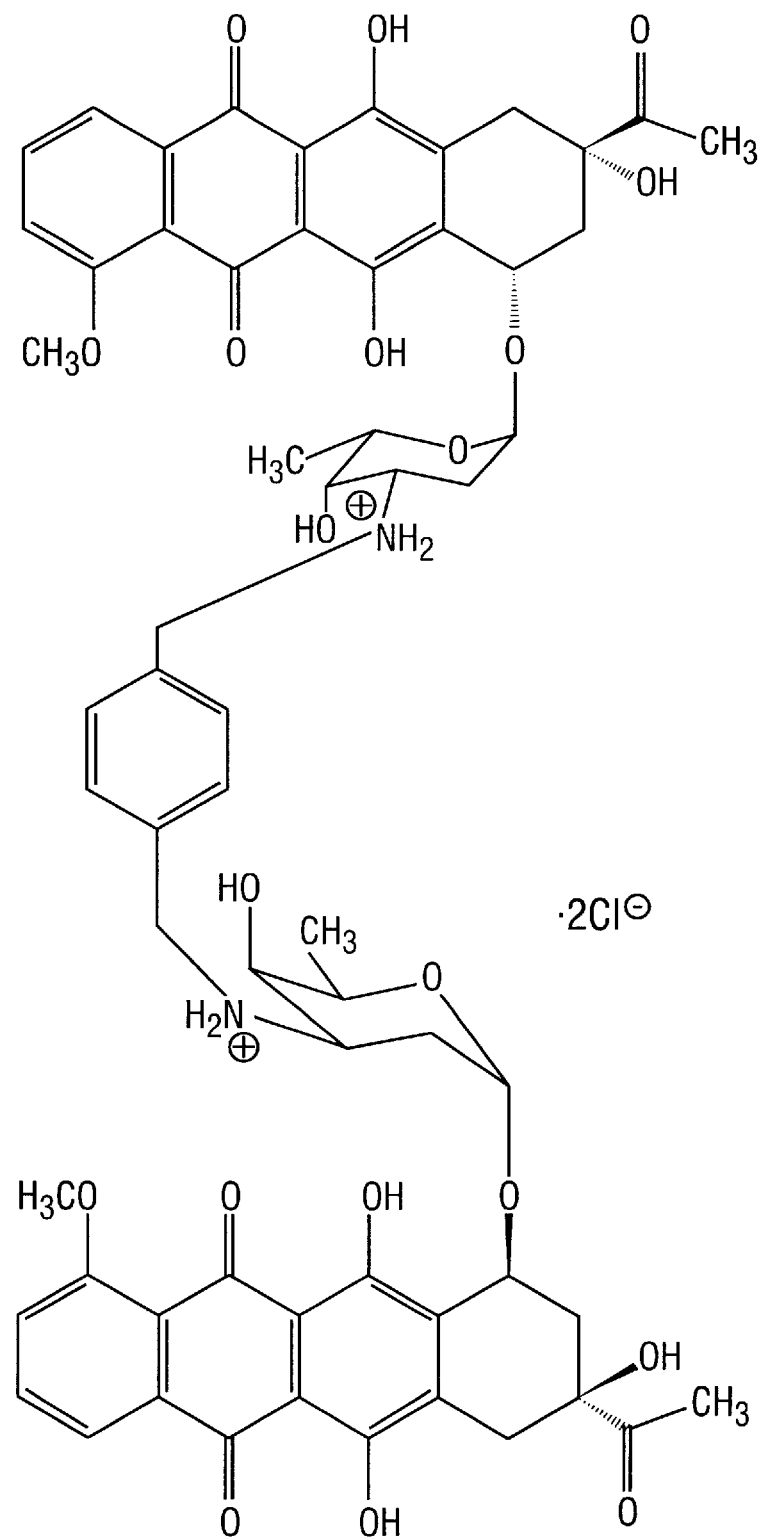
FIG. 10. Structure of WP 652

The generic formula for the compounds of this invention is given in FIG. 3.

$R^1$ and $R^8$ are, independently, alkyl, aryl, haloalkyl, formyl, acyl, hydroxyalkyl, oxyalkyl, oxyhydroxyalkyl, carboxy, carboxyalkyl, carboxyamide, carboxyamidoalkyl, aminoalkyl, amidealkyl, aryl group.

$R^2$–$R^4$ and $R^9$–$R^{11}$ are independently hydrogen, hydroxyl, methoxyl, or a double bonded oxygen moiety. $R^5$ and $R^7$ is a saccharide moiety $R^6$ may be a phenyl group, a benzyl group, an aryl group, an alkyl group, an aryl group linked to another aryl group through an ester linkage, an aryl group linked to an alkyl group with an ester linkage, an aryl group linked to another aryl group through an ether linkage and aryl group linked to an alkyl group with a thiolester linkage, an alkyl group linked to another alkyl group through an ester linkage, an alkyl group linked to another alkyl group through an ether linkage, an alkyl to alkyl linked through an amino group, an aryl to alkyl linked through an amino group. an alkyl alkyl group through a disulphide group, an aryl linked to an alkyl group through a disulphide group, an aryl linked to another aryl group through a disulphide group, an alkyl linked to another alkyl group through a thioester linkage, an aryl linked to an alkyl group through a polyester linkage, an aryl group linked to another aryl through a polyester linkage, an alkyl group linked to another alkyl group through a polyamine linkage, an aryl linked to an alkyl group through a polyamine linkage, an aryl group linked to another aryl through a polyamine linkage, an alkyl group linked to another alkyl group through a polythioester linkage, an aryl linked to an alkyl group through a polythioester linkage, an aryl group linked to another aryl through a polythioester linkage, Following long-standing patent law convention, the words "a" and "an", when used in the specification including the claims, denotes one or more.

"Alkyl" means alkyl groups, straight, branched or as cyclic isomers, with generally one to fifty, preferably one to thirty, more preferably one to ten, carbon atoms.

"Alkenyl" means alkenyl groups, straight, branched or as cyclic isomers, with generally two to fifty, preferably two to thirty, more preferably two to ten, carbon atoms, and with one to five or more double bonds, preferably one to five, more preferably one to three double bonds. "Hydroxyalkyl" means alcohols of alkyl groups. Preferred are hydroxyalkyl groups having one to twenty, more preferably one to ten, hydroxyls. "Hydroxyalkyl" is meant to include glycols and polyglycols; diols of alkyls, with diols of $C_{1-10}$alkyls being preferred, and diols of $C_{1-3}$alkyls being more preferred; and polyethylene glycol, polypropylene glycol and polybutylene glycol as well as polyalkylene glycols containing combinations of ethylene, propylene and butylene.

"Oxyalkyl" means alkyl groups as herein described with oxygen atoms, including ether or ester linkages. The number of repeating oxyalkyls within a substituent may be up to 200, preferably from 1 to 20, more preferably from 1 to 7, and most preferably is 2–3.

"Hydroxyalkoxy" means alkyl groups as described herein having ether or ester linkages, as well as hydroxyl groups, substituted hydroxyl groups, carboxyl groups, substituted carboxyl groups or the like.

"Carboxy" groups include carboxylic acids of the alkyls described herein as well as aryl carboxylic acids such as benzoic acid. "Carboxyalkyl" means alkyl groups having hydroxyl groups, carboxyl or amide substituted ethers, ester linkages, tertiary amide linkages removed from the ether or the like. Representative examples of "carboxyamides" include primary carboxyamides ($CONH_2$), and secondary (CONHR') and tertiary (CONR'R") carboxyamides where each of R' and R" is a functional group as described herein. "Carboxyamidoalkyl" means alkyl groups with hydroxyl groups, secondary or tertiary amide linkages or the like.

Representatives of useful amines include a primary, secondary or tertiary amine of an alkyl as described hereinabove.

"Aryl" may be a phenyl group, unsubstituted or substituted with a nitro, carboxy, sulfonic acid, hydroxy, oxyalkyl, or halide.

The term "saccharide" includes oxidized, reduced or substituted saccharides. Saccharides of this invention include, but are not limited to, ribose, arabinose, xylose, lyxose,, allose, altrose, glucose, mannose, fructose, gulose, idose, galactose, talose, ribulose, sorbose, tagatose, gluconic acid, glucuronic acid, glucaric acididuronic acid rhamnose, fucose, N-acetyl glucosamine, N-acetyl galactosamine, N-acetyl neuraminic acid, sialic acid. Derivatives of saccharides such as acetals, amines, and phosphorylated sugars; oligosaccharides; as well as open chain forms of various sugars, and the like.

"Carboxyamidoalkyl" means alkyl groups with secondary or tertiary amide linkages or the like. "Carboxyalkyl" means alkyl groups having hydroxyl groups, carboxyl or amide substituted ethers, ester linkages, tertiary amide linkages removed from the ether, or the like.

Figure 19:
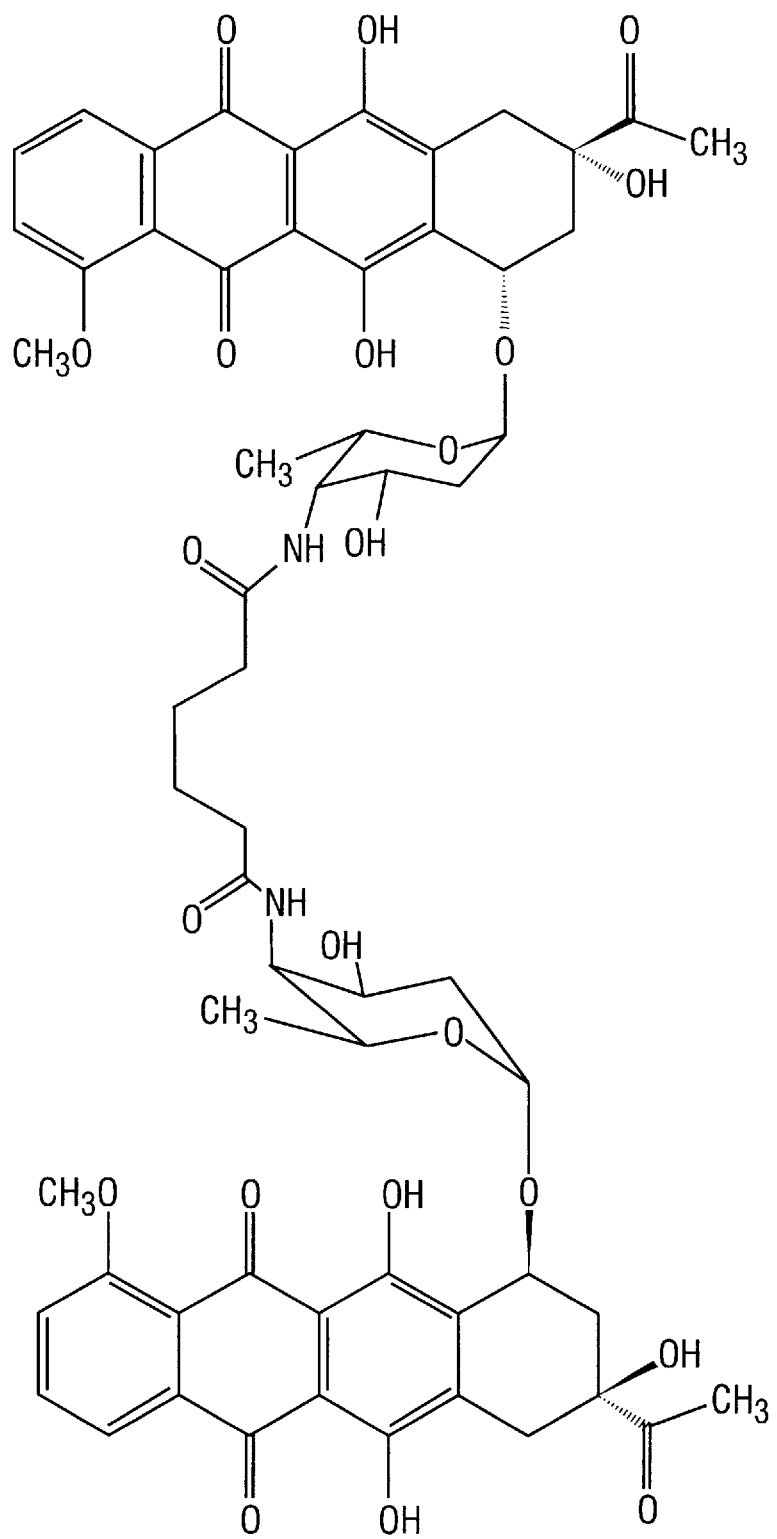
FIG. 19. Structure of WP 650

An individual skilled in the art of organic synthesis in light of the present disclosure is able to prepare a large variety of bisanthracyclines connected via sugar parts which are expected to have chemotherapeutic activities and may be used in the treatment of cancer and/or other diseases in which intercalating agents may be of used to cure disease. Preferred bisanthracyclines of the present invention are WP 631, WP 652, WP 762 (FIG. 15), WP 777 (FIG. 16), WP 649 (FIG. 17), WP 779 (FIG. 18) and WP 650 (FIG. 19). Each of these specific bisanthracyclines has been synthesized by the inventors and has been analyzed and its structure confirmed by NMR and elemental analysis. The methods of the present application enable one of skill in the art to synthesize these compounds and many other related compounds without undue experimentation.

The present discoveries may be utilized in conjunction with certain techniques that are well-known in the biological arts and that are further described in the following sections.

RATIONAL DRUG DESIGN

The rational, structure-based design of new DNA binding agents is an area of great current interest. Small synthetic molecules that could bind to DNA with high affinity and sequence specificity would be valuable tools for molecular biology and of potential medical use as chemotherapeutic agents against a variety of infections and diseases.

WP631 and related bisanthracyclines disclosed herein represent promising new compounds resulting from a novel approach to the structure-based design of DNA binding agents. Previous design efforts have focused largely on groove binding agents, whereas the compounds of the present invention, for example WP631, represent an attempt to combine the intercalation and groove binding motifs to yield a molecule that exploits the advantages of each binding mode.

Groove binding agents, as exemplified by netropsin and distamycin, in general bind selectively to runs of AT base pairs, in part because of the steric hindrance resulting from the protrusion of the N2 amino group of guanine into the minor groove. The "lexitropsins" were perhaps the first structure-based DNA binding agents to be synthesized and were designed to incorporate the reading of GC base pairs into the groove binding motif (Kopka et al., 1985; Lown, 1988; Lown, 1903). More recently, impressive progress for the recognition of DNA by groove binding pyrroleimidazole polyamides has been achieved (Mrksich el al., 1992; Trauger et al., 1996), an approach that exploits the side-by-side groove binding structural motif first described by Pelton and Wemmer (1989). Such agents bind to DNA with sequence-specific binding constants of $10^8$–$10^{10}$ $M^{-1}$ (Trauger et al., 1996). The strategy used to construct WP631 is complementary to these designs based on the groove binding mode.

Intercalators in general preferentially bind to CpG or GpC sites (Wilson, 1990), a property that might be exploited in the design of new agents. Linking GC specific intercalators by tethers that bind in the minor groove can expand the repertoire of available design elements. WP63 1 shows the promise of such an approach. While the sequence specificity of WP63 1 is not yet known, its affinity for DNA surpasses that of the polyamides (Trauger, 1996) and its biological activity shows outstanding promise in the initial studies described here.

In certain embodiments, the present invention concerns methods for identifying further bisanthracyclines, which are potential DNA intercalators and anticancer agents. It is contemplated that this screening technique will prove useful in the general identification of any compound that will serve the purpose of binding DNA in a manner similar to the exemplary bisanthrcyclines disclosed herein.

Useful compounds in this regard will not be limited to the bisanthracylines in FIG. 10 to FIG. 19. In fact, it may prove to be the case that the most useful pharmacological compounds for identification through application of the screening assay will be compounds that are further metabolized before they are therapeutically active. The active compounds may include fragments or parts of naturally-occurring compounds or may be only found as active combinations of known compounds which are otherwise inactive. However, prior to testing of such compounds, it will be possibly necessary to test a variety of candidates to determine which have potential.

The bisanthracyclines may be tested as effective intercalating agents using viscosity assays as described by Suh and Chaires (1995). Such assays are well known to those of skill in the art. In theory, for monointercalation, plots of the cubed root of the relative viscosity ($(\eta/\eta_0)^{1/3}$) versus the binding ratio (bound drug/DNA bp) ought to have a slope of 1.0. For bisintercalators, the slope is expected to be twice that observed for monointercalators, an expectation that has been verified for a variety of bisintercalating compounds (Wakelin, 1986). Thus in order to test the effectiveness of a candidate bisintercalator the viscosity of a DNA solution is measured according to assays well known to those of skill in the art (Suh and Chaires, 1995) and compared to the viscosity of a known intercalator such as daunorubicin. If the candidate substance is higher than that of the control monointercalator then the candidate substance is likely to be an effective bisintercalator.

In particular embodiments it will be necessary to determine the cytotoxic effect the bisintercalator candidates as effective anticancer agents. In these embodiments, the present invention is directed to a method for determining the ability of a candidate substance to inhibit the growth of cancer cells, the method including generally the steps of:

(a) obtaining a cancer cell responsive to DNA intercalators;

(b) admixing a candidate substance with the cell; and (c) determining the ability of the candidate substance to inhibit the growth of the cell Inhibition of growth of cancer cells can measured by the MTT assay. A significant inhibition in growth is represented by decreases of at least about 30%–40% as compared to uninhibited, and most preferably, of at least about 50%, with more significant decreases also being possible. Growth assays as measured by the MTT assay are well known in the art. Assays may be conducted as described by Mosmann et al., 1983; Rubinstein et al., 1990, Green et al., 1984 (incorporated herein by reference). Therefore, if a candidate substance exhibited inhibition in this type of study, it would likely be a suitable compound for use in the present invention.

Quantitative in vitro testing of the bisanthracylcines is not a requirement of the invention as it is generally envisioned that the agents will often be selected on the basis of their known properties or by structural and/or functional comparison to those agents already demonstrated to be effective. Therefore, the effective amounts will often be those amounts proposed to be safe for administration to animals in another context.

PHARMACEUTICAL COMPOSITIONS

The antitumor compounds of this invention can be administered to kill tumor cells by any method that allows contact of the active ingredient with the agent's site of action in the tumor. They can be administered by any conventional methods available for use in conjunction with pharmaceuticals, either as individual therapeutically active ingredients or in a combination of therapeutically active ingredients. They can be administered alone but are generally administered with a pharmaceutically acceptable carrier selected on the basis of the chosen route of administration and standard pharmaceutical practice.

Aqueous compositions of the present invention will have an effective amount of anthracycline to kill or slow the growth of cancer cells. Further the potential recognition of genes can be accomplished by the synthesis of bisanthracyclines with specific structures that allow for the recognition of specific parts of DNA. Such compositions will generally be dissolved or dispersed in a pharmaceutically acceptable carrier or aqueous medium.

The phrases "pharmaceutically or pharmacologically acceptable" refer to molecular entities and compositions that do not produce an adverse, allergic or other untoward reaction when administered to an animal, or human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredients, its use in the therapeutic compositions is contemplated. Supplementary active ingredients, such as other anti-cancer agents, can also be incorporated into the compositions.

In addition to the compounds formulated for parenteral administration, such as intravenous or intramuscular injection, other pharmaceutically acceptable forms include, e.g., tablets or other solids for oral administration; time release capsules; and any other form currently used, including cremes, lotions, mouthwashes, inhalents and the like.

A. Parenteral Administration

The active compounds will often be formulated for parenteral administration, e.g., formulated for injection via the intravenous, intramuscular, sub-cutaneous, or even intraperitoneal routes. The preparation of an aqueous composition that contains an anthracycline of the present invention as an active ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

In some forms, it will be desirable to formulate the novel compounds in salt form, generally to improve the solubility and bioavailability and to provide an active drug form more readily assimilated. As used herein, the term "pharmaceutically acceptable salt" refers to compounds which are formed from acidifying a solution of the compound of formula in FIG. 3 with suitable physiologically tolerated acids. Suitable physiologically tolerated acids are organic and inorganic acids, such as hydrochloric acid, sulfuric acid, phosphoric acid, acetic acid, citric acid, oxalic acid, malonic acid, salicylic acid, maleic acid, methane sulfonic acid, isothionic acid, lactic acid, gluconic acid, glucuronic acid, amidosulfuric acid, benzoic acid, tartaric acid and pamoaic acid. Typically, such salt forms of the active compound will be provided or mixed prior to use.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

The active compounds may be formulated into a composition in a neutral or salt form. Pharmaceutically acceptable salts, include the acid addition salts and which are formed with inorganic acids such as, for example, hydrochloric or phosphoric acids, or such organic acids as acetic, oxalic, tartaric, mandelic, and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In certain cases, the therapeutic formulations of the invention could also be prepared in forms suitable for topical administration, such as in creams and lotions. These forms may be used for treating skin-associated diseases, such as various sarcomas.

Upon formulation, solutions will be administered in a manner compatible with the dosage formulation and in such amount as is therapeutically effective. The formulations are easily administered in a variety of dosage forms, such as the type of injectable solutions described above, with even drug release capsules and the like being employable.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

B. Oral Administration

In certain embodiments, active compounds may be administered orally. This is contemplated for agents which are generally resistant, or have been rendered resistant, to proteolysis by digestive enzymes. Such compounds are contemplated to include all those compounds, or drugs, that are available in tablet form from the manufacturer and derivatives and analogues thereof.

For oral administration, the active compounds may be administered, for example, with an inert diluent or with an assimilable edible carrier, or they may be enclosed in hard or soft shell gelatin capsule, or compressed into tablets, or incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

Upon formulation, the compounds will be administered in a manner compatible with the dosage formulation and in such amount as is therapeutically effective. The formulations are easily administered in a variety of dosage forms, such as those described below in specific examples.

The following examples arc included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLE I

Synthesis of bis-intercalators

Materials and methods:

Thin layer chromatography (TLC) was performed on precoated plastic sheets (0.2 mm) of silica gel 60 F-254 (E. Merck AG, Darmstadt, West Germany); compounds were detected by spraying the plates with 10% sulfuric acid with subsequent heating. Melting points were determined with a Buchi 530 apparatus and are uncorrected. NMR spectra were recorded for solution in chloroform-d (internal standard Me$_4$Si) and for WP608 in pyridine-d$_5$ with a Bruker 400 MHz and 500 MHz spectrometer. Elemental analysis was performed by Atlantic Microlab Inc., Atlanta, Ga., U.S.A.

1. Synthesis of bis-daunorubicin linked through the 3'-amino group.

The inventors synthesized bis-daunorubicin WP630 and its hydrochloride WP631 bridged through the 3'-amino group by using α,α'-dibromo-p-xylene as a linker (FIG. 3).

α,α'-Bis-[3'-N-(daunorubicin)]-p-xylene hydrochloride (WP631)

Daunorubicin hydrochloride (282 mg, 0.5 mmol) was dissolved in mixture of DMF and CH$_2$Cl$_2$ (1:1 v/v) (6 mL). Then, Na$_2$CO$_3$ (100 mg) and α,α-di-bromo-p-xylene (68.7 mg 0.26 mmol) were added. The reaction mixture was stirred at room temperature for 20–28 hr. The progress of the reaction was monitored by TLC (chloroform: methanol : NH$_4$OH aq 86:13:1).

After reaction was complete, the reaction mixture was diluted with dichloromethane (100 mL) and poured into the water (100 mL). Organic layer was separated and washed with water until neutral, then dried over anhydrous Na$_2$SO$_4$ and evaporated under diminished pressure. Crude product was purified by column chromatography (Silicagel 60, 230–400 mesh, Merck, eluents: CHCl$_3$, then CHCl$_3$:MeOH 98:2 and 95:5). Final product was isolated as free amine (WP630) and precipitated from CH$_2$Cl$_2$:hexane to give a red solid (178 mg, 0.153 mmol) in 61.5% yield. Elemental analysis for C$_{62}$H$_{64}$O$_{20}$N$_2$·H$_2$O: Calc: C 63.37, H 5.66, N 2.31; Found: C 63.37, H 5.66, N 2.3. $^1$H—NMR (CDCl$_3$): δ13.95 (s, 1H, OH), 8.01 (d, 1H, J=7.67 Hz, H-3), 7.77 (app. t, 1H, J$_{1,2}$=J$_{2,3}$=7.94 Hz, H-2), 7.38 (d, 1H, J=8.53 Hz, H-1), 7.18 (s, 2H, p-xylene), 5.50 (d, 1H, J=3.36 Hz, H-1'), 5.28 (bs, 1H, H-7), 4.66 (s, 1H, 9—OH), 4.07 (s, 3H, OCH3), 4.05 (q, 1H, J=6.25 Hz, H-5'), 3.77 (d, 1H, J=12.78 Hz, CH$_2$ from p-xylene spacer), 3.63 (d, 2H, J=12.53 Hz, CH$_2$ from p-xylene and H-4'), 3.22 (d, 1H, J=18.82 Hz, H-10), 2.96 (d, 1H, J=18.79 Hz, H-10), 2.98–2.93 (m, 1H, H-3), 2.41 (s, 3H, H-14), 2.37 (d, 1H, J$_{8a,8e}$=14.74 Hz, H-8e), 2.09 (dd, 1H, J$_{8a,8e}$=14.87 Hz, J$_{7,8a}$=4.1 Hz, H-8a), 1.76 (td, 1H, J$_{2'a,2'e}$=J$_{2'a,3'}$=13.1 Hz, J$_{1',2'a}$=3.8 Hz, H-2'a), 1.68 (dd, 1H, J2'e,3'= 4.7 Hz, J$_{2'a,2'e}$=13.18 Hz, H-2e'), 1.37 (d, 3H, J$_{5'6'}$=6.65 Hz, H-6').

Amine WP630 was suspended in MeOH (2 mL). Then 1N dry HCl in MeOH was added (to pH 4) and followed by an excess of diethyl ether to precipitate hydrochloride of WP630. Red solid was washed with ether until neutral pH, then dried to give analytically pure WP631 (170 mg, 0.138 mmol, 55.3%—yield calculated from daunorubicin): mp 160°–170° C. with decomposition; [α]D$^{29}$ 184.7° (c 0.05, CHCl$_3$ CH$_3$OH 1:1). Elemental analysis for C$_{62}$H$_{65}$ClN$_2$O$_{20}$·4×H$_2$O: Calc: C 57.19, H 5.73, Cl 5.45N 2.15; Found: C 57.15, H 5.71, Cl 5.51, N 2.07.

2. Synthesis of 4'-amino-3'-hydroxy-daunorubicin and its 4'-amino-linked bis-4'-aminodaunorubicin WP652.

4'-Aminodaunorubicin, a highly active regioisomer of daunorubicin, was a good substrate for a model 4'-bridged dimer. Synthesis of such a dimer allowed the inventors to compare the 3'-linked and 4'-linked bisanthracyclines.

7-O-(3-O-acetyl-2,4,6-trideoxy-4-trifluoroacetamido-α-L-lyxo-hexopyranosyl) daunomycinone (Priebe, 1995).

Daunomycinone (1) (500 mg, 1.26 mmol), 4-amino glycal (2) (673 mg, 2.52 mmol), and triphenyl phosphine hydrobromide (83.3 mg, 0.24 mmol) were added to anhydrous dichloromethane (25 mL) and stirred at room temperature. The progress of the reaction was controlled by TLC (toluene:acetone, 3:2). After 12 hours, another portion of glycal 2 (146.5 mg) was added, and the mixture was stirred another 24 hours. After that time, no daunomycinone in the reaction mixture was detected. The reaction mixture was then diluted with dichloromethane (75 mL), washed with water (3×25 mL), and dried over anhydrous Na$_2$SO$_4$. Next, the drying agent was filtered and solvent evaporated under diminished pressure. The obtained red solid was purified by column chromatography on silica gel using first dichloromethane:hexane (9:1), dichloromethane and then dichloromethane:acetone (10:1) as eluent. The final product, 7-O-(3-O-acetyl-2,4,6-trideoxy-4-trifluoroacetamido-α-L-lyxo-hexopyranosyl) daunomycinone (3), was then purified by precipitation from dichloromethane:hexane. Yield 750.8 mg (89.6%): m.p. 149°–150° C., [α]$_D$–216.9° (c 0.02, chloroform:methanol 1:1). Elemental analysis for C$_{31}$H$_{30}$F$_3$NO$_{12}$: Calc: C 55.94, H 4.54, N 2.10; Found: C 55.86, H 4.59, N 2.04.

7-O-(2,4,6-trideoxy-4-tifluoroacetamido-α-L-lyxo-hexopyranosyl) daunomycinone (4).

Fully blocked compound 3 (61.6 mg. 0.0925 mmol) was dissolved in 4 mL of the mixture of dichloromethane and methanol (2:1). Then K$_2$CO$_3$ was added, and the mixture was stirred at room temperature and monitored by TLC (toluene:acetone 3:2). After the reaction was completed, dichloromethane was added and solid potassium carbonate was filtered off. The filtrate was washed with water and dried over Na$_2$SO$_4$. Subsequent filtration and evaporation of solvents under diminished pressure gave crude 7-O-(2,4,6-trideoxy-4-trifluoroacetamido-α-L-lyxo-hexopyranosyl) daunomycinone (Priebe, 1995), which was purified by column chromatography on a silica gel (dichloromethane, followed by dichloromethane:acetone 100:5) and then crystallized from dichloromethane:hexanes. Yield 53.3 mg (92.4%); m.p. 154°–156° C.; [α]D–42°(c=0.02, methanol:chloroform 1:1). Elemental analysis for C$_{29}$H$_{28}$F$_3$NO$_{11}$·1.5 H$_2$O: Calc: C 55.94, H 4.54, N 2.10; Found: C 55.86, H 4.59, N 2.04.

7-O-(4-amino-2,4,6-trideoxy-α-L-lyxo-hexopyranosyl) daunomycinone (WP608).

Compound 4 (491 mg) was dissolved in dichloromethane (10 mL). Then, 1 N NaOH (3 mL) was added. The mixture was stirred at room temperature for 20 min. Next, 1N HCl (3 mL) was added and the mixture was diluted with dichloromethane (25 mL), and water (25 mL) was added. The organic layer was separated. To the water solution, solid NaHCO$_3$ was added, followed by methanol (10 mL). The obtained solution was extracted with chloroform until the water layer was almost colorless. Combined organic extracts were combined and dried over Na$_2$SO$_4$. The drying agent and solvents were removed, and the residue was dissolved in methanol (3 mL). Then, a 1.1 equivalent of dry HCl in MeOH was added, and the final product was precipitated with diethyl ether. Hydrochloride of 7-O-(4-amino-2,4,6-trideoxy-α-L-lyxo-hexopyranosyl)daunomycinone (WP608) was then filtered and washed with diethyl ether. WP608 was recrystallized from methanol:diethyl ether and dried under reduced pressure. Yield 386 mg (86.9%); m.p. 109°–111° C. (with decomposition), [α]D 182° (c 0.02, chloroform: methanol 1:1). Elemental analysis for C$_{27}$H$_{29}$O$_{10}$N·HCl: Calc: C 57.50, H 5.36, N 2.48; Found: C 57.31, H 5.42, N 2.40.

α,α'-Bis-4'-N-(4'-amino-3'-deamino-4'-deoxy-3'-hydroxydaunorubicin)-p-xylene hydrochloride (WP652)

WP608 (220 mg, 0.39 mmol) was dissolved in a mixture of DMF and CH$_2$Cl$_2$ (1:1 v/v), (5 mL). Then, Na$_2$CO$_2$ (80 mg) and α,α-di-bromo-p-xylene (52.8 mg 0.20 mmol) were added. The reaction mixture was stirred at room temperature for 20–28 hr. The progress of the reaction was monitored by TLC (chloroform : methanol : NH$_4$OH aq 86:13:1). After the reaction was complete, the mixture was diluted with dichloromethane (100 mL) and poured into the water (100 mL). Organic layer was separated and washed with water until neutral, then dried with anhydrous Na$_2$SO$_4$ and evaporated under diminished pressure. Crude product was purified by column chromatography using first CHCl$_3$ and then CHCl$_3$:MeOH 98:2 and CHCl$_3$:MeOH 95:5 as eluents. The product obtained after chromatography was precipitated from dichloromethane:hexane to give a red solid (142.0 mg, 0.122 mmol) in 63% yield. Elemental analysis for C$_{62}$H$_{64}$O$_{20}$N$_2$: Calc: C 64.35, H 5.57, N 2.42; Found C 64.43, H 5.61, N 2.34. 1H-NMR (CDCl$_3$): δ 14.00, 13.30 (2s, 1H, 6-OH, 11-OH), 8.01 (d, J$_{2,3}$=7.3 Hz, H-3), 7.77 (dd, 1H, J$_{1,2}$=J$_{2,3}$=7.3 Hz, H-2), 7.39 (d, J$_{1,2}$=7.3 Hz, H-1), 7.33 (s, 2H, p-xylene spacer), 5.47 (d, 1H, J$_{1',2'a}$=3.51 Hz, H-1'), 5.25 (bs, 1H, H-7), 4.63 (s, 1H, 9-OH), 4.12 (d, J=13.03 Hz, CH2 from p-xylene), 4.08 (broad singlet, 4H, 4-OMe, and H-4'), 3.73 (d, 1H, J=13.03 Hz, CH2 from p-xylene), 3.68–3.63 (m, 1H, H-5'), 3.22 (d, 1H, J10a,10e=18.8 Hz, H-10), 2.93 (d, 1H, J10a,10e=18.78 Hz, H-10), 2.73 (d, 1H, J=3.25 Hz, 4'-OH), 2.41 (s, 3H, H-14), 2.29 (d, 1H, J$_{8a,8e}$=14.73 Hz, H-8e), 2.08 (dd, 1H, J$_{7,8a}$=3.67 Hz, H-8a), 1.83 (dd, 1H, J$_{2'a,2'e}$=13.4 Hz, J$_{2'e,3'}$=4.98 Hz, H-2e'), 1.52 (td, 1H, J$_{1',2'a}$=4.1 Hz, J$_{2'a,2'e}$=J$_{2'a,3'}$=12.53 Hz, H-2a'), 1.40 (d, 3H, J$_{5',6'}$=6.55 Hz, H-6').

Free amine was then suspended in MeOH (2 mL), and 1N dry HCl in MeOH was added. This was followed by addition of diethyl ether to precipitate hydrochloride. The red solid of hydrochloride WP652 was washed with ether to neutral pH and then dried under vacuum. Analytically pure WP652 (135 mg, 0.11 mmol) was isolated in 56.7% yield: mp 120° C. with decomposition; [α]D$^{30}$ 210.2° (c 0.04, CHCl$_3$ : CH$_3$OH 1:1). Elemental analysis for C$_{62}$H$_{65}$ClN$_2$O$_{20}$·4×H$_2$O: Calc: C 57.19, H 5.73, Cl 5.45 N 2.15; Found: C 56.84, H 5.75, Cl 5.42, N 2.15.

EXAMPLE II

Structure based design of Bisintercalating anthracyline Antibiotics

The present example demonstrates the effectiveness of WP631, one of the bisanthracyclines of the present invention as an effective DNA intercalating agents.

Methods

Viscosity Studies. Relative viscosity studies were conducted exactly as described previously (Suh and Chaires, 1995). Data were cast into a plot of $(\eta/\eta_0)^{1/3}$ versus ratio of bound drug per DNA base pair, in accord with the theory of Cohen and Eisenberg (1969). Ethidium bromide and daunorubicin were run as controls for these experiments.

UV Melting Studies. Ultraviolet DNA melting curves were determined using a Cary 8E UV/visible spectrophotometer (Varian, Inc., Palo Alto, Calif.), equipped with a thermoelectric temperature controller. Sonicated herring sperm DNA at a concentration near 20 μM bp in BPE buffer (2 mM NaH$_2$—PO$_4$, 6 mM Na$_2$HPO$_4$, 1 mM Na$_2$EDTA, pH 7.0) was used for melting studies. Samples were heated at a rate of 1° C. min$^{-1}$, while the absorbance at 260 nm was continuously monitored. Primary data were transferred to the graphics program Origin (Microcal, Inc., Northampton, Mass.) for plotting and analysis.

Differential Scanning Calorimetry. Differential scanning calorimetry (DSC) experiments utilized a Microcal MC2 instrument (Microcal, Inc., Northampton, MA) along with its DA2 software (July 1986 version) for data acquisition and analysis. Sonicated herring sperm DNA at a concentration of 1 mM hp in BPE buffer was used for all experiments. A scan rate of 1° C. min$^{-1}$ was used. Primary data were corrected by subtraction of a buffer-buffer baseline, normalized to the concentration of DNA base pairs, and further baseline-corrected using the Cp(0) software option. Baseline-corrected, normalized data were transferred to Origin graphics software for integration and plotting. Samples for DSC of DNA+WP631 were prepared by weighing appropriate amounts of solid WP631 were prepared by weighing appropriate amounts of solid WP631 and dissolving the solid directly into 2 mL of 1 mM DNA solution. Any undissolved drug was removed by low-speed centrifugation. The exact amount of WP63 1 bound to the DNA was determined spectrophotometrically.

Results and Discussion

Figure 20:
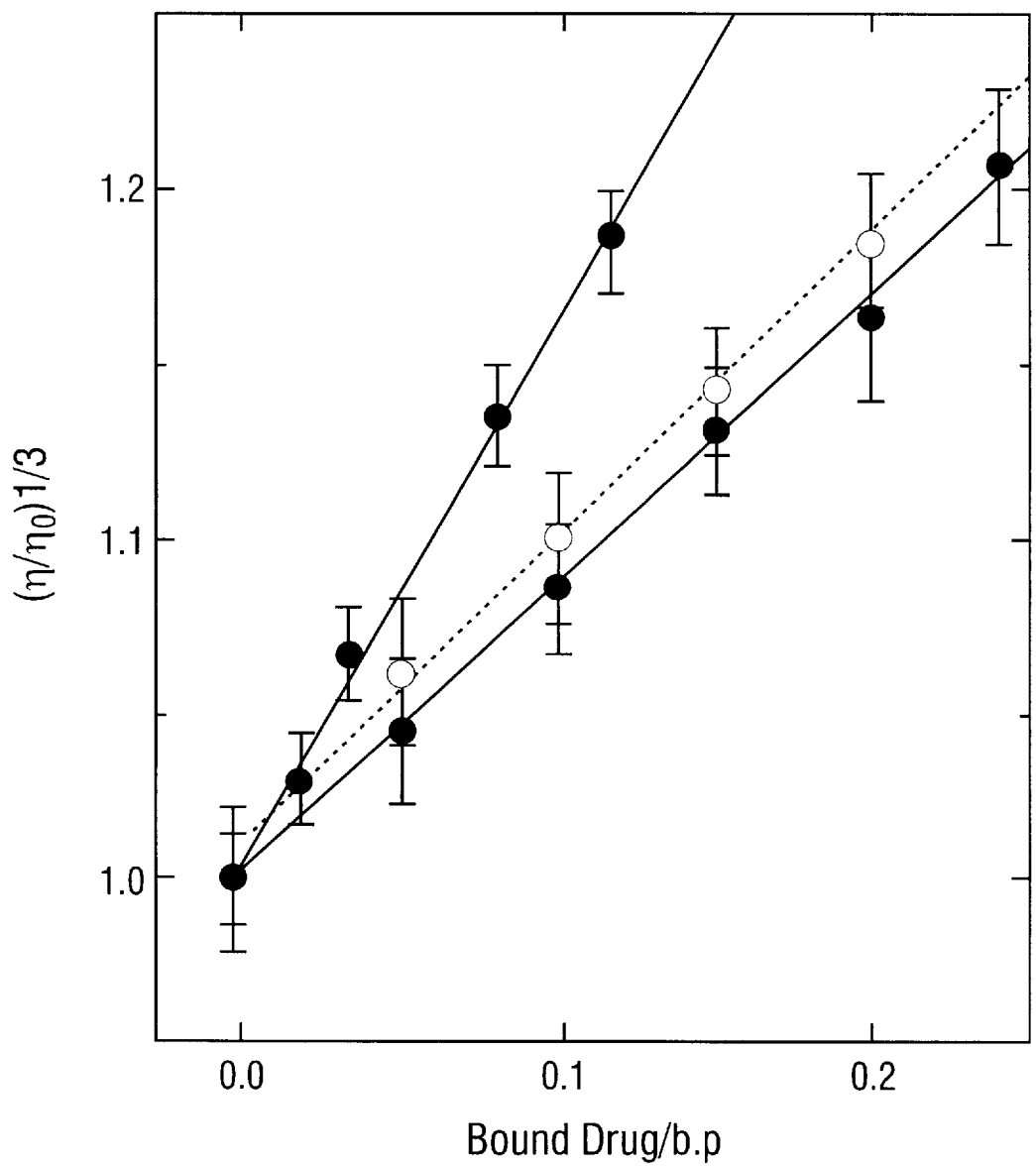
FIG. 20. Viscosity studies of WP631-DNA interaction. The cubed root of the relative viscosity ($\eta/\eta_0$) is shown as a function of the ratio of bound drug per DNA base pair: solid circles, ethidium bromide; open diamonds, daunorubicin; solid diamonds, WP63 1. Linear least squares fits to these data yielded the following slopes: ethidium, 0.84±0.02; daunorubicin, 0.89±0.04; WP631, 1.58±0.08.

WP631 Bisintercalates into DNA. In the absence of high-resolution structural data, hydrodynamic studies, especially viscosity, provide the most reliable means of inferring the binding mode of agents that interact with DNA (Suh and Chaires, 1995). FIG. 20 shows the results of viscosity experiments that verify that WP631 binds to DNA by bisintercalation. The theory of Cohen and Eisenberg (1969) predicts that, for monointercalation, plots of the cubed root of the relative viscosity $((\eta/\eta_0)^{1/3})$ versus the binding ratio (bound drug/DNA bp) ought to have a slope of 1.0.

FIG. 20 shows that the proven monointercalators ethidium and daunorubicin, run as controls in the experiment, both show viscosity changes in excellent agreement with the theory. For bisintercalators, the slope is expected to be twice that observed for monointercalators, an expectation that has been verified for a variety of bisintercalating compounds (Wakelin, 1986). The slope observed for WP631 in FIG. 20 is nearly double that observed for daunorubicin, consistent with a bisintercalative binding mode. Such a binding mode is stereochemically reasonable, as was determined by constructing a molecular model of WP631 bound to a DNA hexanucleotide (figure not shown at the suggestion of a reviewer). The model was constructed using Hyper-Chem software (v. 4.5, Hypercube, Inc.) by using the coordinates of the high-resolution structure reported by Wang et al. (1987) for a 2:1 daunorubicin-DNA complex. The sequence of the hexanucleotide in that study was d(G.CTAG.C)$_3$, where the two equivalent intercalation sites are indicated.

WP631 was built in the complex by attaching the p-xylene linker to the daunorubicin amines within the minor groove. The geometry of the drug was then optimized using the MM+force field in Hyper-Chem while constraining the DNA conformation to that observed in the crystal structure. In the resultant complex, the p-xylene linker was found to fit without steric hindrance in the minor groove and, most importantly, to be of the appropriate length to connect to the two amine without any radical change in the structure of the intercalated monomeric units. The exact orientation of the aromatic ring of the linker was found to be flexible and might be free to rotate within the minor groove.

Ultratight Binding of WP631 to DNA. The binding affinity of a bisintercalator for DNA ought to approximately equal the square of the binding constant of the corresponding monomer. Since daunorubicin binds to DNA with a binding constant of 10$^7$ M$^{-1}$ under the ionic conditions used here, a binding constant of 10$^{14}$ M$^{-1}$ is expected for WP631. Traditional spectrophotometric methods for measuring affinity fail for such ultratight binding, but optical melting studies or differential scanning calorimetry provides reliable alternatives for the accurate determination of binding constants (Crothers, 1971; McGhee, 1976; Brandts and Lin, 1990). UV melting studies were used to determine the binding constant for the interaction of WP631 with herring sperm DNA in BPE buffer (16 mM total $Na^+$). In the absence of WP631, the $T_m$ of herring sperm DNA was found to be 67.2° C. In the presence of 10 μM WP631, a concentration sufficient to saturate the DNA lattice, the $T_m$ was elevated to 93.5° C. McGhee (1976) has shown that the shift in $T_m$ is a function of the ligand binding constant and site size. Assuming no interaction of ligand with single-stranded DNA, McGhee derived the equation.

$$(1/T_m^0 - 1/T_m) = (\Delta H_m/R) \ln(1+KL)^{1/n}$$

where $T_m^0$ is the melting temperature of the DNA alone, $T_m$ is the melting temperature in the presence of saturating amounts of ligand, $\Delta H_m$ is the enthalpy of DNA melting (per bp), R is the gas constant, K is the ligand binding constant at $T_m$, L is the free ligand concentration (approximated at the $T_m$ by the total ligand concentration), and n is the ligand site size. A value of $\Delta H_m = 7.0 \pm 0.3$ kcal $mol^{-1}$ for herring sperm DNA, determined by separate differential scanning calorimetry experiments, was used. From the experimentally determined increase in $T_m$ observed for WP631, a value of $K=8.8 \times 10^6$ $M^{-1}$ (at 93.5° C.) was computed, assuming n=6 bp. Correction of this value to lower temperatures requires knowledge of the binding enthalpy, which was determined by differential scanning calorimetry.

Figure 21:
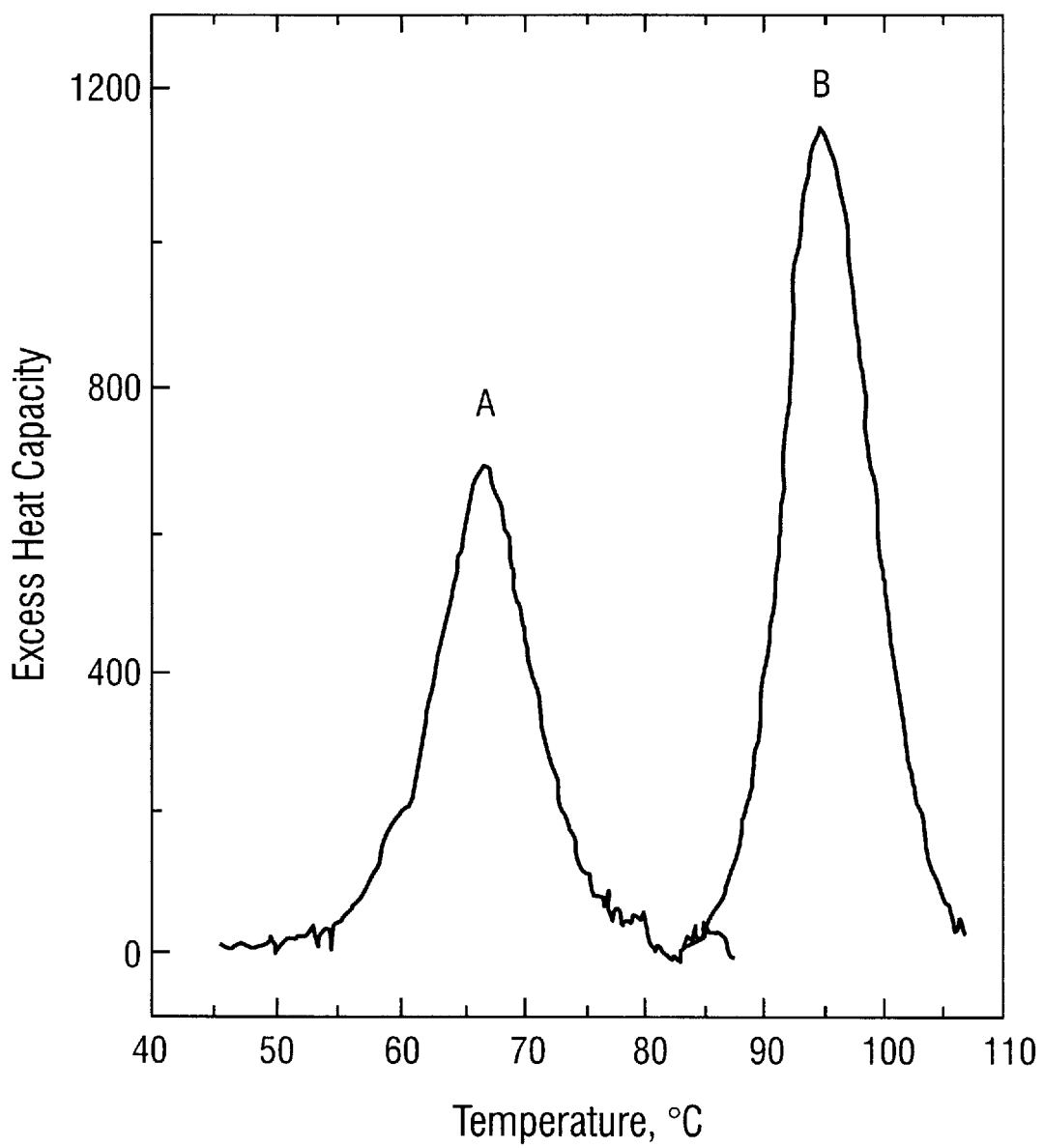
FIG. 21. Results of differential scanning calorimetry studies of the melting of herring sperm DNA alone (A) or in the presence of near saturating amounts of WP631 (B). Excess heat capacity (cal $mol^{-1}$ ° $C.^{-1}$) is plotted as a function of temperature.
Figure 22:
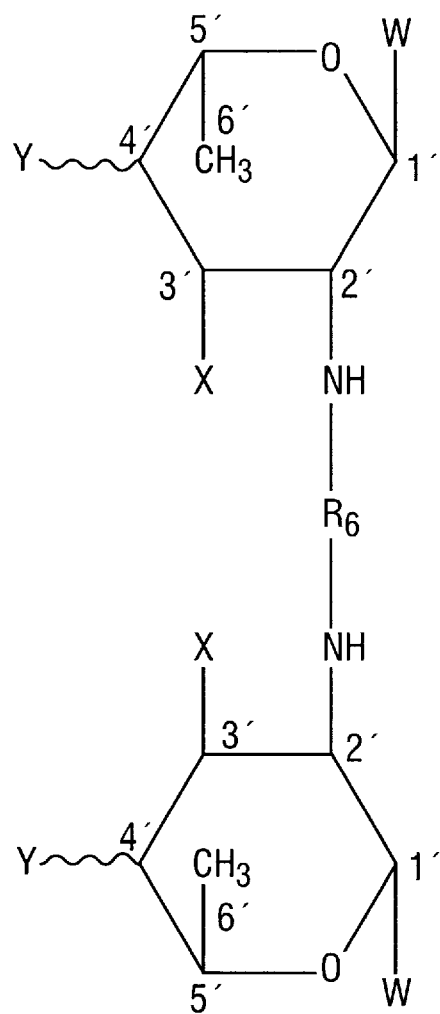
FIG. 22 shows a first anthracycline linked via the 2' amino group of its sugar moiety to the second anthracycline via the 2' amino group of a second anthracycline.
Figure 23:
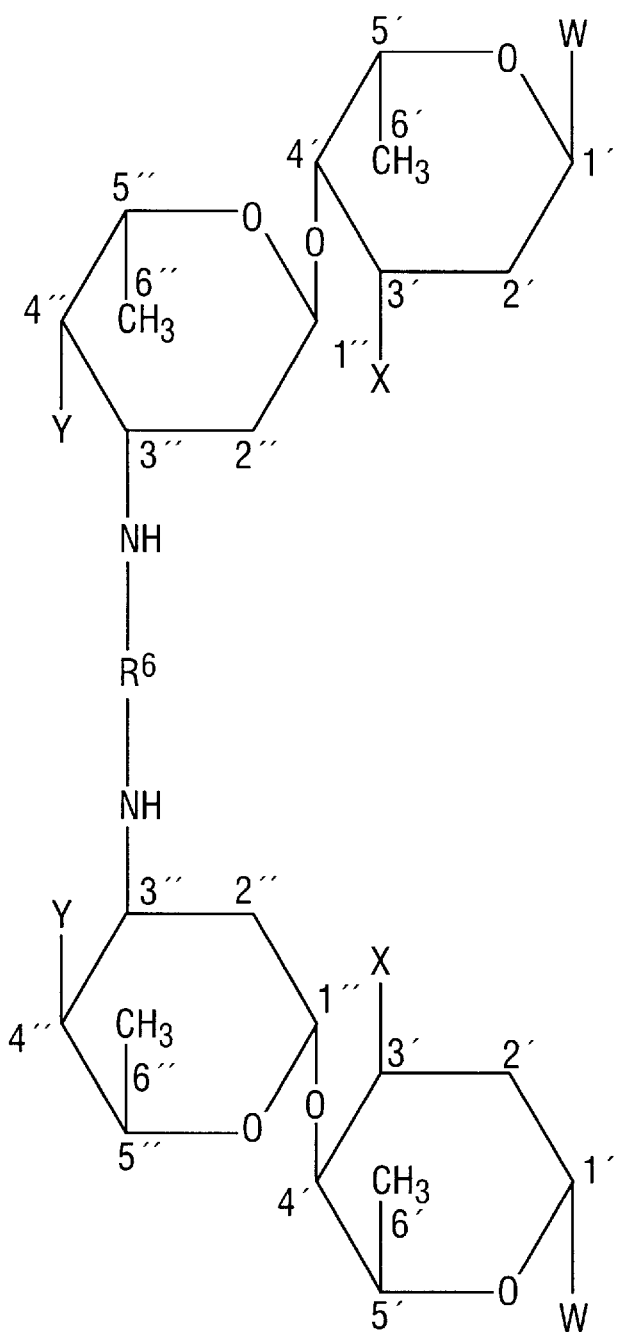
FIG. 23 shows a first anthracycline linked via the 3' amino group of a second sugar moiety of a disaccharide to the 3' amino group of a second sugar moiety in a dissacharide of the second anthracyline.
Figure 24:
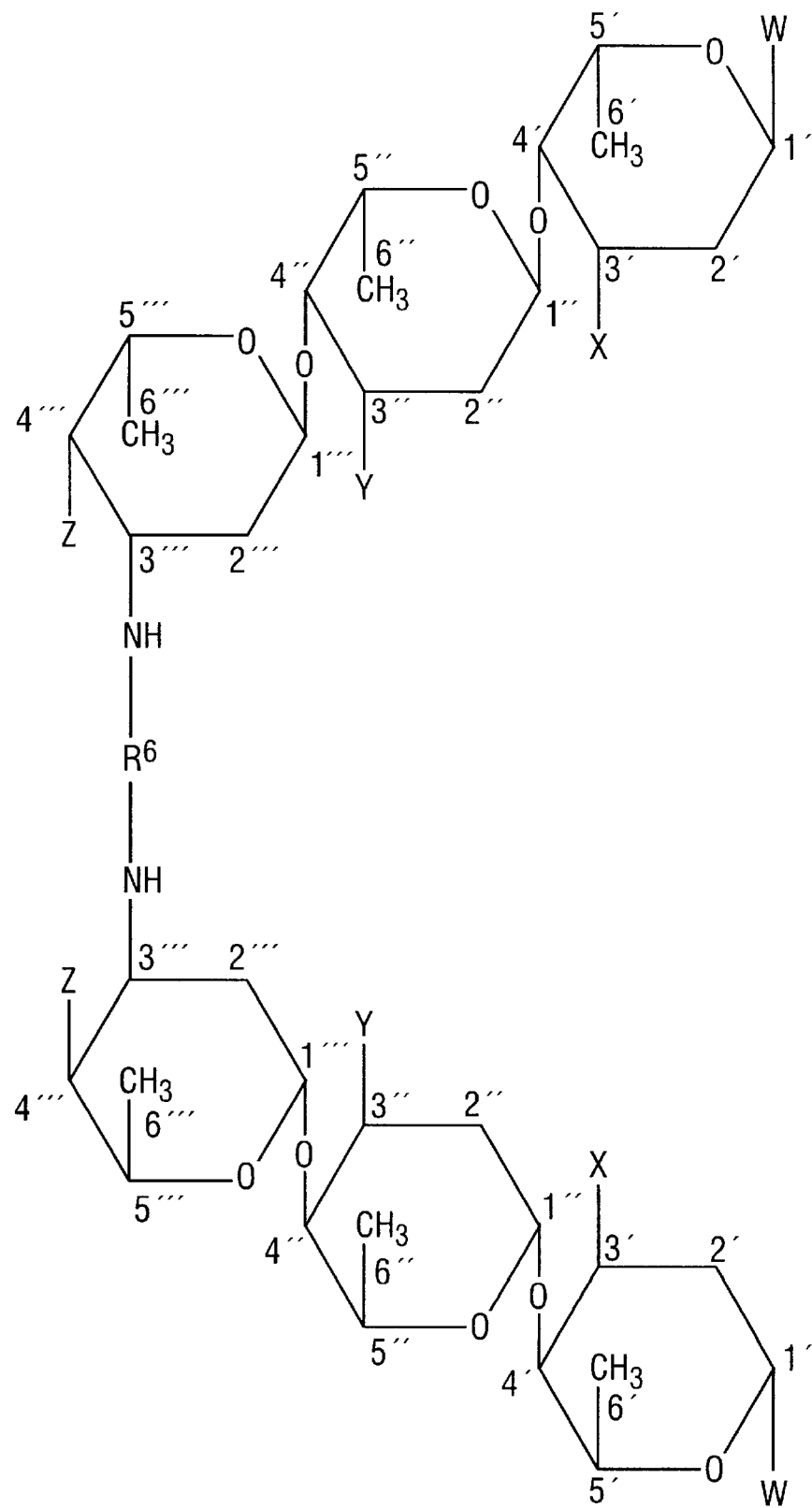
FIG. 24 shows a first anthracycline linked via the 3' amino group of a third sugar moiety of a trisaccharide to the 3' amino group of a third sugar moiety in a trissacharide of the second anthracyline.

DSC Determination of the Binding Enthalpy. FIG. 21 shows the results of differential scanning calorimetry experiments using herring sperm DNA in the presence and absence of saturating amounts of WP63 1. The area under the curves shown in FIG. 21 provides a model-free estimate of the enthalpy of melting of the DNA alone and the DNA-WP631 complex. By Hess's law, these data may be used to determine the enthalpy of WP631 binding to DNA. The equilibria to be considered, along with the experimentally determined enthalpy values, are as follows:

$$\text{duplex}=2(\text{single strand}) \Delta H=7.0 \pm 0.8 \text{ kcal mol}^{-1}$$

$$\text{WP631-duplex}=2(\text{single strand})+\text{WP631 } \Delta H_2=11.4 \pm 1.0 \text{ kcal mol}^{-1}$$

Combining these two reactions, the binding reaction and its enthalpy may be obtained:

$$\text{WP631-duplex}=\text{duplex}+\text{WP631 } \Delta H_3=\Delta H_2 - \Delta H_1$$

The enthalpy $\Delta H_3$ needs to be corrected for the amount of WP631 bound to the DNA, and the sign changed, to get the binding enthalpy, $$\Delta H_b = -\Delta H_3/(\text{mol of WP631/mol of bp})$$

From five determinations, a value of $\Delta H_b = -30.2 \pm 2.6$ kcal $mol^{-1}$ was obtained for the association of WP631 with DNA.

Complete Thermodynamic Profile for the Binding of WP631 to DNA. $\Delta H_b$ may be used, assuming that it is constant with temperature, to calculate the binding constant at 20° C. by application of the standard van't Hoff equation, yielding a value of $2.7 \times 10^{11}$ $M^{-1}$. In BPE buffer at 20° C., the binding constant for the interaction of daunorubicin with herring sperm DNA is $1.6 \times 10^7$ $M^{-1}$ (Leng and Chaires, unpublished data), so the binding constant of WP631 indeed approaches the value expected for a bisintercalator. The magnitude of the WP631 binding constant approaches that observed for the binding of many regulatory proteins for their specific DNA binding sites. Knowledge of the binding constant and the binding enthalpy allows us to construct the complete thermodynamic profile for the binding of WP631 to DNA. The free energy is obtained from the standard relation $\Delta G^0 = -RT \ln K$, yielding a value of $-15.3$ kcal $mol^{-1}$ at 20° C. The entropy may be evaluated from the equation $-T\Delta S = \Delta G - \Delta H$, yielding $\Delta S = -51$ cal $mol^{-1}$ $K^{-1}$ at 20° C. The thermodynamic profile indicates that the large, favorable binding free energy of $-15.3$ kcal $mol^{-1}$ is derived from the large negative enthalpic contribution of $-30.2$ kcal $mol^{-1}$. Binding is opposed by an unfavorable entropic contribution of $T\Delta S = -14.9$ kcal $mol^{-1}$ at 20° C.

Comparison with Daunorubicin Binding. Under comparable ionic conditions, the thermodynamic profile for daunorubicin binding to herring sperm DNA is $\Delta G^0 = -9.9$ kcal $mol^{-1}$, $\Delta H = -10.8$ kcal $mol^{-1}$, and $\Delta S = -3$ cal $mol^{-1}$ $K^{-1}$ (Leng and Chaires, unpublished data). Comparison shows that while the DNA binding of both daunorubicin and WP631 is driven by the enthalpy contribution, WP631 shows a comparatively larger unfavorable entropic contribution. Two plausible contributions to this behavior could be WP631 effects on DNA structure and losses of conformational freedom in WP631. The bisintercalation of WP631 could result in a proportionally larger increase of the stiffness of the DNA helix relative to daunorubicin, and thus a greater unfavorable entropic cost for the loss of DNA conformational freedom. In addition, preliminary molecular modeling studies have indicated that there is considerable conformational freedom in WP631, with free rotation about many of the bonds in the linker. An unfavorable entropic contribution might come from the restriction of this conformational freedom upon bisintercalation, an effect in addition to the general entropic cost for bimolecular complex formation resulting from the loss of translational and rotational freedom of the reacting partners.

EXAMPLE III

Assessment of antitumor activity in vitro

Compounds synthesized using the methods described above were tested using a standard MTT assay (Green et al., 1984) against human carcinoma sensitive (KB-3-1) and multi-drug-resistant ( KB-V-1) cells and MCF-7 and MCF-7/VP-16 resistant cells characterized as having the MRP (multi-drug resistant associated protein) phenotype. The use of an MTT assay using these cells is recognized as an accepted assay for anti-tumor activity by those in the field.

Methods

In vitro Cytotoxicity against MCF-7 and MCF-7/VP-16 Cell Lines. In vitro drug cytotoxicities against human breast carcinoma wild-type MCF-7 and MRP-resistant MCF-7/VP-16 cells were assessed by using the MTT reduction assay, as previously reported (Green et al., 1984). The MTT dye was obtained from Sigma Chemical Co. (St. Louis, Mo.). Cells were plated in 96-well microassay culture plates ($10^4$ cells/well) and grown overnight at 37° C. in a 5% $CO_2$ incubator. Drugs were then added to the wells to achieve a final drug concentration ranging from 0.1 to 50 μg/mL. Four wells were used for each concentration. Control wells were prepared by adding appropriate volumes of calcium- and magnesium-free PBS (pH 7.4). Wells containing culture medium without cells were used as blanks. The plates were incubated at 37° C. in a 5% $CO_2$ incubator for 72 h. Upon completion of the incubation, 20 μL of stock MTT dye solution (5 mg/mL) was added to each well. After a 4 h incubation, 100 μL of buffer containing 50% N,N-dimethylformamide and 20% SDS was added to solubilize the MTT formazan. Complete solubilization was achieved by placing the plate in a mechanical shaker for 30 min at room temperature. The optical density of each well was then measured with a microplate spectrophotometer at a wavelength of 570 nm. The percent cell viability was calculated by the following equation:

% cell viability=(OD treated wells/OD control wells)×100 where OD is the mean optical density from four determinations. The percent cell viability values were plotted against the drug concentrations used, and the $ID_{50}$ was calculated from the curve. Cytotoxicity experiments were repeated at least three times.

Results and Discussion

In vitro cytotoxic activity of WP652 against human carcinoma sensitive (KB-3-1 ) and multi-drug resistant (KB-V-1) cell lines. Drug resistance, both de novo and acquired, by human tumors is currently a major factor limiting the effectiveness of chemotherapy. Thus, for the inventor's in vitro evaluation of compound WP652 the inventors selected two cell lines: a sensitive line (human carcinoma KB-3-1), and its multi-drug-resistant (MDR) counterpart (KB-V1 carcinoma) overexpressing MDR1 gene, which encodes a membrane transport glycoprotein (P-gp). Using this system the inventors evaluate a drug's cytotoxic potential against human tumors and at the same time identify compounds that might have unique activity against MDR tumors (Priebe et al., 1993).

Table 2 shows the in vitro evaluation of cytotoxic properties of bisanthracycline WP652 and doxorubicin (DOX) in KB-3-1 and KB-V1 cells. In sensitive KB-3-1 cells, WP652 and DOX had similar cytotoxic potentials. However, in the MDR KB-V1 cells, a dramatic difference in cytotoxicity was noted. DOX appeared to be inactive. Its measured $ID_{50}$ was 299 nmol/mL, indicating that to achieve a 50% cell kill the DOX dose has to be increased 80.8 times. The KB-V1 cells are also highly resistant to vinblastine and other clinically used MDR drugs. Totally different results were obtained for WP652, which appeared to be unusually active against the MDR cells. WP652's measured resistance index (RI=the ratio of $ID_{50}$ in sensitive cells to $ID_{50}$ in resistant cells) was very small (RI=1.5), and its cytotoxic potential was only minimally reduced when compared with DOX, thus indicating that WP652 can overcome MDR.

TABLE 2

Cytotoxicity of WP 652 against sensitive (KB-3-1) and MDR human carcinoma (KB-V-1) $ID_{50}$ (nmol/mL)

| DRUG | KB-3-1 | KB-V-1 | RI |
|---|---|---|---|
| WP 652 | 4.8 ± 0.5 | 7.1 ± 1.2 | 1.5 |
| DOX | 3.7 ± 1.3 | 299 ± 55 | 80.8 |

In vitro cytotoxic activity of WP631 and WP652 against MCF-7 sensitive and MCF-7/VP-16 multi-drug resistant (MRP) cell lines. Compounds WP631 and WP652 were evaluated in sensitive cell line MCF-7 and its multi-drug-resistant counterpart (MCF-7/VP-16) overexpressing the gene for a multi-drug-resistance associated protein (MRP). This type of resistance was recently shown to have clinical relevance (Norris et al., 1996).

Table 3 shows the in vitro evaluation of cytotoxic properties of bisanthracyclines WP631 and WP652 and doxorubicin (DOX). In sensitive MCF-7 cells, WP652 and WP631 were less potent than DOX; however, in the MCF-7/VP-16 cells, a dramatic increase in cytotoxicity was noticed for both bisanthracyclines when compared with DOX. DOX resistance index (RI) appeared to be 34-fold higher than that of WP63 1. RIs of both WP631 and WP652 were below 1 and were 0.5 and 0.9 respectively, indicating that both compounds appeared to be more cytotoxic against resistant cells, therefore, such analogs can overcome MRP-type resistance.

TABLE 3

In vitro evaluation of cytotoxic properties of bis anthracyclines. ID50 (nmol/mL)

| DRUG | MCF-7 | MCF-7/VP16 | RI |
|---|---|---|---|
| WP631 | 4.83 ± 2.5 | 2.5 ± 3.4 | 0.5 |
| WP652 | 3.90 ± 3.3 | 3.49 ± 4.1 | 0.9 |
| DOX | 0.9 ± 0.47 | 14.90 ± 0.89 | 17 |

At present the exact reason for WP631's and WP652's high activity against resistant MDR and MRP cells is not known. However, this unique activity of bisanthracyclines clearly makes them candidates for preclinical and clinical evaluation.

EXAMPLE IV

Treatment of Tumors with Bisanthracyclines

Treatment with the bisanthracyclines and their respective free amines of the present invention is similar to the treatment regimes of other anthracyclines and their derivatives. For example, standard treatment with doxorubicin is described in *Remingtons Pharmaceutical Sciences* as follows.

Doxorubicin is administered intravenously to adults at 60 to 75 $mg/m^2$ at 21-day intervals or 25 to 30 $mg/m^2$ on each of 2 or 3 successive days repeated at 3- or 4-week intervals or 20 $mg/m^2$ once a week. The lowest dose should be used in elderly patients, when there is prior chemotherapy or neoplastic marrow invasion, or when the drug is combined with other myelopoietic suppressant drugs. The dose should be reduced by 50% if the serum bilirubin lies between 1.2 and 3 mg/dL and by 75% if above 3 mg/dL. The lifetime total dose should not exceed 550 $mg/m^2$ in patients with normal heart function and 400 $mg/m^2$ in patients with normal heart function and 400 $mg/m^2$ on each of 3 consecutive days, repeated every 4 weeks. Prescribing limits are as with adults. It has been reported that a 96-hr continuous infusion is as effective as and much less toxic than the same dose given by golus injections.

Of course, modifications of the treatment regimes due to the unique nature of the bisanthracyclines of the present invention are possible and well within the ability of one skilled in the art. Appropriate modifications may be ascertained by following the protocols in the following examples for in vivo testing and developments of human protocols.

EXAMPLE V

In Vivo Prevention of Tumor Development using Bis-Anthracycline Compounds

In an initial round of in vivo trials, a mouse model of human cancer with the histologic features and metastatic potential resembling tumors seen in humans (Katsumata et al., 1995) is used. The animals are treated with bisanthracyclines of the present invention to determine the suppression of tumor development.

Bisanthracyclines are tested in vivo for antitumor activity against murine leukemia L1210, P388, and P388 resistant to doxorubicin. In conjunction with these studies, the acute and sub-acute toxicity is studied in mice (LD10, LD50, LD90). In a more advanced phase of testing, the antitumor activity of bisanthracyclines against human xenografts is assessed and cardiotoxicity studies performed is done in a rat or rabbit model.

These studies are based on the discovery that bisanthracycline compounds of the current invention have anti-cancer activity for MDR cancer cells. The current example uses of bisanthracyclines, to provide a useful preventive and therapeutic regimen for patients with MDR tumors Two groups of mice of a suitable cancer model are treated with doses of bisanthracyclines. Several combinations and concentrations of bisanthracyclines is tested. Control mice are treated with buffer only.

The effect of bisanthracyclines, on the development of breast tumors is compared with the control group by examination of tumor size, and histopathologic examination (breast tissue is cut and stained with hematoxylin and eosin) of breast tissue. With the chemopreventive potential of WP631 and other bisanthracyclines of the present invention, it is predicted that, unlike the control group of mice that develop tumors, the testing group of mice is resistant to tumor development.

EXAMPLE VI

Human Treatment with bisanthracyclines

This example describes a protocol to facilitate the treatment of cancer using bisanthracyclines.

A cancer patient presenting for example, a MDR cancer are treated using the following protocol. Patients may, but need not, have received previous chemo- radio- or gene therapeutic treatments. Optimally the patient exhibits adequate bone marrow function (defined as peripheral absolute granulocyte count of >2,000/mm3 and platelet count of 100,000/mm3, adequate liver function (bilirubin 1.5 mg/dl) and adequate renal function (creatinine 1.5 mg/dl).

Protocol for the Treatment of Multi-Drug Resistant Cancer

A composition of the present invention is typically administered orally or parenterally in dosage unit formulations containing standard, well known non-toxic physiologically acceptable carriers, adjuvants, and vehicles as desired. The term parenteral as used herein includes subcutaneous injections, intravenous, intramuscular, intra-arterial injection, or infusion techniques. The bisanthracyclines may be delivered to the patient before, after or concurrently with the other anti-cancer agents.

A typical treatment course may comprise about six doses delivered over a 7 to 21 day period. Upon election by the clinician the regimen may be continued six doses every three weeks or on a less frequent (monthly, bimonthly, quarterly etc.) basis. Of course, these are only exemplary times for treatment, and the skilled practitioner will readily recognize that many other time-courses are possible.

A major challenge in clinical oncology of is that many cancers are multi drug resistant. One goal of the inventors' efforts has been to find ways to improve the efficacy of chemotherapy. In the context of the present invention, WP631 or WP652 are bis-anthracyclines that have a surprising activity against such cancers.

To kill MDR cancer cells using the methods and compositions described in the present invention one will generally contact a target cell with a bisanthracycline of the present invention. These compositions are provided in an amount effective to kill or inhibit the proliferation of the cell.

In certain embodiments, it is contemplated that one would contact the cell with agent(s) of the present invention about every 6 hours to about every one week. In some situations however, it may be desirable to extend the time period for treatment significantly where several days (2, 3, 4, 5, 6, 7 or more) to several weeks (1, 2, 3, 4, 5, 6 , 7 or more) lapse between respective administrations.

Regional delivery of a bisanthracycline is an efficient method for delivering a therapeutically effective dose to counteract the clinical disease. Likewise, the chemotherapy may be directed to a particular effected region. Alternatively systemic delivery of active agents may be appropriate.

The therapeutic composition of the present invention is administered to the patient directly at the site of the tumor. This is in essence a topical treatment of the surface of the cancer. The volume of the composition should usually be sufficient to ensure that the tumor is contacted by the bisanthracycline.

In one embodiment, administration simply entails injection of the therapeutic composition into the tumor. In another embodiment, a catheter is inserted into the site of the tumor and the cavity may be continuously perfused for a desired period of time.

Clinical responses may be defined by acceptable measure. For example, a complete response may be defined by the disappearance of all measurable disease for at least a month. Whereas a partial response may be defined by a 50% or greater reduction of the sum of the products of perpendicular diameters of all evaluable tumor nodules or at least I month with no tumor sites showing enlargement. Similarly, a mixed response may be defined by a reduction of the product of perpendicular diameters of all measurable lesions by 50% or greater with progression in one or more sites.

Of course, the above-described treatment regimes may be altered in accordance with the knowledge gained from clinical trials such as those described in Example VI. Those of skill in the art is able to take the information disclosed in this specification and optimize treatment regimes based on the clinical trials described in the specification.

EXAMPLE VII

Clinical Trials of the Use of Bisanthracyclines in Treating Multi-Drug Resistant Cancer This example is concerned with the development of human treatment protocols using the isanthracyclines. These compounds are of use in the clinical treatment of various MDR cancers in which transformed or cancerous cells play a role. Such treatment is particularly useful tools in anti-tumor therapy, for example, in treating patients with ovarian, breast and lung cancers that are resistant to conventional chemotherapeutic regimens.

The various elements of conducting a clinical trial, including patient treatment and monitoring, is known to those of skill in the art in light of the present disclosure. The following information is being presented as a general guideline for use in establishing WP631 or WP652 and other anthracycline drugs made by the use of this invention, in clinical trials.

Patients with human metastatic breast and/or epithelial ovarian carcinoma, colon cancer leukemia, or sarcoma are chosen for clinical study. Measurable disease is not required, however the patient must have easily accessible pleural effusion and/or ascites. Further the patients must carry tumors that express MDR phenotype. In an exemplary clinical protocol, patients may undergo placement of a Tenckhoff catheter, or other suitable device, in the pleural or peritoneal cavity and undergo serial sampling of pleural/peritoneal effusion. Typically, one will wish to determine the absence of known loculation of the pleural or peritoneal cavity, creatinine levels that are below 2 mg/dl, and bilirubin levels that are below 2 mg/dl. The patient should exhibit a normal coagulation profile.

In regard to the bisanthracycline drug administration, a Tenckhoff catheter, or alternative device may be placed in the pleural cavity or in the peritoneal cavity, unless such a device is already in place from prior surgery. A sample of pleural or peritoneal fluid can be obtained, so that baseline cellularity, cytology, LDH, and appropriate markers in the fluid (CEA, CA15-3, CA 125, p185) and in the cells (E1A, p185) may be assessed and recorded.

In the same procedure, bisanthracyclines may be administered. The administration may be in the pleural/peritoneal cavity, directly into the tumor, or in a systemic manner. The starting dose may be 0.5 mg/kg body weight. Three patients may be treated at each dose level in the absence of grade >3 toxicity. Dose escalation may be done by 100% increments (0.5 mg, 1 mg, 2 mg, 4 mg) until drug related grade 2 toxicity is detected. Thereafter, dose escalation may proceed by 25% increments. The administered dose may be fractionated equally into two infusions, separated by six hours if the combined endotoxin levels determined for the lot of bisanthracycline exceed 5EU/kg for any given patient.

The bisanthracyclines may be administered over a short infusion time or at a steady rate of infusion over a 7 to 21 day period. The bisanthracycline infusion may be administered alone or in combination with the anti-cancer drug. The infusion given at any dose level is dependent upon the toxicity achieved after each. Hence, if Grade II toxicity was reached after any single infusion, or at a particular period of time for a steady rate infusion, further doses should be withheld or the steady rate infusion stopped unless toxicity improved. Increasing doses of bisanthracyclines in combination with an anti-cancer drug is administered to groups of patients until approximately 60% of patients show unacceptable Grade III or IV toxicity in any category. Doses that are ⅔ of this value could be defined as the safe dose.

Physical examination, tumor measurements, and laboratory tests should, of course, be performed before treatment and at intervals of about 3–4 weeks later. Laboratory studies should include CBC, differential and platelet count, urinalysis, SMA-12-100 (liver and renal function tests), coagulation profile, and any other appropriate chemistry studies to determine the extent of disease, or determine the cause of existing symptoms. Also appropriate biological markers in serum should be monitored e.g. CEA, CA 15-3, p185 for breast cancer, and CA 125, p185 for ovarian cancer.

To monitor disease course and evaluate the anti-tumor responses, it is contemplated that the patients should be examined for appropriate tumor markers every 4 weeks, if initially abnormal with twice weekly CBC, differential and platelet count for the 4 weeks; then, if no myelosuppression has been observed, weekly. If any patient has prolonged myelosuppression, a bone marrow examination is advised to rule out the possibility of tumor invasion of the marrow as the cause of pancytopenia. Coagulation profile shall be obtained every 4 weeks. An SMA-12-100 shall be performed weekly. Pleural/peritoneal effusion may be sampled 72 hours after the first dose, weekly thereafter for the first two courses, then every 4 weeks until progression or off study. Cellularity, cytology, LDH, and appropriate markers in the fluid (CEA, CA15-3, CA 125, p185) and in the cells (p185) may be assessed. For an example of an evaluation profile, see Table 4. When measurable disease is present, tumor measurements are to be recorded every 4 weeks. Appropriate radiological studies should be repeated every 8 weeks to evaluate tumor response. Spirometry and DLCO may be repeated 4 and 8 weeks after initiation of therapy and at the time study participation ends. An urinalysis may be performed every 4 weeks.

Clinical responses may be defined by acceptable measure. For example, a complete response may be defined by the disappearance of all measurable disease for at least a month. Whereas a partial response may be defined by a 50% or greater reduction of the sum of the products of perpendicular diameters of all evaluable tumor nodules or at least 1 month with no tumor sites showing enlargement. Similarly, a mixed response may be defined by a reduction of the product of perpendicular diameters of all measurable lesions by 50% or greater with progression in one or more sites.

TABLE 4

EVALUATIONS BEFORE AND DURING THERAPY

| EVALUATIONS | PRE-STUDY | TWICE WEEKLY | WEEKLY | EVERY 4 WEEKS | EVERY 8 WEEKS |
|---|---|---|---|---|---|
| History | X | | | X | |
| Physical | X | | | X | |
| Tumor Measurements | X | | | X | |
| CBC | X | $X^1$ | X | | |
| Differential | X | $X^1$ | X | | |
| Platelet Count | X | $X^1$ | X | | |
| SMA12-100 (SGPT, Alkaline Phosphatase, Bilirubin, Alb/Total Protein) | X | | X | | |
| Coagulation Profile | X | | | X | |
| Serum Tumor markers (CEA, CA15-3, CA-125, Her-2/neu) | X | | | $X^3$ | |
| Urinalysis | X | | | X | |
| X-rays: | | | | | |
| chest | X | | $X^4$ | | |
| others | X | | | | X |
| Pleural/Peritoneal Fluids: (cellularity, cytology, LDH, tumor markers, E1A, HER-2/neu) | X | | $X^5$ | X | |
| Spirometry and DLCO | X | | | $X^6$ | $X^6$ |

[1]For the first 4 weeks, then weekly, if no myelosuppression is observed.
[2]As indicated by the patient's condition.
[3]Repeated every 4 weeks if initially abnormal.
[4]For patients with pleural effusion, chest X-rays may be performed at 72 hours after first dose, then prior to each treatment administration.
[5]Fluids may be assessed 72 hours after the first dose, weekly for the first two courses and then every 4 weeks thereafter.
[6]Four and eight weeks after initiation of therapy.

While the compositions and methods of this invention have been described in terms of preferred embodiments, it is apparent to those of skill in the art that variations may be applied to the composition, methods and in the steps or in the sequence of steps of the method described herein without departing from the concept, spirit and scope of the invention.

More specifically, it is apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Apple et al., "Bis-anthracycline nucleic acid function inhibitors and improved method for administering the same."

Arcamone F., *Doxorubicin*. Anti-Cancer Antibiotics. New York: Academic Press, 1981.

Bell et al., *J. Clin. Oncol.*, 3:311, 1985

Bertino, *J. Clin. Oncol.*, 3:293, 1985

Bodley, et al., *Cancer Res.*, 49:5969–5978, 1989.

Bodley et al., *Cancer Res.*, 49:5969.

Booser D J and Hortobagyi G N., "Anthracycline Antibiotics in Cancer Therapy. Focus on Drug Resistance", Drugs, 47:223–258, 1994.

Bradley et al., *Biochem. Biophys. Acta.*, 948:87, 1988.

Brandts and Lin, "Study of Strong to Ultratight Protein Interactions Using Differential Scanning Calorimetry", Biochemistry, 29:6927–6940, 1990.

Capranico et al., "Sequence-Selective Topoisomerase II Inhibition by Anthracycline Derivatives in SV40 DNA: Relationship with DNA Binding Affinity and Cytotoxicity", Biochem, 29:562–569, 1990.

Chaires, et al., *Biochemistry*, 29:6145–6153, 1990.

Chaires J B. *Application of Equilibrium Binding Methods to Elucidate The sequence Specificity of Antibiotic Binding to DNA*. In: Hurley L H, ed. Advances in DNA Sequence Specific Agents. Vol. 1: Jai Press, 1991.

Chaires J B. "Biophysical Chemistry of Daunomycin-DNA Interaction", *Biophys. Chem.*, 35:191–202, 1990.

Chaires J B. *Daunomycin Binding to DNA: From the Macroscopic to the Microscopic*. In: Pullman B, Jortner J, eds. Molecular Basis of Specificity in Nucleic Acid-Drug Interactions: Kluwer Academic Publishers, 1990:123–126.

Cohen and Eisenberg, "Viscosity and Sedimentation Study of Sonicated DNA-Proflavine Complexes", *Biopolymers*, 8:45–55, 1969.

Comblett et al., "Mitoxantrone for the Treatment of Advanced Breast Cancer: Single-Agent Therapy in Previously Untreated Patients", *Eur. J. Cancer Clin. Oncol.*, 20(9):1141–1146, 1984.

Crothers D M, "Statistical Thermodynamics of Nucleic Acid Melting Transitions with Coupled Binding Equilbria", *Biopolymers*, 10:2147–2160, 1971.

Curt et al., *Cancer Treat. Rep.*, 68:87, 1984.

Danks et al., *Cancer Res.*, 47:1297, 1987.

Dawson KM. "Activity of SC33428, a novel bis-hydrozone bridged derivative of 4-demethoxydaunomycin, against experimental tumors in mice", *Cancer Res.*, 43:2880–2883, 1983.

Denny et al., "Potential Anti-tumor Agents. 39. Anilino Ring Geometry of Amsacrine and Derivatives: Relationship to DNA binding and Anti-tumor Activity", *J. Med. Chem.*, 26(11):1625–1630, 1983.

Dervan P. *Science*, 232:464–471, 1986.

Fojo et al., *P.N.A.S.*, 84:265, 1987.

Ganapath, et al., *Br. J. Cancer*, 60:819, 1989.

Goldie et al., *Cancer Res.*, 44:3643, 1984.

Goldie et al., *Cancer Treat. Rep.*, 63:1727, 1979.

Green et al., *J. Immunol. Methods*, 70:257–268, 1984.

Gros et al., *Nature*, 323:728, 1986

Henry D W and Tong G L, "Bis(hydrazones) of daunomycin and adriamycin". U.S. Pat. No. 4,112,217, 1978.

Hsiang et al., "Topoisomerase II-Mediated DNA Cleavage by Amonafide and Its Structural Analogs", *Mol. Pharmacol.*, 36(3):371–376, 1989.

Israel et al., 1987.

Israel et al., *Cancer Chemother. Pharmacol.*, 25:177, 1989.

Katsumata et al., "Prevention of Breast Tumor Development In Vivo by Down-Regulation of the p185$^{neu}$ Receptor", *Nature Med.*, 1:644–648, 1995.

Kolate, *Science*, 231:220, 1986.

Kopka et al., "Binding of An Antitumor Drug to DNA Netropsin and C-G-C-G-A-A-T-T$^{BR}$C-C-G-C-G", *J. Mol. Biol.*, 183:553–563, 1985.

Lown J W, "Targeting the DNA Minor Groove for Control of Biological Function: Progress, Challenges and Prospects", *Chemtracts-Org. Chem.*, 6:205–237, 1903.

Lown J W, *"Anthracycline and Anthracenedione-Based Anticancer Agents,* Bioactive Molecules, Vol. 6, Amsterdam: Elsevier, 1988.

Mosmann, "Rapid Colorimetric Assay for Cellular Growth and Survival: Application to Proliferation and Cytotoxicity Assay", *J. Immunol. Methods*, 65:55–63, 1983.

Mrksich et al., "Antiparallel Side-by-Side Dimeric Motif for Sequence-Specific Recognition in the Minor Groove of DNA by the Designed Peptide 1-Methylimidazole-2-Carboxamide Netropsin", *Proc. Nat'l. Acad. Sci. U.S.A.*, 89:7586–7590, 1992.

McGhee J D, "Theoretical Calculations of the Halix-Coil Transition of DNA in the Presence of Large, Cooperatively Binding Ligands", Biopolymers, 15:1345–1375, 1976.

Norris et al., "Expression of the gene for multidrug-resistance-associated protein and outcome in patients with neuroblastoma", *N. Engl. J. Med*, 334:231–238, 1996.

Nowell, *Cancer Res.*, 46:2203, 1986.

Pelton and Wemmer, "Structural Characterization of a 2:1 Distamycin A-d(CGCAAATTGGC) Complex by Two-Dimensional NMR, *Proc. Nat'l. Acad. Sci. U.S.A.*, 86:5723–5727, 1989.

Phillips et al., "Bis-daunomycin hydrazones: Interactions with DNA", *Investigational New Drugs*, 10:79–88, 1992.

Pommier et al., *Cancer Res*.

Priebe et al., "3'-Hydroxy-esorubicin halogenated at C-2'", *J. Antibiot*, 45:386–393, 1992.

Priebe et al., "Removal of the basic center from doxorubicin partially overcomes multidrug resistance and decreases cardiotoxicity", *Anti-Cancer Drugs*, 4:37–48, 1993.

Priebe W, "Anthracycline Antibiotics. Novel Analogues, Methods of Delivery, and Mechanisms of Action", Washington, D.C.: American Chemical Society, 1995.

Priebe W. "Mechanism of Action-Governed Design of Anthracycline Antibiotics: A "Turn-Off/Turn-On" Approach", *Current Pharmaceutical Design*, 1:51–68, 1995.

Pullman B, *Advances in Drug Res.*, 18:1–100, 1989.

Pullman B, "Sequence specificity in the binding of anti-tumor anthracyclines to DNA: a success of theory", *Anti-Cancer Drug Design*, 7:95–105, 1991.

Rubinstein et al., "Comparison of In Vitro Anti-Cancer-Drug-Screening Data Generated with A Tetrazolium Assay Versus a Protein Assay Against a Diverse Panel of Human Tumor Cell Lines", *J. Nat'l. Cancer Inst.*, 82:1113–1120, 1990.

Skorobogaty et al., "The DNA-Association and Biological Activity of a New Bis (14-thiadaunomycin)", *Anti-Cancer Drug Des.,* 3:41–56, 1988.

Shu and Chaires, "Criteria for the Mode of Binding of DNA Binding Agents", *Bioorg. Med. Chem.,* 3:723–728, 1995.

Stryer, "Biochemistry", Freeman and Co., 1981.

Sweatman et al, *J. Cell. Pharmacol.,* 1:95–102.

Talbot, et al., "Anthrpyrazole CI941: A Highly Active New Agent in the Treatment of Advanced Breast Cancer", *J. Clin. Oncol.,* 9(12):2141–2147, 1991.

Traganos et al., *Cancer Res.,* 45:6273, 1985.

Valentini et al., "Association of anthracycline derivatives with DNA: A fluorescence study", *II Farmaco Ed. Sci.,* 40:377–390, 1985.

Wakelin LPG, "Medicinal Research Rev.", 6:275–340, 1986.

Wang et al., "Interactions between an Anthracycline Antibiotic and DNA: Molecular Structure of Daunomycin Complexed to d(CpGpTpApCpGp) at 1.2-A Resolution", *Biochemistry,* 26:1152–1163, 1987.

Wang et al., In: Pullman B, Jortner J, eds. *Molecular basis of specificity in nucleic acid—drug interactions,* Dordrecht (The Netherlands): Kluwer Academic Publishers, 1–24, 1990.

Wilson W D, *Reversible Interactions of Nucleic Acids with Small Molecules,* In Nucleic Acids in Chemistry and Biology Blackburn, G. M., Guit, M. J., Eds.; IRL Press, Oxford 297–336, 1990.

Young et al., *N. Engl. J. Med.,* 312:692, 1985.

U.S. Pat. No. 4,263,428 Apr. 21, 1981.

What is claimed is:

1. A compound comprising a first anthracycline analog operatively linked via a linker to a second anthracycline analog through a saccharide unit of the first anthracycline analog to the second anthracycline analog.

2. The compound of claim 1, further comprising a third anthracycline analog operatively linked to said first or said second anthracycline analog.

3. The compound of claim 1, wherein said first and second anthracycline analogs are operatively linked through a saccharide unit of the first anthracycline analog and a saccharide unit of the second anthracycline analog.

4. The compound of claim 1, wherein at least one of the first anthracycline analog or the second anthracycline analog is doxorubicin, daunorubicin, idarubicin, epirubicin, pirarubicin, esorubicin, carminomycin, or aclacinomycin.

5. The compound of claim 1, wherein the saccharide unit of at least one of the first anthracycline analog or the second anthracycline analog is a mono-, di-, or oligosaccharide.

6. The compound of claim 1, wherein the linker is a phenyl group, a benzyl group, an aryl group, an alkyl group, a heterocycle, an aromatic heterocycle, a cycloalkane group, a cycloalkyl group, an alkylaryl group, an aryloalky group, aryl group linked to another aryl group through an ester linkage, an aryl group linked to an alkyl group with an ester linkage, an aryl group linked to another aryl group through an ether linkage, an aryl group linked to an alkyl group through a thiolester linkage, an alkyl group linked to another alkyl group through an ester linkage, an alkyl group linked to another alkyl group through an ether linkage, an alkyl group linked to another alkyl group through an amino group, an aryl group linked to an alkyl through an amino group, an alkyl group linked to another alkyl group through a disulphide group, an aryl group linked to another alkyl group through a disulphide group, an aryl group linked to another aryl group through a disulphide group, an alkyl group linked to another alkyl group through a thioester linkage, an aryl group linked to an alkyl group through a polyester linkage, an aryl group linked to another aryl group through a polyester linkage, an alkyl group linked to another alkyl group through a polyamine linkage, an aryl group linked to an alkyl group through a polyamine linkage, an aryl group linked to another aryl through a polyamine linkage, an alkyl group linked to another alkyl group through a polythioester linkage, an aryl group linked to an alkyl group through a polythioester linkage, or an aryl group linked to another aryl through a polythioester linkage.

7. A compound having the formula:

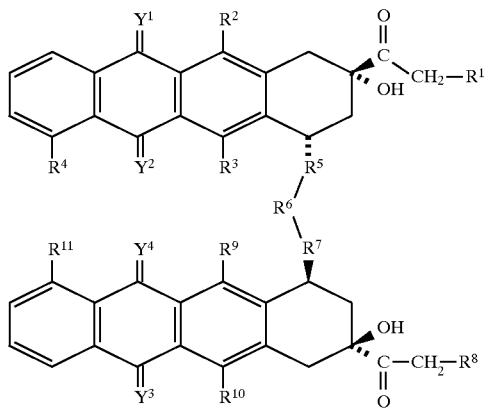

wherein:

$R^1$ is a hydrogen (—H) group, an hydroxyl group (—OH), a methoxy group (—OCH$_3$), a fatty acyl group having the general structure —O—CO(CH2)$_n$CH$_3$, wherein n is an integer from 1 to about 20, or a fatty acyl group having the general structure —O—CO(CH2)$_1$(CH=CH)$_m$(CH2)$_n$CH$_3$ 1 is an integer between 1 to 3, m is an integer between 1 and about 6 and n is an integer between 1 to about 9;

each of $R^2$, $R^3$, $R^9$, and $R^{10}$ is, independently of the others, a hydrogen (—H) group, an hydroxyl group (—OH), a methoxy group (—OCH$_3$) or a double bonded oxygen moiety;

$R^4$ and $R^{11}$ are, independently of the other, a hydrogen (—H) group, an hydroxyl group (—OH), a methoxy group (—OCH$_3$) or a halide ion;

$R^5$ and $R^7$ are, independently of each other, a saccharide or a molecule resembling a carbohydrate molecule;

$R^6$ is a phenyl group, a benzyl group, an aryl group, an alkyl group, a heterocycle, an aromatic heterocycle, a cycloalkane group, a cycloalkyl group, an alkylaryl group, an aryloalky group, an aryl group linked to another aryl group through an ester linkage, an aryl group linked to an alkyl group with an ester linkage, an aryl group linked to another aryl group through an ether linkage, an aryl group linked to an alkyl group through a thiolester linkage, an alkyl group linked to another alkyl group through an ester linkage, an alkyl group linked to another alkyl group through an ether linkage, an alkyl group linked to another alkyl group through an amino group, an aryl group linked to an alkyl through an amino group, an alkyl group linked to another alkyl group through a disulphide group, an aryl group linked to another alkyl group through a disulphide group, an aryl group linked to another aryl group through a disulphide group, an alkyl group linked to another alkyl group through a thioester linkage, an aryl group linked to an alkyl group through a polyester linkage, an aryl group linked to another aryl group through a polyester linkage, an alkyl group linked to another alkyl group through a polyamine linkage, an aryl group linked to an alkyl group through a polyamine linkage, an aryl group linked to another aryl through a polyamine linkage, an alkyl group linked to another alkyl group through a polythioester linkage, an aryl group linked to an alkyl group through a polythioester linkage, or an aryl group linked to another aryl through a polythioester linkage;

$R^8$ is a hydrogen (—H) group, an hydroxyl group (—OH), a methoxy group (—OCH$_3$), a fatty acyl group having the structure —O—CO(CH2)$_n$CH$_3$, wherein n=an integer from 1 to about 20, or a fatty acyl group having the general structure —O—CO(CH$_2$)$_l$(CH=CH)$_m$(CH$_2$)$_n$CH$_3$ where l is an integer between 1 to 3, m is an integer between 1 and 6 and n is an integer between 1–9; and each of $Y^1, Y^2, Y^3$, and $Y^4$ is, independently of the others, a hydrogen (—H) group;

an hydroxyl group (—OH); a methoxy group (—OCH$_3$); or a double bonded oxygen, suphur, or nitrogen group.

8. The compound of claim 7, wherein at least one of $R^5$ and $R^7$ is a saccharide; an aminosaccharide with the threol or erythro configuration; or with a configuration of ribose, arabinose, xylose, lyxose, allose, altrose, glucose, mannose, fructose, gulose, idose, galactose, talose, ribulose, sorbose, tagatose, gluconic acid, glucuronic acid, glucaric acididuronic acid, rhamnose, 2-dioxy-rhamnose, fucose, 2-dioxy-fucose, N-acetyl glucosamine, N-acetyl galactosamine, N-acetyl neuraminic acid, sialic acid, duanosamine, or acosamine.

9. The compound of claim 7, wherein at least one of $R^5$ and $R^7$ is a disaccharide or a polysaccharide.

10. The compound of claim 7, wherein $R^6$ is an alkyl-based group.

11. The compound of claim 10, wherein the alkyl group is of the formula CH$_3$(CH$_2$)$_n$CH$_3$ and n is an integer from 1 to about 100; an alkyl group that is a polyether; an alkyl group that is a polyamine; an alkyl group of the formula CH$_3$(CH=CH)$_n$(CH)$_m$CH$_3$ and n is an integer from 1 to about 20 and m is an integer from 1 to about 100; or an alkyl group of the formula CH$_3$(C≡C)$_n$(CH)$_m$CH$_3$ and n is an integer from 1 to about 20 and m is an integer from 1 to about 100.

12. The compound of claim 7, wherein $R^6$ is a ring-based group.

13. The compound of claim 12, wherein the ring-based group is a cyclohexane; cyclohexene; or aryl group that is is a phenyl; benzyl; toluene; aniline; cumene; styrene; benzaldehyde; biphenyl group; a xylene; an aryl group substituted with an halide ion; an aryl group substituted with an alkyl group, a methoxy group, an hydroxyl group, nitro group, amino group, an amido group, or a double bonded oxygen moiety; an aryl group is substituted with a phenyl, benzyl, cyclohexane, cyclohexene, toluene, aniline, cumene, styrene, benzaldehyde, biphenyl group, or a xylene.

14. The compound of claim 7, further defined as having the structure:

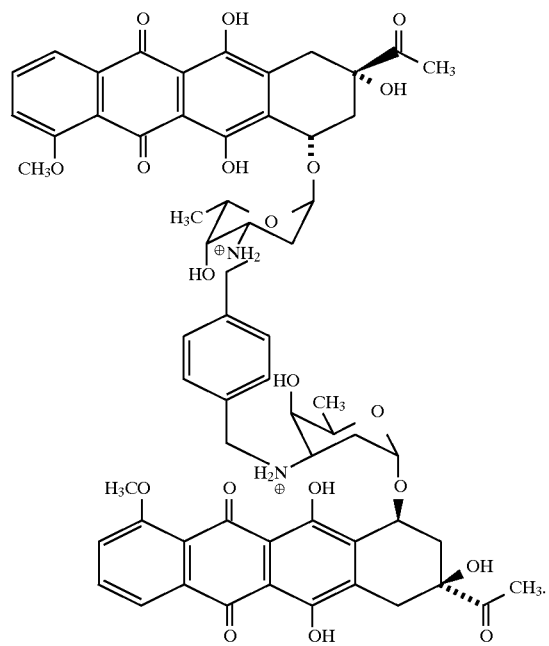

15. The compound of claim 7, further defined as having the structure:

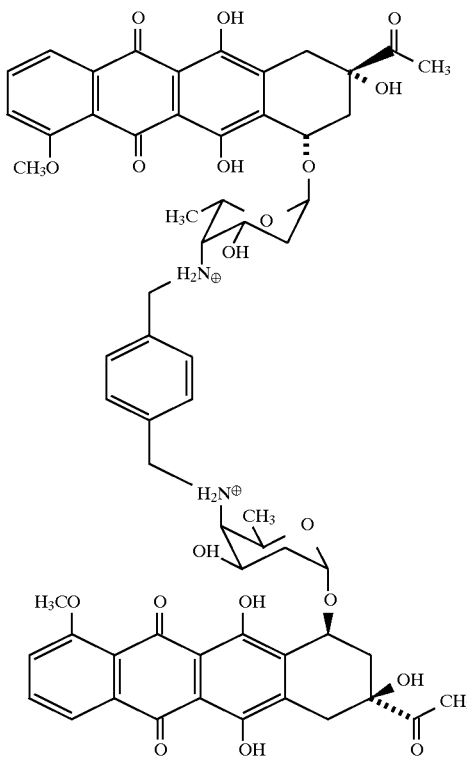

16. The compound of claim 7, further defined as having the structure shown in FIG. 15, FIG. 16, FIG. 17, FIG. 18, or FIG. 19.

17. A chloride salt of the compound of claim 7.

18. A method of preparing a compound having the formula of claim 7 comprising: preparing a first anthracycline of formula:

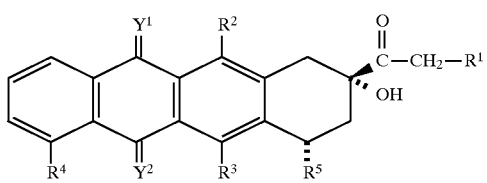

preparing a second anthracycline of general formula:

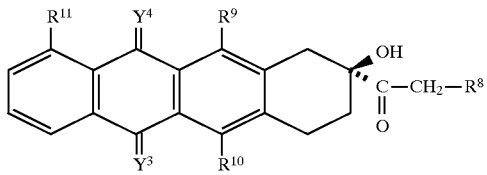

and;
conjugating said first anthracycline to said second anthracycline through a linker group.

19. The method of claim 18, wherein step (c) comprises conjugating said first anthracycline to said second anthracycline through a linker group joining their saccharide units.

20. A method of claim 18, wherein the linker group is a phenyl group, a benzyl group, an aryl group, an alkyl group, a heterocycle, an aromatic heterocycle, a cycloalkane group, a cycloalkyl group, an alkylaryl group, an aryloalky group, an aryl group linked to another aryl group through an ester linkage, an aryl group linked to an alkyl group with an ester linkage, an aryl group linked to another aryl group through an ether linkage, an aryl group linked to an alkyl group through a thiolester linkage, an alkyl group linked to another alkyl group through an ester linkage, an alkyl group linked to another alkyl group through an ether linkage, an alkyl group linked to another alkyl group through an amino group, an aryl group linked to an alkyl through an amino group, an alkyl group linked to another alkyl group through a disulphide group, an aryl group linked to another alkyl group through a disulphide group, an aryl group linked to another aryl group through a disulphide group, an alkyl group linked to another alkyl group through a thioester linkage, an aryl group linked to an alkyl group through a polyester linkage, an aryl group linked to another aryl group through a polyester linkage, an alkyl group linked to another alkyl group through a polyamine linkage, an aryl group linked to an alkyl group through a polyamine linkage, an aryl group linked to another aryl through a polyamine linkage, an alkyl group linked to another alkyl group through a polythioester linkage, an aryl group linked to an alkyl group through a polythioester linkage, or an aryl group linked to another aryl through a polythioester linkage.

21. A method of preparing a compound having the formula of claim 7, comprising adding a linker group to a solution comprising an anthracycline mixture under conditions suitable to allow conjugation.

22. The method of claim 21, wherein the linker group is a halosubstituted aryl group.

23. The method of claim 21, comprising the steps of:
adding α α' dibromoxylene to a solution of anthracycline salt to obtain a bis anthracycline linked through a xylene unit;
removing extraneous solvent to obtain a crude bis anthracycline
purifying the crude bis anthracycline; and
completing the synthesis by adding an acid to the purified bis anthracycline to obtain a salt of said bis anthracycline.

24. A method of treating a patient with cancer, comprising administering to a patient a therapeutically effective amount of a bis-anthracycline having a formula:

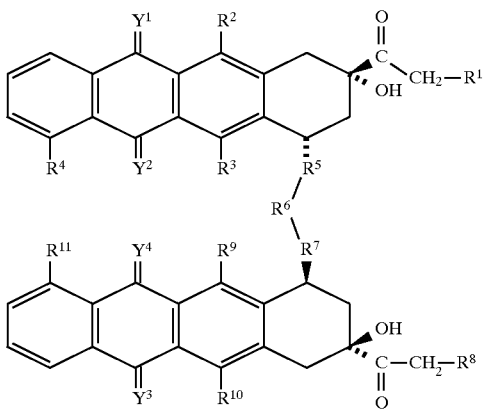

wherein:
$R^1$ is a hydrogen (—H) group an hydroxyl group (—OH), a methoxy group (—OCH$_3$), a fatty acyl group having the general structure —O—CO(CH2)$_n$CH$_3$, wherein n is an integer from 1 to about 20, or a fatty acyl group having the general structure —O—CO(CH2)$_1$(CH═CH )$_m$(CH2)$_n$CH$_3$l is an integer between 1 to 3, m is an integer between 1 and about 6 and n is an integer between 1 to about 9;

each of $R^2$, $R^3$, $R^9$, and $R^{10}$ is, independently of the others, a hydrogen (—H) group, an hydroxyl group (—OH), a methoxy group (—OCH$_3$) or a double bonded oxygen moiety;

$R^4$ and $R^{11}$ are, independently of the other, a hydrogen (—H) group, an hydroxyl group (—OH), a methoxy group (—OCH$_3$) or a halide ion:

$R^5$ and $R^7$ are, independently of each other, a saccharide or a molecule resembling a carbohydrate molecule;

$R^6$ is a phenyl group, a benzyl group, an aryl group, an alkyl group, a heterocycle, an aromatic heterocycle, a cycloalkane group, a cycloalkyl group, an alkylaryl group, an aryloalky group, an aryl group linked to another aryl group through an ester linkage, an aryl group linked to an alkyl group with an ester linkage an aryl group linked to another aryl group through an ether linkage, an aryl group linked to an alkyl group through a thiolester linkage, an alkyl group linked to another alkyl group through an ester linkage, an alkyl group linked to another alkyl group through an ether linkage, an alkyl group linked to another alkyl group through an amino group, an aryl group linked to an alkyl through an amino group, an alkyl group linked to another alkyl group through a disulphide group, an aryl group linked to another alkyl group through a disulphide group, an aryl group linked to another aryl group through a disulphide grout, an alkyl group linked to another alkyl group through a thioester linkage, an aryl group linked to an alkyl group through a polyester linkage, an aryl group linked to another aryl group through a polyester linkage, an alkyl group linked to another alkyl group through a polyamine linkage, an aryl group linked to an alkyl group through a polyamine linkage, an aryl group linked to another aryl through a polyamine linkage, an alkyl group linked to another alkyl group through a polythioester linkage, an aryl group linked to an alkyl group through a polythioester linkage, or an aryl group linked to another aryl through a polythioester linkage;

$R^8$ is a hydrogen (—H) group, an hydroxyl group (—OH), a methoxy group (—OCH$_3$), a fatty acyl group having the structure —O—CO(CH2)$_n$CH$_3$, wherein n=an integer from 1 to about 20, or a fatty acyl group having the general structure —O—CO(CH$_2$)$_l$(CH=CH)$_m$(CH$_2$)$_n$CH$_3$ where l is an integer between 1 to 3, m is an integer between 1 and 6 and n is an integer between 1–9; and each of $Y^1$, $Y^2$, $Y^3$, and $Y^4$ is, independently of the others, a hydrogen (—H) group: an hydroxyl group (—OH): a methoxy group (—OCH$_3$); or a double bonded oxygen, sulphur, or nitrogen group.

25. A therapeutic kit comprising, in suitable container means, a pharmaceutically acceptable composition comprising a bis-anthracycline, having the formula:

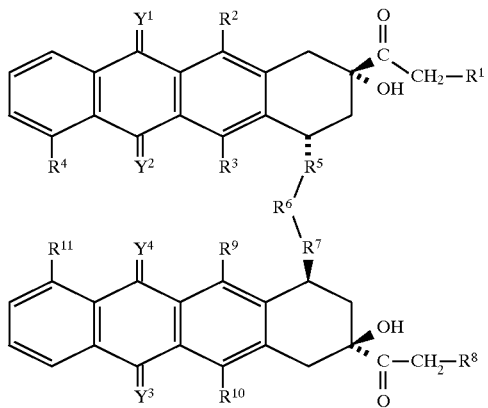

wherein:
- $R^1$ is a hydrogen (—H) group an hydroxyl group (—OH), a methoxy group (—OCH$_3$) a fatty acyl group having the general structure —O—CO(CH2)$_n$CH$_3$, wherein n is an integer from 1 to about 20, or a fatty acyl group having the general structure —O—CO(CH2)$_l$(CH=CH)$_m$(CH2)$_n$CH$_3$ l is an integer between 1 to 3, m is an integer between 1 and about 6 and n is an integer between 1 to about 9;
- each of $R^2$, $R^3$, $R^9$, and $R^{10}$ is independently of the others, a hydrogen (—H) group, an hydroxyl group (—OH), a methoxy group (—OCH$_3$) or a double bonded oxygen moiety;
- $R^4$ and $R^{11}$ are, independently of the other, a hydrogen (—H) group, an hydroxyl group (—OH), a methoxy group (—OCH$_3$) or a halide ion;
- $R^5$ and $R^7$ are, independently of each other, a saccharide or a molecule resembling a carbohydrate molecule;
- $R^6$ is a phenyl group, a benzyl group, an aryl group, an alkyl group, a heterocycle, an aromatic heterocycle, a cycloalkane group, a cycloalkyl group an alkylaryl group, an aryloalky group, an aryl group linked to another aryl group through an ester linkage, an aryl group linked to an alkyl group with an ester linkage, an aryl group linked to another aryl group through an ether linkage, an aryl group linked to an alkyl group through a thiolester linkage, an alkyl group linked to another alkyl group through an ester linkage, an alkyl group linked to another alkyl group through an ether linkage, an alkyl group linked to another alkyl group through an amino group, an aryl group linked to an alkyl through an amino group, an alkyl group linked to another alkyl group through a disulphide group, an aryl group linked to another alkyl group through a disulphide group, an aryl group linked to another aryl group through a disulphide group, an alkyl group linked to another alkyl group through a thioester linkage, an aryl group linked to an alkyl group through a polyester linkage, an aryl group linked to another aryl group through a polyester linkage, an alkyl group linked to another alkyl group through a polyamine linkage, an aryl group linked to an alkyl group through a polyamine linkage, an aryl group linked to another aryl through a polyamine linkage, an alkyl group linked to another alkyl group through a polythioester linkage, an aryl group linked to an alkyl group through a polythioester linkage, or an aryl group linked to another aryl through a polythioester linkage;
- $R^8$ is a hydrogen (—H) group, an hydroxyl group (—OH), a methoxy group (—OCH$_3$), a fatty acyl group having the structure —O—CO(CH2)$_n$CH$_3$, wherein n=an integer from 1 to about 20, or a fatty acyl group having the general structure —O—CO(CH2)$_l$(CH=CH)$_m$(CH$_2$)$_n$CH$_3$ where l is an integer between 1 to 3, m is an integer between 1 and 6 and n is an integer between 1–9; and
- each of $Y^1$, $Y^2$, $Y^3$, and $Y^4$ is, independently of the others, a hydrogen (—H) group; an hydroxyl group (—OH); a methoxy group (—OCH$_3$); or a double bonded oxygen, sulphur, or nitrogen group.

* * * * *

UNITED STATES PATENT AND TRADEMARK OFFICE
CERTIFICATE OF CORRECTION

PATENT NO. : 5,874,412
DATED : February 23, 1999
INVENTOR(S) : Priebe et al.

It is certified that error appears in the above-identified patent and that said Letters Patent is hereby corrected as shown below:

On the title page, item [76], line 5, after 'Fokt', delete "both of".

On the title page, item [76], line 5, after 'Przewloka' delete ";" and insert -- , 12000 Sawmill Rd., #1406, The Woodlands, Tex. 77380; --.

On the title page, item [60], line 1, delete "60/013,864", and insert -- 60/013,869 --.

In claim 13, column 37, line 55, after 'that' delete "is is", and insert -- is --.

In claim 24, column 40, line 22, after '(-H) group' insert -- , --.

In claim 24, column 40, line 44, after 'linkage' insert -- , --.

UNITED STATES PATENT AND TRADEMARK OFFICE
CERTIFICATE OF CORRECTION

PATENT NO. : 5,874,412
DATED : February 23, 1999
INVENTOR(S) : Priebe et al.

It is certified that error appears in the above-identified patent and that said Letters Patent is hereby corrected as shown below:

In claim 24, column 40, line 55, after 'disulphide' delete "grout", and insert -- group --.

In claim 24, column 41, line 10, after '(-H) group' delete ":" and insert -- ; --.

In claim 24, column 41, line 10, after '(-OH)' delete ":" and insert -- ; --.

In claim 25, column 41, line 33, after '(-H) group' insert -- , --.

In claim 25, column 41, line 34, after '(-OCH$_3$)' insert -- , --.

In claim 25, column 42, line 5, after 'cycloalkyl group' insert -- , --.

Signed and Sealed this

Sixth Day of July, 1999

Attest:

Q. TODD DICKINSON

*Attesting Officer*  *Acting Commissioner of Patents and Trademarks*